United States Patent
Mairs et al.

(10) Patent No.: US 11,501,867 B2
(45) Date of Patent: Nov. 15, 2022

(54) MEDICAL DEVICES AND RELATED EVENT PATTERN PRESENTATION METHODS

(71) Applicant: MEDTRONIC MINIMED, INC., Northridge, CA (US)

(72) Inventors: Nicholas S. Mairs, Minneapolis, MN (US); Robert A. Vigersky, Washington, DC (US)

(73) Assignee: Medtronic MiniMed, Inc., Northridge (CA)

( * ) Notice: Subject to any disclaimer, the term of this patent is extended or adjusted under 35 U.S.C. 154(b) by 510 days.

(21) Appl. No.: 16/175,777

(22) Filed: Oct. 30, 2018

(65) Prior Publication Data

US 2019/0066831 A1 Feb. 28, 2019

Related U.S. Application Data

(63) Continuation-in-part of application No. 16/058,736, filed on Aug. 8, 2018, which is a continuation-in-part
(Continued)

(51) Int. Cl.
*G16H 20/17* (2018.01)
*A61M 5/142* (2006.01)
(Continued)

(52) U.S. Cl.
CPC ........ *G16H 20/17* (2018.01); *A61M 5/14244* (2013.01); *G06T 11/206* (2013.01);
(Continued)

(58) Field of Classification Search
CPC ........ G16H 20/17; G16H 10/60; G16H 15/00; G16H 50/70; G16H 40/63; G16H 20/60
See application file for complete search history.

(56) References Cited

U.S. PATENT DOCUMENTS

| 3,631,847 A | 1/1972 | Hobbs, II |
| 4,212,738 A | 7/1980 | Henne |

(Continued)

FOREIGN PATENT DOCUMENTS

| DE | 4329229 | 3/1995 |
| EP | 0319268 | 6/1989 |

(Continued)

OTHER PUBLICATIONS (Animas Corporation, 1999). Animas ... bringing new life to insulin therapy. (Applicant points out, in accordance with MPEP 609.04(a), that the year of publication, 1999, is sufficiently earlier than the effective U.S. filing date, so that the particular month of publication is not in issue).

(Continued)

*Primary Examiner* — Devin C Hein
*Assistant Examiner* — Steven G.S. Sanghera
(74) *Attorney, Agent, or Firm* — Shumaker & Sieffert, P.A.

(57) ABSTRACT

Medical devices and related patient management systems and methods are provided. A method of presenting information pertaining to operation of a medical device involves obtaining historical glucose measurement data for a patient from a database, identifying, based on the historical glucose measurement data, a first set of event patterns within respective ones of a plurality of monitoring periods, obtaining an adjusted set of glucose measurement data determined based on the historical glucose measurement data and an uncertainty metric associated with the historical glucose measurement data, identifying, based on the adjusted set of glucose measurement data, one or more event patterns within respective ones of the plurality of monitoring periods, and generating a graphical user interface display comprising an event (Continued)

detection region based at least in part on the first plurality and the one or more sets of event patterns.

18 Claims, 25 Drawing Sheets

Related U.S. Application Data of application No. 15/693,238, filed on Aug. 31, 2017, now abandoned, which is a continuation-in-part of application No. 15/132,126, filed on Apr. 18, 2016, now abandoned.

(60) Provisional application No. 62/243,416, filed on Oct. 19, 2015.

(51) Int. Cl.
  *G16H 15/00* (2018.01)
  *G16H 40/63* (2018.01)
  *G16H 10/60* (2018.01)
  *G06T 11/20* (2006.01)
  *G16H 50/70* (2018.01)
  *G16H 20/60* (2018.01)
  *A61M 5/172* (2006.01)

(52) U.S. Cl.
  CPC ............ *G16H 10/60* (2018.01); *G16H 15/00* (2018.01); *G16H 20/60* (2018.01); *G16H 40/63* (2018.01); *G16H 50/70* (2018.01); *A61M 5/1723* (2013.01); *A61M 2005/14208* (2013.01); *A61M 2205/3584* (2013.01); *A61M 2205/502* (2013.01); *A61M 2205/52* (2013.01); *A61M 2230/201* (2013.01); *G06T 2200/24* (2013.01)

(56) References Cited

U.S. PATENT DOCUMENTS

| | | |
|---|---|---|
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | Decant, Jr. et al. |
| 4,494,950 A | 1/1985 | Fischell |
| 4,542,532 A | 9/1985 | McQuillkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,755,173 A | 7/1988 | Konopka et al. |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,505,709 A | 4/1996 | Funderburk et al. |
| 5,497,772 A | 5/1996 | Schulman et al. |
| 5,522,803 A | 6/1996 | Teissen-Simony |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Illiff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttlia |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,807,375 A | 9/1998 | Gross et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |

(56) References Cited

U.S. PATENT DOCUMENTS

| | | |
|---|---|---|
| 5,940,801 A | 8/1999 | Brown |
| 5,954,643 A | 9/1999 | Van Antwerp et al. |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,017,328 A | 1/2000 | Fischell et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,259,937 B1 | 7/2001 | Schulman et al. |
| 6,329,161 B1 | 12/2001 | Heller et al. |
| 6,355,021 B1 | 3/2002 | Nielsen et al. |
| 6,379,301 B1 | 4/2002 | Worthington et al. |
| 6,408,330 B1 | 6/2002 | DeLaHuerga |
| 6,424,847 B1 | 7/2002 | Mastrototaro et al. |
| 6,440,066 B1 | 8/2002 | Bardy |
| 6,472,122 B1 | 10/2002 | Schulman et al. |
| 6,484,045 B1 | 11/2002 | Holker et al. |
| 6,484,046 B1 | 11/2002 | Say et al. |
| 6,485,465 B2 | 11/2002 | Moberg et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,544,212 B2 | 4/2003 | Galley et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,589,229 B1 | 7/2003 | Connelly et al. |
| 6,591,125 B1 | 7/2003 | Buse et al. |
| 6,591,876 B2 | 7/2003 | Safabash |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,736,797 B1 | 5/2004 | Larsen et al. |
| 6,740,072 B2 | 5/2004 | Starkweather et al. |
| 6,746,582 B2 | 6/2004 | Heller et al. |
| 6,747,556 B2 | 6/2004 | Medema et al. |
| 6,749,587 B2 | 6/2004 | Flaherty |
| 6,749,740 B2 | 6/2004 | Liamos et al. |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Antwerp et al. |
| 6,809,653 B1 | 10/2004 | Mann et al. |
| 6,817,990 B2 | 11/2004 | Yap et al. |
| 6,827,702 B2 | 12/2004 | Lebel et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,153,263 B2 | 12/2006 | Carter et al. |
| 7,153,289 B2 | 12/2006 | Vasko |
| 7,303,549 B2 | 12/2007 | Flaherty et al. |
| 7,323,142 B2 | 1/2008 | Pendo et al. |
| 7,396,330 B2 | 7/2008 | Banet et al. |
| 7,399,277 B2 | 7/2008 | Saidara et al. |
| 7,402,153 B2 | 7/2008 | Steil et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,474,332 B2 | 7/2013 | Bente, IV |
| 8,674,288 B2 | 3/2014 | Hanson et al. |

(56) References Cited

U.S. PATENT DOCUMENTS

| | | | |
|---|---|---|---|
| 8,887,286 B2* | 11/2014 | Dupont | G06F 21/50 726/25 |
| 9,192,536 B2 | 11/2015 | Mackin et al. | |
| 9,420,968 B2* | 8/2016 | Kamath | A61B 5/726 |
| 10,232,114 B2 | 3/2019 | Osorio | |
| 10,561,845 B2 | 2/2020 | Giftakis et al. | |
| 2001/0044731 A1 | 11/2001 | Coffman et al. | |
| 2002/0013518 A1 | 1/2002 | West et al. | |
| 2002/0055857 A1 | 5/2002 | Mault et al. | |
| 2002/0082665 A1 | 6/2002 | Haller et al. | |
| 2002/0122063 A1 | 9/2002 | Weinberg et al. | |
| 2002/0137997 A1 | 9/2002 | Mastrototaro et al. | |
| 2002/0161288 A1 | 10/2002 | Shin et al. | |
| 2003/0060765 A1 | 3/2003 | Campbell et al. | |
| 2003/0078560 A1 | 4/2003 | Miller et al. | |
| 2003/0088166 A1 | 5/2003 | Say et al. | |
| 2003/0144581 A1 | 7/2003 | Conn et al. | |
| 2003/0152823 A1 | 8/2003 | Heller | |
| 2003/0176183 A1 | 9/2003 | Drucker et al. | |
| 2003/0188427 A1 | 10/2003 | Say et al. | |
| 2003/0199744 A1 | 10/2003 | Buse et al. | |
| 2003/0208113 A1 | 11/2003 | Mault et al. | |
| 2003/0220552 A1 | 11/2003 | Reghabi et al. | |
| 2004/0061232 A1 | 4/2004 | Shah et al. | |
| 2004/0061234 A1 | 4/2004 | Shah et al. | |
| 2004/0064133 A1 | 4/2004 | Miller et al. | |
| 2004/0064156 A1 | 4/2004 | Shah et al. | |
| 2004/0073095 A1 | 4/2004 | Causey, III et al. | |
| 2004/0074785 A1 | 4/2004 | Holker et al. | |
| 2004/0093167 A1 | 5/2004 | Braig et al. | |
| 2004/0097796 A1 | 5/2004 | Berman et al. | |
| 2004/0102683 A1 | 5/2004 | Khanuja et al. | |
| 2004/0111017 A1 | 6/2004 | Say et al. | |
| 2004/0122353 A1 | 6/2004 | Shahmirian et al. | |
| 2004/0167465 A1 | 8/2004 | Mihai et al. | |
| 2004/0263354 A1 | 12/2004 | Mann et al. | |
| 2005/0038331 A1 | 2/2005 | Silaski et al. | |
| 2005/0038680 A1 | 2/2005 | McMahon et al. | |
| 2005/0060186 A1 | 3/2005 | Blowers et al. | |
| 2005/0154271 A1 | 7/2005 | Rasdal et al. | |
| 2005/0192557 A1 | 9/2005 | Brauker et al. | |
| 2006/0031094 A1 | 2/2006 | Cohen et al. | |
| 2006/0229694 A1 | 10/2006 | Schulman et al. | |
| 2006/0238333 A1 | 10/2006 | Welch et al. | |
| 2006/0293571 A1 | 12/2006 | Bao et al. | |
| 2007/0088521 A1 | 4/2007 | Shmueli et al. | |
| 2007/0123819 A1 | 5/2007 | Mernoe et al. | |
| 2007/0135866 A1 | 6/2007 | Baker et al. | |
| 2008/0154503 A1 | 6/2008 | Wittenber et al. | |
| 2008/0059229 A1 | 8/2008 | Yamada | |
| 2009/0081951 A1 | 3/2009 | Erdmann et al. | |
| 2009/0082635 A1 | 3/2009 | Baldus et al. | |
| 2010/0160861 A1 | 6/2010 | Causey, III et al. | |
| 2010/0268304 A1* | 10/2010 | Matos | A61N 1/37217 607/60 |
| 2011/0154241 A1 | 6/2011 | Skidmore et al. | |
| 2013/0035575 A1* | 2/2013 | Mayou | A61B 5/14532 600/365 |
| 2013/0066819 A1* | 3/2013 | Nice | G06Q 30/0255 706/14 |
| 2013/0171938 A1 | 7/2013 | Mears et al. | |
| 2013/0338630 A1* | 12/2013 | Agrawal | A61M 5/1723 604/504 |
| 2014/0046940 A1 | 2/2014 | Thomson et al. | |
| 2014/0300512 A1* | 10/2014 | Steinhardt | G01D 1/00 342/357.32 |
| 2015/0057634 A1 | 2/2015 | Mastrototaro et al. | |
| 2015/0057807 A1 | 2/2015 | Mastrototaro et al. | |
| 2015/0227708 A1 | 8/2015 | Jung | |
| 2016/0067404 A1 | 3/2016 | Istoc et al. | |
| 2016/0098539 A1* | 4/2016 | Zamanakos | G16H 10/40 705/3 |
| 2017/0106144 A1 | 4/2017 | Kasamanian et al. | |
| 2017/0364660 A1 | 12/2017 | Vigersky et al. | |
| 2019/0009024 A1 | 1/2019 | Morawiec et al. | |
| 2019/0066831 A1 | 2/2019 | Mairs et al. | |
| 2020/0135311 A1 | 4/2020 | Mairs | |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 1996/20745 | 7/1996 |
| WO | WO 1996/36389 | 11/1996 |
| WO | WO 1996/37246 A1 | 11/1996 |
| WO | WO 1997/21456 A1 | 6/1997 |
| WO | WO 1998/20439 A1 | 5/1998 |
| WO | WO 1998/24358 A2 | 6/1998 |
| WO | WO 1998/42407 A1 | 10/1998 |
| WO | WO 1998/49659 A2 | 11/1998 |
| WO | WO 1998/59487 A1 | 12/1998 |
| WO | WO 1999/08183 A1 | 2/1999 |
| WO | WO 1999/10801 A1 | 3/1999 |
| WO | WO 1999/18532 A1 | 4/1999 |
| WO | WO 1999/22236 A1 | 5/1999 |
| WO | WO 2000/10628 A2 | 3/2000 |
| WO | WO 2000/19887 A1 | 4/2000 |
| WO | WO 2000/48112 A2 | 8/2000 |
| WO | WO 2002/058537 A2 | 8/2002 |
| WO | WO 2003/001329 A2 | 1/2003 |
| WO | WO 2003/094090 A2 | 11/2003 |
| WO | WO 2005/065538 A2 | 7/2005 |

OTHER PUBLICATIONS (Intensive Diabetes Management, 1995). Insulin Infusion Pump Therapy. pp. 66-78. (Applicant points out, in accordance with MPEP 609.04(a), that the year of publication, 1995, is sufficiently earlier than the effective U.S. filing date, so that the particular month of publication is not in issue).

PCT Search Report (PCT/US02/03299, dated Oct. 31, 2002, Medtronic Minimed, Inc.

(Medtronic MiniMed, 2002). Medtronic MiniMed Meal Bolus Calculator and Correction Bolus Calculator. International Version. (Applicant points out, in accordance with MPEP 609.04(a), that the year of publication, 2002, is sufficiently earlier than the effective U.S. filing date, so that the particular month of publication is not in issue).

(Medtronic MiniMed, 2002). The 508 Insulin Pump A Tradition of Excellence. (Applicant points out, in accordance with MPEP 609. 04(a), that the year of publication, 2002, is sufficiently earlier than the effective U.S. filing date, so that the particular month of publication is not in issue).

(MiniMed Inc., 1999). Insulin Pump Comparison / Pump Therapy Will Change Your Life. (Applicant points out, in accordance with MPEP 609.04(a), that the year of publication, 1999, is sufficiently earlierthan the effective U.S. filing date, so that the particular month of publication is not in issue).

(MiniMed Inc., 1999). MiniMed 508 Flipchart Guide to Insulin Pump Therapy. (Applicant points out, in accordance with MPEP 609.04(a), that the year of publication, 1999, is sufficiently earlier than the effective U.S. filing date, so that the particular month of publication is not in issue).

(MiniMed Inc., 2000). MiniMed® Now [I] Can Meal Bolus Calculator / MiniMed® Now [I] Can Correction Bolus Calculator. (Applicant points out, in accordance with MPEP 609.04(a), that the year of publication, 2000, is sufficiently earlier than the effective U.S. filing date, so that the particular month of publication is not in issue).

(MiniMed Inc., 2000). Now [I] Can MiniMed Diabetes Management. (Applicant points out, in accordance with MPEP 609.04(a), that the year of publication, 2000, is sufficiently earlier than the effective U.S. filing date, so that the particular month of publication is not in issue).

(56) References Cited

OTHER PUBLICATIONS (MiniMed Inc., 2000). Now [I] Can MiniMed Pump Therapy. (Applicant points out, in accordance with MPEP 609.04(a), that the year of publication, 2000, is sufficiently earlier than the effective U.S. filing date, so that the particular month of publication is not in issue).
(MiniMed International, 1998). MiniMed 507C Insulin Pump For those who appreciate the difference. (Applicant points out, in accordance with MPEP 609.04(a), that the year of publication, 1998, is sufficiently earlier than the effective U.S. filing date, so that the particular month of publication is not in issue).
(MiniMed Technologies, 1994). MiniMed 506 Insulin Pump User's Guide. (Applicant points out, in accordance with MPEP 609.04(a), that the year of publication, 1994, is sufficiently earlier than the effective U.S. filing date, so that the particular month of publication is not in issue).
(MiniMed Technologies, 1994). MiniMed™ Dosage Calculator Initial Meal Bolus Guidelines / MiniMed™ Dosage Calculator Initial Basal Rate Guidelines Percentage Method. 4 pages. (Applicant points out, in accordance with MPEP 609.04(a), that the year of publication, 1994, is sufficiently earlier than the effective U.S. filing date, so that the particular month of publication is not in issue).
(MiniMed, 1996). FAQ: The Practical Things . . . pp. 1-4. Retrieved on Sep. 16, 2003 from the World Wide Web: http:/lweb.archive.org/web/19961111 054546/www.minimed.com/files/faq_pract.htm.
(MiniMed, 1996). MiniMed™ 507 Insulin Pump User's Guide. (Applicant points out, in accordance with MPEP 609.04(a), that the year of publication, 1996, is sufficiently earlier than the effective U.S. filing date, so that the particular month of publication is not in issue).
(MiniMed, 1996). The MiniMed 506. 7 pages. Retrieved on Sep. 16, 2003 from the World Wide Web: h!tp://web.archive.org/web/19961111 054527/www.minimed.com/files/506_pic.htm,.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1997). MiniMed™ 507 Insulin Pump User's Guide. (Applicant points out, in accordance with MPEP 609.04(a), that the year of publication, 1997, is sufficiently earlier than the effective U.S. filing date, so that the particular month of publication is not in issue).
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed, 1998). MiniMed 507C Insulin Pump User's Guide. (Applicant points out, in accordance with MPEP 609.04(a), that the year of publication, 1998, is sufficiently earlier than the effective U.S. filing date, so that the particular month of publication is not in issue).
(MiniMed, 2000). MiniMed® 508 User's Guide. (Applicant points out, in accordance with MPEP 609.04(a), that the year of publication, 2000, is sufficiently earlier than the effective U.S. filing date, so that the particular month of publication is not in issue).
Abel et al., "Experience with an implantable glucose sensor as a prerequisite of an artificial beta cell," Biomed. Biochim. Acta 43 (1984) 5, pp. 577-584. (Applicant points out, in accordance with MPEP 609.04(a), that the year of publication, 1984, is sufficiently earlier than the effective U.S. filing date, so that the particular month of publication is not in issue).
Bindra et al., "Design and in Vitro Studies of a Needle-Type Glucose Sensor for a Subcutaneous Monitoring," American Chemistry Society, vol. 63, No. 17, Sep. 1991, 63, pp. 1692-1696.
Bode et al., "Reduction in Severe Hypoglycemia with Long-Term Continuous Subcutaneous Insulin Infusion in Type I Diabetes," Diabetes Care, vol. 19, No. 4, Apr. 1996, pp. 324-327.
Boguslavsky et al., "Applications of redox polymers in biosensors," Sold State Ionics, vol. 60, Mar. 1993, pp. 189-197.
Boland E (Jan. 1998), Teens Pumping it Up! Insulin Pump Therapy Guide for Adolescents. 2nd Edition.

Brackenridge B P (1992). Carbohydrate Gram Counting A Key to Accurate Mealtime Boluses in Intensive Diabetes Therapy. Practical Diabetology, vol. 11, No. 2, pp. 22-28. (Applicant points out, in accordance with MPEP 609.04(a), that the year of publication, 1991, is sufficiently earlier than the effective U.S. filing date, so that the particular month of publication is not in issue).
Brackenridge, B P et al. (1995). Counting Carbohydrates How to Zero in on Good Control. MiniMed Technologies Inc. (Applicant points out, in accordance with MPEP 609.04(a), that the year of publication, 1995, is sufficiently earlier than the effective U.S. filing date, so that the particular month of publication is not in issue).
Disetronic H-TRON® plus Quick Start Manual. (no date).
Disetronic H-TRON® plus Reference Manual. (No. date).
Disetronic My Choice H-TRONplus Insulin Pump Reference Manual. (no date).
Disetronic My Choice™ D-TRON™ Insulin Pump Reference Manual. (no date).
Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138. (Applicant points out, in accordance with MPEP 609.04(a), that the year of publication, 1994, is sufficiently earlier than the effective U.S. filing date, so that the particular month of publication is not in issue).
Geise et al., "Electropolymerized 1,3-diaminobenzene for the construction of a 1,1'-dimethylferrocene mediated glucose biosensor," Analytica Chimica Acta, vol. 281, No. 3, Sep. 1993, pp. 467-473.
Gernet et al., "A Planar Glucose Enzyme Electrode," Sensors and Actuators, vol. 17, May 1989, pp. 537-540.
Gernet et al., "Fabrication and Characterization of a Planar Electromechanical Cell and its Application as a Glucose Sensor," Sensors and Actuators, vol. 18, Jun. 1989, pp. 59-70.
Gorton et al., "Amperometric Biosensors Based on an Apparent Direct Electron Transfer Between Electrodes and Immobilized Peroxdiases," Analyst, Aug. 1991, vol. 117, pp. 1235-1241.
Gorton, L., et al., "Amperometric Glucose Sensors Based on Immobilized Glucose-Oxidizing Enzymes and Chemically Modified Electrodes," Analytica Chimica Acta, vol. 249, 1991, pp. 43-54. (Applicant points out, in accordance with MPEP 609.04(a), that the year of publication, 1991, is sufficiently earlier than the effective U.S. filing date, so that the particular month of publication is not in issue).
Gough et al., "Two-Dimensional Enzyme Electrode Sensor for Glucose," Analytical Chemistry, vol. 57, No. 12, Oct. 1985, pp. 2351-2357.
Gregg, Brian A., et al., "Cross-Linked Redox Gels Containing Glucose Oxidase for Amperometric Biosensor Applications," Analytical Chemistry, vol. 62, No. 3, Feb. 1990, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, Jul. 1991, pp. 5970-5975.
Hash Iguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Ace. Chem. Res., vol. 23, No. 5, May 1990, pp. 128-134.
Hirsch et al., "Intensive Insulin Therapy for Treatment of Type I Diabetes," Diabetes Care, vol. 13, No. 12, Dec. 1990, pp. 1265-1283.
Jobst, Gerhard, et al., "Thin-Film Microbiosensors forGlucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714. (Applicant points out, in accordance with MPEP 609.04(a), that the year of publication, 1992, is sufficiently earlier than the effective U.S. filing date, so that the particular month of publication is not in issue).

(56) References Cited

OTHER PUBLICATIONS

Jonsson, G., et al., "An Electromechanical Sensor for Hydrogen Peroxide Based on Peroxidase Adsorbed on a Spectrographic Graphite Electrode," Electroanalysis, vol. 1, No. 5, Sep. 1989, pp. 465-468.

Kanapieniene, J. J., et al., "Miniature Glucose Biosensor with Extended Linearity," Sensors and Actuators, B: Chemical, vol. 10, No. 1, Dec. 1992, pp. 37-40.

Kawamori, Ryuzo, et al., "Perfect Normalization of Excessive Glucagon Responses to lntraveneous Arginine in Human Diabetes Mellitus With the Artificial Beta-Cell," Diabetes vol. 29, Sep. 1980, pp. 762-765.

Kimura, J., et al., "An Immobilized Enzyme Membrane Fabrication Method," Biosensors, vol. 4, No. 1, 1988, pp. 41-52. (Applicant points out, in accordance with MPEP 609.04(a), that the year of publication, 1988, is sufficiently earlier than the effective U.S. filing date, so that the particular month of publication is not in issue).

Koudelka, M., et al., "In-vivo Behaviour of Hypodermically Implanted Microfabricated Glucose Sensors," Biosensors & Bioelectronics, vol. 6, 1991, pp. 31-36. (Applicant points out, in accordance with MPEP 609.04(a), that the year of publication, 1991, is sufficiently earlier than the effective U.S. filing date, so that the particular month of publication is not in issue).

Koudelka, M., et al., "Planar Amperometric Enzyme-Based Glucose Microelectrode," Sensors & Actuators, vol. 18, Jun. 1989, pp. 157-165.

Kulkarni K et al. (Jan. 1999). Carbohydrate Counting A Primer for Insulin Pump Users to Zero in on Good Control. MiniMed Inc.

Marcus et al., "Insulin Pump Therapy Acceptable Alternative to Injection Therapy," Postgraduate Medicine, vol. 99, No. 3, Mar. 1996, pp. 125-142.

Mastrototaro et al., "An electroenzymatic glucose sensor fabricated on a flexible substrate," Sensors & Actuators, B: Chemical; vol. 5, Aug. 1991, pp. 139-144.

Mastrototaro et al., "An Electroenzymatic Sensor Capable of 72 Hour Continuous Monitoring of Subcutaneous Glucose," 14th Annual International Diabetes Federation Congress, Washington D.C., Jun. 23-28, 1991.

McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.

Monroe, D., "Novel Implantable Glucose Sensors," ACL, Dec. 1989, pp. 8-16.

Morff, Robert J., et al., "Microfabrication of Reproducible, Economical, Electroenzymatic Glucose Sensors," Annual International Conference of the IEEE Engineering in Medicine and Biology Society, vol. 12, No. 2, Nov. 1990, pp. 483-484.

Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.

Nakamoto, S., et al., "A Lift-Off Method for Patterning Enzyme-Immobilized Membranes in Multi-Biosensors," Sensors and Actuators, vol. 13, Feb. 1988, pp. 165-172.

Nishida, Kenro, et al., "Clinical applications of the wearable artificial endocrine pancreas with the newly designed needle-type glucose sensor," Elsevier Sciences B.V., 1994, pp. 353-358. (Applicant points out, in accordance with MPEP 609.04(a), that the year of publication, 1994, is sufficiently earlier than the effective U.S. filing date, so that the particular month of publication is not in issue).

Nishida, Kenro, et al., "Development of a ferrocene-mediated needle-type glucose sensor covered with newly designed biocompatible membrane, 2-methacryloyloxyethyl phosphorylcholine-co-n-butyl methacrylate," Medical Progress Through Technology, vol. 21, Apr. 1995, pp. 91-103.

Poitout, V., et al., "A glucose monitoring system for on line estimation in man of blood glucose concentration using a miniaturized glucose sensor implanted in the subcutaneous tissue and a wearable control unit," Diabetologia, vol. 36, Jul. 1991, pp. 658-663.

Reach, G., "A Method for Evaluating in vivo the Functional Characteristics of Glucose Sensors," Biosensors, vol. 2, 1986, pp. 211-220. (Applicant points out, in accordance with MPEP 609.04(a), that the year of publication, 1986, is sufficiently earlier than the effective U.S. filing date, so that the particular month of publication is not in issue).

Reed, J., "Living with Diabetes," Voice of the Diabetic, vol. 11, No. 3, Summer Edition 1996, pp. 1-38. (Applicant points out, in accordance with MPEP 609.04(a), that the year of publication, 1996, is sufficiently earlier than the effective U.S. filing date, so that the particular month of publication is not in issue).

Shaw, G. W., et al., "In vitro testing of a simply constructed, highly stable glucose sensor suitable for implantation in diabetic patients," Biosensors & Bioelectronics, vol. 6, 1991, pp. 401-406. (Applicant points out, in accordance with MPEP 609.04(a), that the year of publication, 1991, is sufficiently earlier than the effective U.S. filing date, so that the particular month of publication is not in issue).

Shichiri, M., "A Needle-Type Glucose Sensor—A Valuable Tool Not Only For a Self-Blood Glucose Monitoring but for a Wearable Artificial Pancreas," Life Support Systems Proceedings, XI Annual Meeting ESAO, Alpbach-lnnsbruck, Austria, Sep. 1984, pp. 7-9.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20. (Applicant points out, in accordance with MPEP 609.04(a), that the year of publication, 1988, is sufficiently earlier than the effective U.S. filing date, so that the particular month of publication is not in issue).

Shichiri, M., et al., "Membrane design for extending the long-life of an implantable glucose sensor," Diab. Nutr. Metab., vol. 2, No. 4, 1989, pp. 309-313. (Applicant points out, in accordance with MPEP 609.04(a), that the year of publication, 1989, is sufficiently earlier than the effective U.S. filing date, so that the particular month of publication is not in issue).

Shichiri, Motoaki, et al., "An artificial endocrine pancreas—problems awaiting solution for long-term clinical applications of a glucose sensor," Frontiers Med. Bioi. Engng., 1991, vol. 3, No. 4, pp. 283-292. (Applicant points out, in accordance with MPEP 609.04(a), that the year of publication, 1991, is sufficiently earlier than the effective U.S. filing date, so that the particular month of publication is not in issue).

Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

Shichiri, Motoaki, et al., "Glycaemic Control in a Pancreatectomized Dogs with a Wearable Artificial Endocrine Pancreas," Diabetologia, vol. 24, Mar. 1983, pp. 179-184.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn, Sep. 1984, vol. 26, pp. 359-370.

Shichiri, Motoaki, et al., "Wearable Artificial Endocrine Pancreas with Needle-Type Glucose Sensor," The Lancet, Nov. 20, 1982, pp. 1129-1131.

Shinkai, Seiji, "Molecular Recognition of Mono- and Di-saccharides by Phenylboronic Acids in Solvent Extraction and as a Monolayer," J. Chem. Soc., Chem. Commun., vol. 15, Aug. 1991, pp. 1039-1041.

(56) References Cited

OTHER PUBLICATIONS

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Skyler J S (1989). Continuous Subcutaneous Insulin Infusion [CSII] With External Devices: Current Status. Update in Drug Delivery Systems, Chapter 13, pp. 163-183. Futura Publishing Company. (Applicant points out, in accordance with MPEP 609.04(a), that the year of publication, 1989, is sufficiently earlier than the effective U.S. filing date, so that the particular month of publication is not in issue).

Skyler J S et al. (1995). The Insulin Pump Therapy Book Insights from the Experts. MiniMed• Technologies. (Applicant points out, in accordance with MPEP 609.04(a), that the year of publication, 1995, is sufficiently earlier than the effective U.S. filing date, so that the particular month of publication is not in issue).

Sternberg, Robert, et al., "Study and Development of Multilayer Needle-type Enzyme-based Glucose Microsensors," Biosensors, vol. 4, Dec. 1988, pp. 27-40.

Strowig S M, "Initiation and Management of Insulin Pump Therapy," The Diabetes Educator, vol. 19, No. 1, Feb. 1993, pp. 50-60.

Tamiya, E., et al., "Micro Glucose Sensors using Electron Mediators Immobilized on a Polypyrrole-Modified Electrode," Sensors and Actuators, vol. 18, Jul. 1989, pp. 297-307.

Tsukagoshi, Kazuhiko, et al., "Specific Complexation with Mono- and Disaccharides that can be Detected by Circular Dichroism," J. Org. Chem., vol. 56, Jun. 1991, pp. 4089-4091.

Ubran, G., et al., "Miniaturized thin-film biosensors using covalently immobilized glucose oxidase," Biosensors & Bioelectronics, vol. 6, 1991, pp. 555-562. (Applicant points out, in accordance with MPEP 609.04(a), that the year of publication, 1991, is sufficiently earlier than the effective U.S. filing date, so that the particular month of publication is not in issue).

Urban, G., et al., "Miniaturized multi-enzyme biosensors integrated with pH sensors on flexible polymer carriers for in vivo applications," Biosensors & Bioelectronics, vol. 7, 1992, pp. 733-739. (Applicant points out, in accordance with MPEP 609.04(a), that the year of publication, 1992, is sufficiently earlierthan the effective U.S. filing date, so that the particular month of publication is not in issue).

Velho, G., et al., "In vivo calibration of a subcutaneous glucose sensor for determination of subcutaneous glucose kinetics," Diab. Nutr. Metab., vol. 3, 1988, pp. 227-233. (Applicant points out, in accordance with MPEP 609.04(a), that the year of publication, 1988, is sufficiently earlier than the effective U.S. filing date, so that the particular month of publication is not in issue).

Walsh J, et al. (1989). Pumping Insulin: The Art of Using an Insulin Pump. Published by MiniMed• Technologies. (Applicant points out, in accordance with MPEP 609.04(a), that the year of publication, 1989, is sufficiently earlier than the effective U.S. filing date, so that the particular month of publication is not in issue).

Wang, Joseph, et al., "Needle-Type Dual Microsensor for the Simultaneous Monitoring of Glucose and Insulin," Analytical Chemistry, vol. 73, Feb. 2001, pp. 844-847.

Yamasaki, Yoshimitsu, et al., "Direct Measurement of Whole Blood Glucose by a Needle-Type Sensor," Clinics Chimica Acta, vol. 180, Mar. 1989, pp. 93-98.

Yokoyama, K., "Integrated Biosensor for Glucose and Galactose," Analytica Chimica Acta, vol. 218, 1989, pp. 137-142. (Applicant points out, in accordance with MPEP 609.04(a), that the year of publication, 1989, is sufficiently earlier than the effective U.S. filing date, so that the particular month of publication is not in issue).

\* cited by examiner

Pattern Snapshot for Sample M. Patient
Sep 28 - Oct 4, 2009
(7 days)                    Medtronic iPro2 Recorder    #123456

Avg SG: 158 mg/dL                  Time in range: 22% Above 140 mg/dL
Estimated A1C(1): 5.7% calculated from SG values    66% in target range
                                   12% Below 70 mg/dL

OBSERVED PATTERNS & SOME POSSIBLE CAUSES(2)

Patient current therapy:
Metformin, 500 mg X 2
Basal insulin PM

① Variable SG with Low SG Overnight 9:00 PM - 6:00 AM

Consider:
· Reducing evening basal insulin dose by 10%-20%
· Adding bedtime snack ② Variable SG with Low SG Post-lunch 11:00 AM - 3:00 PM ③ Variable SG with Low SG Post-lunch 11:00 AM - 3:00 PM The medications or therapy/treatment actions listed below are based on establish practice guidelines and are provided only as examples of common responses, decisions, and/or orders made by healthcare professionals for patients who had a similar baseline status and glucose results. Because all patients have varying health issues, medical histories, previous medication uses, renal function, intolerances, and/or drug -- practitioner should not consider the medications or therapy/treatment actions listed below as recommendations or guidance for any particular patient. Again, these are only examples of common therapy decisions in patients with similar baseline status and glucose results assuming the patient is taking his/her medication as prescribed <u>Each healthcare professional or practitioner should exercise independent judgment and decision making for their own individual patients, and not rely on the data below for making therapy adjustments or recommendations. Please confirm the medications and their doses on the report before deciding on any change in therapy.</u>

Therapy recommendations are meant to supplement any advice about diet and exercise that you give to your patients.

| 12am 1 2 3am | 4 5 6am 7 | 8 9am 10 | 11 12pm 1 | 2 3pm 4 | 5 6pm 7 | 8 9pm 10 | 11 12am |
|---|---|---|---|---|---|---|---|
| Avg 89 mg/dL | 87 mg/dL | 131 mg/dL | 123 mg/dL | 144 mg/dL | 98 mg/dL | 137 mg/dL | 110 mg/dL |

Mon Sep 28  Tue Sep 29  Wed Sep 30  Thur Oct 1  Fri Oct 2  Sat Oct 3  Sun Oct 4  AVG  Target Meal Marker (1) Estimated A1C does not replace Lab measurement and is calculated from limited SG data.

FIG. 16

MEDICAL DEVICES AND RELATED EVENT PATTERN PRESENTATION METHODS

CROSS-REFERENCE TO RELATED APPLICATION(S)

This application is a continuation-in-part of U.S. patent application Ser. No. 16/058,736, filed Aug. 8, 2018, which is a continuation-in-part of U.S. patent application Ser. No. 15/693,238, filed Aug. 31, 2017, which is a continuation-in-part of U.S. patent application Ser. No. 15/132,126, filed Apr. 18, 2016, which claims the benefit of U.S. Provisional Patent Application Ser. No. 62/243,416, filed Oct. 19, 2015, the entire contents of which are incorporated by reference herein.

This application is also related to U.S. patent application Ser. No. 16/175,774, filed concurrently herewith.

TECHNICAL FIELD

Embodiments of the subject matter described herein relate generally to medical devices, and more particularly, embodiments of the subject matter relate to generating reports for therapy management based on measurement data pertaining to preceding operation of a fluid infusion device.

BACKGROUND

Infusion pump devices and systems are relatively well known in the medical arts, for use in delivering or dispensing an agent, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user. Use of infusion pump therapy has been increasing, especially for delivering insulin for diabetics.

Control schemes have been developed that allow insulin infusion pumps to monitor and regulate a user's blood glucose level in a substantially continuous and autonomous manner. However, regulating blood glucose level is still complicated by variations in the response time for the type of insulin being used along with variations in a user's individual insulin response and daily activities (e.g., exercise, carbohydrate consumption, bolus administration, and the like). Additionally, manually-initiated deliveries of insulin prior to or contemporaneously with consuming a meal (e.g., a meal bolus or correction bolus) also influence the overall glucose regulation, along with various patient-specific ratios, factors, or other control parameters.

Physicians have recognized that continuous monitoring provides a greater understanding of a diabetic's condition. That said, there is also a burden imposed on physicians and other healthcare providers to adapt to continuous monitoring and incorporate the amount of data obtained therefrom in a manner that allows for a physician to meaningfully assist and improve patient outcomes. While automated reports can be generated based on the data, they can be difficult to parse or appear overwhelming to physicians, which given the limited time available to physicians, may discourage adoption and incorporation of continuous monitoring as part of their practice. Accordingly, there is a need to generate and provide information in a usable form that can be quickly and intuitively interpreted and applied.

BRIEF SUMMARY

Medical devices and related systems and operating methods are provided. An embodiment of a method of operating a medical device to deliver medication to a body of a patient, such as an infusion device delivering fluid to the body of the patient, is provided. The method involves identifying, based on measurement values for a physiological condition in the body of the patient, a plurality of event patterns within respective ones of a plurality of monitoring periods, prioritizing the plurality of event patterns based on one or more prioritization criteria, resulting in a prioritized list of event patterns, filtering the prioritized list based on one or more filtering criteria, resulting in a filtered prioritized list of event patterns, and providing, on a display device, a respective pattern guidance display for each respective event pattern of the filtered prioritized list.

An embodiment of a system including an infusion device and a computing device is also provided. The infusion device is operable to deliver fluid to a body of a patient based on measurement values for a physiological condition in the body of the patient obtained from a sensing arrangement, where the fluid influences the physiological condition. The computing device is communicatively coupled to the infusion device over a network to identify a plurality of event patterns within a plurality of monitoring periods based on the measurement values, prioritize the plurality of event patterns based on one or more prioritization criteria, filter the prioritized list of event patterns based on one or more filtering criteria, and generate a respective pattern guidance display for each respective event pattern of the filtered prioritized list.

An embodiment of a method of presenting information pertaining to operation of an infusion device to deliver insulin to a body of a patient is also provided. The method involves obtaining, by a computing device, historical glucose measurement data for the patient from a database and identifying, by the computing device based on the historical glucose measurement data, a plurality of event patterns within respective ones of a plurality of monitoring periods, wherein each monitoring period of the plurality of monitoring periods corresponds to a different time of day corresponding to a different subset of the historical glucose measurement data. The method continues by the computing device prioritizing the plurality of event patterns based on one or more of an event type associated with respective event patterns of the plurality of event patterns and the respective monitoring period associated with respective event patterns of the plurality of event patterns, filtering the prioritized list based on one or more filtering criteria, and generating a respective pattern guidance display for each respective event pattern of the filtered prioritized list.

In one embodiment, a system includes an infusion device operable to deliver fluid to a body of a patient based on measurement values for a physiological condition in the body of the patient from a sensing arrangement, the fluid influencing the physiological condition and a computing device communicatively coupled to the infusion device over a network to identify a plurality of event patterns within a plurality of monitoring periods based on the measurement values, prioritize the plurality of event patterns based on one or more prioritization criteria, filter the prioritized list of event patterns based on one or more filtering criteria, and generate a respective pattern guidance display for each respective event pattern of the filtered prioritized list, wherein the respective pattern guidance display for at least one respective event pattern of the filtered prioritized list includes a graphical representation of a remedial action.

In another embodiment, a method of presenting information pertaining to operation of an infusion device to deliver insulin to a body of a patient involves obtaining, by a computing device, historical glucose measurement data for the patient from a database, identifying, by the computing device, a plurality of event patterns within respective ones of a plurality of monitoring periods based on the historical glucose measurement data, wherein each monitoring period of the plurality of monitoring periods corresponds to a different time of day corresponding to a different subset of the historical glucose measurement data, prioritizing, by the computing device, the plurality of event patterns based on one or more of an event type associated with respective event patterns of the plurality of event patterns and the respective monitoring period associated with respective event patterns of the plurality of event patterns, resulting in a prioritized list of event patterns, identifying, by the computing device, a remedial action associated with a highest priority event pattern of the prioritized list, and generating, by the computing device, a pattern guidance display for the highest priority event pattern of the prioritized list, wherein the pattern guidance display includes a graphical representation of the remedial action.

In another embodiment, a system is provided that includes a display device having rendered thereon a snapshot graphical user interface display comprising a pattern detection region including a plurality of pattern guidance displays corresponding to a plurality of event patterns detected within a time period corresponding to the snapshot graphical user interface display. The plurality of pattern guidance displays corresponding to the plurality of event patterns are prioritized primarily based on a respective event type of a plurality of event types associated with each respective event pattern of the plurality of event patterns and secondarily based on a respective monitoring period associated with each respective event pattern of the plurality of event patterns, and a highest priority pattern guidance display of the plurality of pattern guidance displays includes graphical indicia of a therapeutic remedial action corresponding to a highest priority event pattern of the plurality of event patterns corresponding to the highest priority pattern guidance display.

In another embodiment, a patient management system includes a medical device to obtain measurement values for a physiological condition in a body of a patient and a computing device communicatively coupled to the medical device over a network to identify a plurality of event patterns within a plurality of monitoring periods based on the measurement values, prioritize the plurality of event patterns based on one or more prioritization criteria, filter the prioritized list of event patterns based on one or more filtering criteria, and generate a snapshot graphical user interface display. The snapshot graphical user interface display includes a graph overlay region and an event detection region below the graph overlay region. The graph overlay region includes a graphical representation of the measurement values with respect to a time of day. The event detection region includes a respective pattern guidance display for each respective event pattern of the filtered prioritized list ordered in a top-down manner according to the respective priority assigned to the respective event pattern within the filtered prioritized list.

In another embodiment, a method of presenting information pertaining to operation of an infusion device to deliver insulin to a body of a patient is provided. The method involves obtaining, by a computing device, historical glucose measurement data for the patient from a database, identifying, by the computing device based on the historical glucose measurement data, a plurality of event patterns within respective ones of a plurality of monitoring periods, wherein each monitoring period of the plurality of monitoring periods corresponds to a different time of day corresponding to a different subset of the historical glucose measurement data, and prioritizing, by the computing device, the plurality of event patterns based on one or more of an event type associated with respective event patterns of the plurality of event patterns and the respective monitoring period associated with respective event patterns of the plurality of event patterns, resulting in a prioritized list of event patterns. The method continues by the computing device filtering the prioritized list based on one or more filtering criteria and generating a snapshot graphical user interface display. The snapshot graphical user interface display includes a graph overlay region comprising a graphical representation of the historical glucose measurement data with respect to a time of day and an event detection region below the graph overlay region. The event detection region includes a respective pattern guidance display for each respective event pattern of the filtered prioritized list, and the plurality of pattern guidance displays are ordered in a top-down from highest priority to lower priorities in accordance with the filtered prioritized list.

In another device, a patient management system includes a display device having rendered thereon a snapshot graphical user interface display including a graph overlay region and an event pattern detection region below the graph overlay region. The graph overlay region includes a graphical representation of historical measurement data for a physiological condition of a patient with respect to a time of day. The event pattern detection region includes a plurality of pattern guidance displays corresponding to a plurality of event patterns detected within a time period corresponding to the snapshot graphical user interface display based on the historical measurement data. The plurality of pattern guidance displays corresponding to the plurality of event patterns are prioritized primarily based on a respective event type of a plurality of event types associated with each respective event pattern of the plurality of event patterns and secondarily based on a respective monitoring period associated with each respective event pattern of the plurality of event patterns. The pattern guidance displays are ordered top-down within the event pattern detection region according to the respective priorities of the respective event patterns associated therewith. A highest priority pattern guidance display of the plurality of pattern guidance displays includes a pattern analysis region identifying one or more potential causes of a highest priority event pattern associated with the highest priority pattern guidance display displayed above a therapy analysis region identifying one or more recommended therapeutic remedial actions pertaining to the highest priority event pattern.

In yet another embodiment, a method of presenting information pertaining to operation of a medical device involves obtaining historical glucose measurement data for a patient from a database, identifying, based on the historical glucose measurement data, a first set of event patterns within respective ones of a plurality of monitoring periods, obtaining an adjusted set of glucose measurement data determined based on the historical glucose measurement data and an uncertainty metric associated with the historical glucose measurement data, identifying, based on the adjusted set of glucose measurement data, a second set of event patterns within respective ones of the plurality of monitoring periods, and generating a graphical user interface display comprising an event detection region based at least in part on the first set and the second set of event patterns.

In another embodiment, a system includes a database to maintain measurement values for a physiological condition in a body of a patient obtained by a medical device and a computing device coupled to the database to identify a first set of event patterns within a plurality of monitoring periods based on the measurement values, identify a second set of event patterns within the plurality of monitoring periods based on an adjusted set of the measurement values determined based on an uncertainty metric associated with the measurement values, determine a list of event patterns for presentation based at least in part on the first and second sets of event patterns, and generate a graphical user interface display including an event detection region. Each monitoring period of the plurality of monitoring periods corresponds to a different time of day corresponding to a different subset of the historical glucose measurement data, and the event detection region comprises a respective pattern guidance display for each respective event pattern of the list.

In another embodiment, a method of presenting information pertaining to operation of a medical device involves obtaining historical glucose measurement data for a patient from a database, identifying, based on the historical glucose measurement data, a first plurality of event patterns within respective ones of a plurality of monitoring periods, determining a respective value for a confidence metric for each respective event pattern of the first plurality of event patterns based at least in part on a detection criterion associated with the respective event pattern, a respective subset of the historical glucose measurement data corresponding to the respective monitoring period of the plurality of monitoring periods associated with the respective event pattern, and an interval estimation metric associated with the historical glucose measurement data, and providing one or more graphical indicia influenced by the confidence metric.

In another embodiment, a system includes a database to maintain measurement values for a physiological condition in a body of a patient obtained by a medical device, and a computing device coupled to the database to identify a first plurality of event patterns within a plurality of monitoring periods based on the measurement values, determine a respective value for a confidence metric for each respective event pattern of the first plurality of event patterns based at least in part on a detection criterion associated with the respective event pattern and an interval estimation metric associated with the measurement values, and provide one or more graphical indicia influenced by the respective values for the confidence metric. Each monitoring period of the plurality of monitoring periods corresponds to a different time of day corresponding to a different subset of the historical glucose measurement data.

In yet another embodiment, a system is provided that includes a display device having rendered thereon a snapshot graphical user interface display comprising a graph overlay region and an event pattern detection region. The graph overlay region includes a graphical representation of historical measurement data for a physiological condition of a patient with respect to a time of day. The event pattern detection region includes a plurality of pattern guidance displays corresponding to a plurality of event patterns detected within a time period corresponding to the snapshot graphical user interface display based on the historical measurement data. Each respective event pattern of the plurality of event patterns corresponds to a respective one of a plurality of monitoring periods, wherein each monitoring period of the plurality of monitoring periods corresponds to a different time of day corresponding to a different subset of the historical glucose measurement data. The plurality of pattern guidance displays correspond to the plurality of event patterns, and the pattern guidance displays are prioritized in accordance with respective values for a confidence metric associated with the respective event patterns.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

FIGS. 14-16 depict exemplary embodiments of snapshot GUI displays that may be presented on a display device associated with a computing device in accordance with one or more embodiments of the recommendation process of FIG. 13;

DETAILED DESCRIPTION

Figure 1:
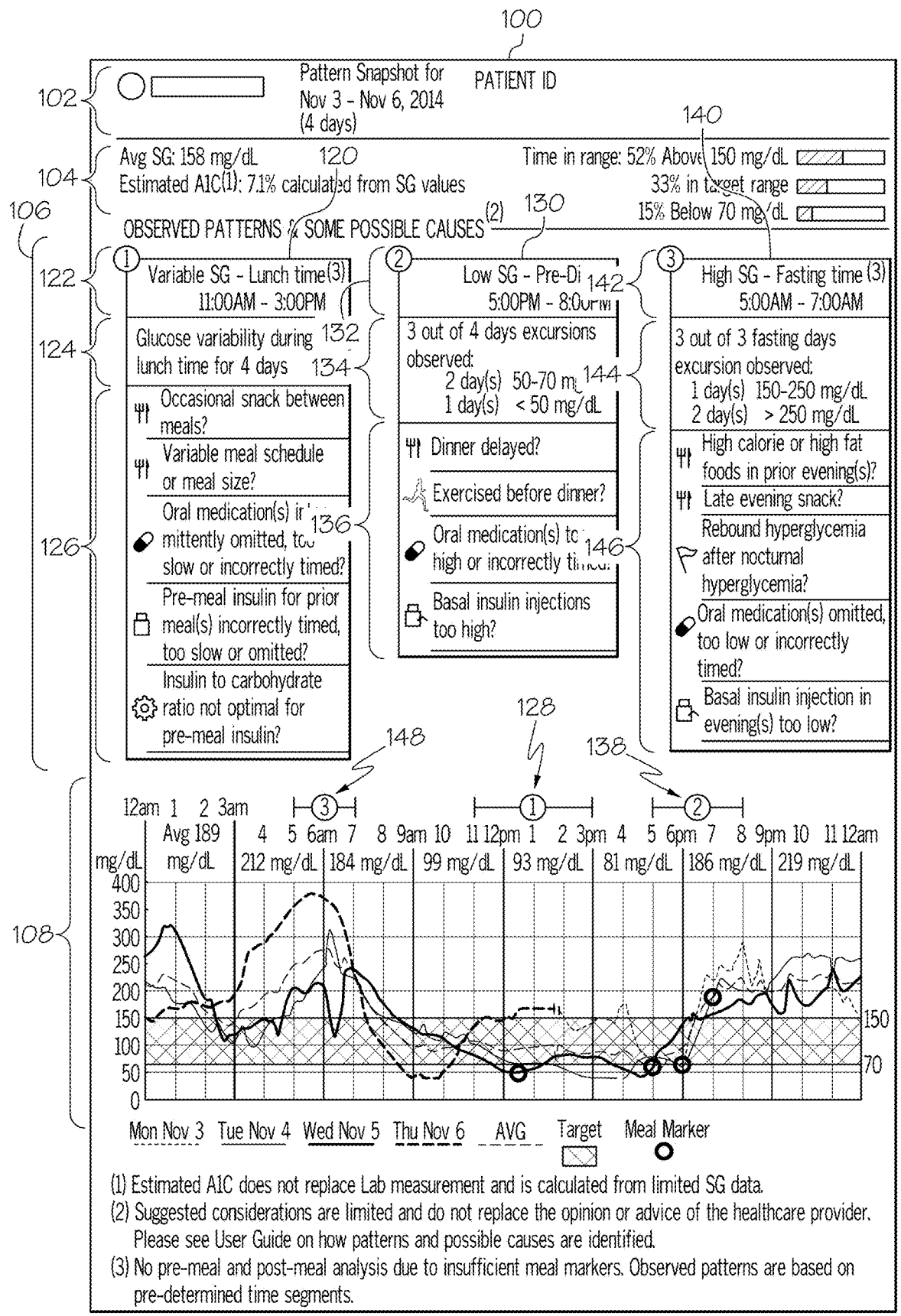
FIG. 1 depicts an exemplary embodiment of a snapshot graphical user interface (GUI) display that may be presented on a display device associated with a computing device in one or more embodiments.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Exemplary embodiments of the subject matter described herein are implemented in conjunction with medical devices, such as portable electronic medical devices. Although many different applications are possible, the following description focuses on embodiments that incorporate a fluid infusion device (or infusion pump) as part of an infusion system deployment. That said, the subject matter may be implemented in an equivalent manner in the context of other medical devices, such as continuous glucose monitoring (CGM) devices, injection pens (e.g., smart injection pens), and the like. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference. That said, the subject matter described herein can be utilized more generally in the context of overall diabetes management or other physiological conditions independent of or without the use of an infusion device or other medical device (e.g., when oral medication is utilized), and the subject matter described herein is not limited to any particular type of medication.

Generally, a fluid infusion device includes a motor or other actuation arrangement that is operable to linearly displace a plunger (or stopper) of a reservoir provided within the fluid infusion device to deliver a dosage of fluid, such as insulin, to the body of a user. Dosage commands that govern operation of the motor may be generated in an automated manner in accordance with the delivery control scheme associated with a particular operating mode, and the dosage commands may be generated in a manner that is influenced by a current (or most recent) measurement of a physiological condition in the body of the user. For example, in a closed-loop operating mode, dosage commands may be generated based on a difference between a current (or most recent) measurement of the interstitial fluid glucose level in the body of the user and a target (or reference) glucose value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin.

Exemplary embodiments of the subject matter described herein generally relate to systems for analyzing and presenting information pertaining to operation of the infusion device delivering fluid to a body of a user. In exemplary embodiments, a snapshot graphical user interface (GUI) display is presented on an electronic device, and the snapshot GUI display includes or otherwise provides graphical representations or other graphical indicia of various aspects of the physiological condition in the body of the user that is regulated or otherwise influenced by the fluid delivered by the infusion device. For example, the snapshot GUI display may include graphical representations of a diabetic patient's glucose levels along with other indicia pertaining to the glycemic control achieved by the infusion device delivering insulin to the patient.

In exemplary embodiments described herein, the snapshot GUI display includes a pattern detection region that includes graphical indicia of event pattern(s) detected or otherwise identified based on measurement data for the user's physiological condition. The detected event pattern(s) are prioritized based on one or more prioritization criteria and filtered based on one or more filtering criteria, resulting in a filtered prioritized list of detected event patterns that includes only those event patterns to be presented to the user. For each retained event pattern in the filtered prioritized list, a respective pattern guidance display is generated or otherwise provided which includes information pertaining to that respective event pattern, such as, for example, an identification of the type of event pattern, an indication of a period of time associated with the event pattern, one or more metric(s) indicative of the frequency and/or severity of the event, and the like. Additionally, the pattern guidance display includes graphical indicia of one or more potential causes of event pattern, which, in turn may be utilized by the patient, the patient's doctor or other health care provider, or another individual in assessing the efficacy of the regulation achieved by the infusion device and identifying potential actions that may improve the quality of control achieved by the infusion device. As described in greater detail below in the context of FIGS. 13-16, in one or more embodiments, information pertaining to a displayed event pattern may be analyzed in connection with other therapeutic or physiological information associated with the patient to identify a remedial action that could potentially resolve, mitigate, correct or otherwise address the event pattern (e.g., adding a new medication, adjusting dosages or delivery rates, and the like) and provide corresponding graphical indicia of the remedial action in connection with the displayed event pattern.

Event Pattern Presentation

FIG. 1 depicts an exemplary embodiment of a snapshot GUI display 100 or report that may be presented on a display device associated with an electronic device, such as, for example, a computing device, a portable medical device, a sensor device, or the like. The snapshot GUI display 100 includes a plurality of regions 102, 104, 106, 108 that present information pertaining to past operation of a fluid infusion device that delivers insulin to regulate the glucose level of a diabetic patient. A header region 102 is presented at the top of the snapshot GUI display 100 and includes a graphical representation of a preceding time period of operation (e.g., November 3-November 6) associated with the snapshot GUI display 100 for which information is presented in the below regions 104, 106, 108.

A graph overlay region 108 is presented at the bottom of the snapshot GUI display 100 that includes graphical representations of historical measurement data for the patient's glucose level over the snapshot time period with respect to time. In this regard, the graph overlay region 108 may include a line graph including a line associated with each day within the snapshot time period that depicts the patient's sensor glucose measurements values from that day with respect to time of day. Additionally, the graph overlay region 108 may include a line representative of the average of the patient's sensor glucose measurements across the different days within the snapshot time period with respect to time of day. The illustrated graph overlay region 108 also includes a visually distinguishable overlay region that indicates a target range for the patient's sensor glucose measurement values. In exemplary embodiments, the graphical representation of the measurements for each different day or date depicted on the graph overlay region 108 is rendered with a unique color or other visually distinguishable characteristic relative to the graphical representations corresponding to other days or dates, with the meal markers on that respective day or date also being rendered in the same color or visually distinguishable characteristic and placed on the line corresponding to that respective day or date. The illustrated graph overlay region 108 also includes graphical representations of multiday averages of the measurement data for different periods or times of day, for example, every three-hour segment of the day (e.g., the average sensor glucose measurement for the 12 AM-3 AM time period across the dates encompassed by the snapshot time period is 189 mg/dL).

A performance metric region 104 is presented below the header region 102 and includes graphical representations or other indicia of the values for various performance metrics calculated based on the historical measurement data for the patient's glucose level over the time period associated with the snapshot GUI display 100. The performance metrics depicted in the performance metric region 104 may include an average sensor glucose measurement value for the patient calculated based on the sensor glucose measurement values over the snapshot time period, an estimated A1C level calculated based on the sensor glucose measurement values over the snapshot time period, and estimated percentages of the snapshot time period during which durations the sensor glucose measurement values were above an upper glucose threshold value (e.g., 150 mg/dL), below a lower glucose threshold value (e.g., 70 mg/dL), or between the upper and lower glucose threshold values. In this regard, the upper and lower glucose threshold values may define a target region for the patient's glucose level during the snapshot time period. The threshold values defining the target region may be configurable by a user, for example, to vary one or more aspects of the report, or alternatively, to influence the glucose regulation provided by the infusion device while also influencing one or more aspects of the report. The graphical indicia for performance metrics presented in the performance metric region 104 may include textual representations of the respective performance metric values along with charts, graphs, or other visualizations of respective performance metric values. For example, the illustrated embodiment of the performance metric region 104 includes progress bar GUI elements that depict the respective percentages of the snapshot time period during which the patient's sensor glucose measurement values were above, below, or between upper and lower glucose threshold values.

Still referring to FIG. 1, the snapshot GUI display 100 also includes a pattern detection region 106 presented between the performance metric region 104 and the graph overlay region 108. The pattern detection region 106 includes a plurality of pattern guidance displays 120, 130, 140, where each pattern guidance display 120, 130, 140 corresponds to a respective pattern of events identified during the snapshot time period based on the patient's sensor glucose measurement values for the snapshot time period. In this regard, the historical sensor glucose measurement values are analyzed for different monitoring periods within the snapshot time period. As described in greater detail below in the context of FIG. 3, based on the subset of sensor glucose measurement values associated with times of day within a respective monitoring period, a pattern of one or more events is detected or otherwise identified within that monitoring period, such as, for example, a glucose variability event, a high glucose (or hyperglycemic) event, or a low glucose (or hypoglycemic) event. After identifying a plurality of event patterns within respective monitoring periods, the identified event patterns are prioritized and filtered to limit the number of event patterns for display. For example, in one embodiment, the detected event patterns are prioritized primarily based on event type (e.g., from most significant to least significant) and secondarily based on the monitoring period associated with the respective event pattern, and then filtered to first remove lower priority event patterns having the same associated monitoring period as a higher priority event pattern, and then secondarily remove remaining event patterns above a display threshold that limits the number of displayed event patterns. In this regard, FIG. 1 depicts an embodiment where the variability event type is prioritized above the hypoglycemic event type and the hyperglycemic event type in that order, and with the display threshold being equal to three to limit the number of pattern guidance displays within the pattern detection region 106 to three.

As described in greater detail below in the context of FIG. 4, for each remaining event pattern of the filtered prioritized list, a pattern guidance display 120, 130, 140 is generated that includes a header region 122, 132, 142 that includes graphical indicia of the event type and the monitoring period associated with the detected pattern, a summary region 124, 134, 144 that includes graphical indicia of the number, frequency, severity, or other characteristics of the events associated with the detected pattern, and an analysis region 126, 136, 146 that includes graphical indicia of potential causes or remedial actions for the detected events. It should be noted that the graphical indicia of potential causes or remedial actions may also be prioritized or ordered according to their respective clinical relevance. Additionally, in exemplary embodiments, graphical indicia 128, 138, 148 of the detected event patterns are presented within the graph overly region 108 in a manner that establishes an association between the detected event pattern, the time of day associated with its corresponding monitoring period, and its relative priority level. Thus, the graphical indicia 128, 138, 148 facilitate establishing an association between a respective subset of the historical measurement data presented within the graph overlay region 108 and a corresponding event pattern detected based on that subset of historical measurement data. For example, in the illustrated embodiment of FIG. 1, a marker 128 is presented overlying the graph overlay region 108 that includes an identifier that indicates the detected event pattern the marker 128 corresponds to (e.g., number 1 to indicate the highest priority event pattern 120), and the marker 128 has a width or other dimension that encompasses or otherwise corresponds to the subset of the sensor glucose measurement values associated with the time of day corresponding to the monitoring period associated with the detected event pattern (e.g., the lunch time period).

Figure 2:
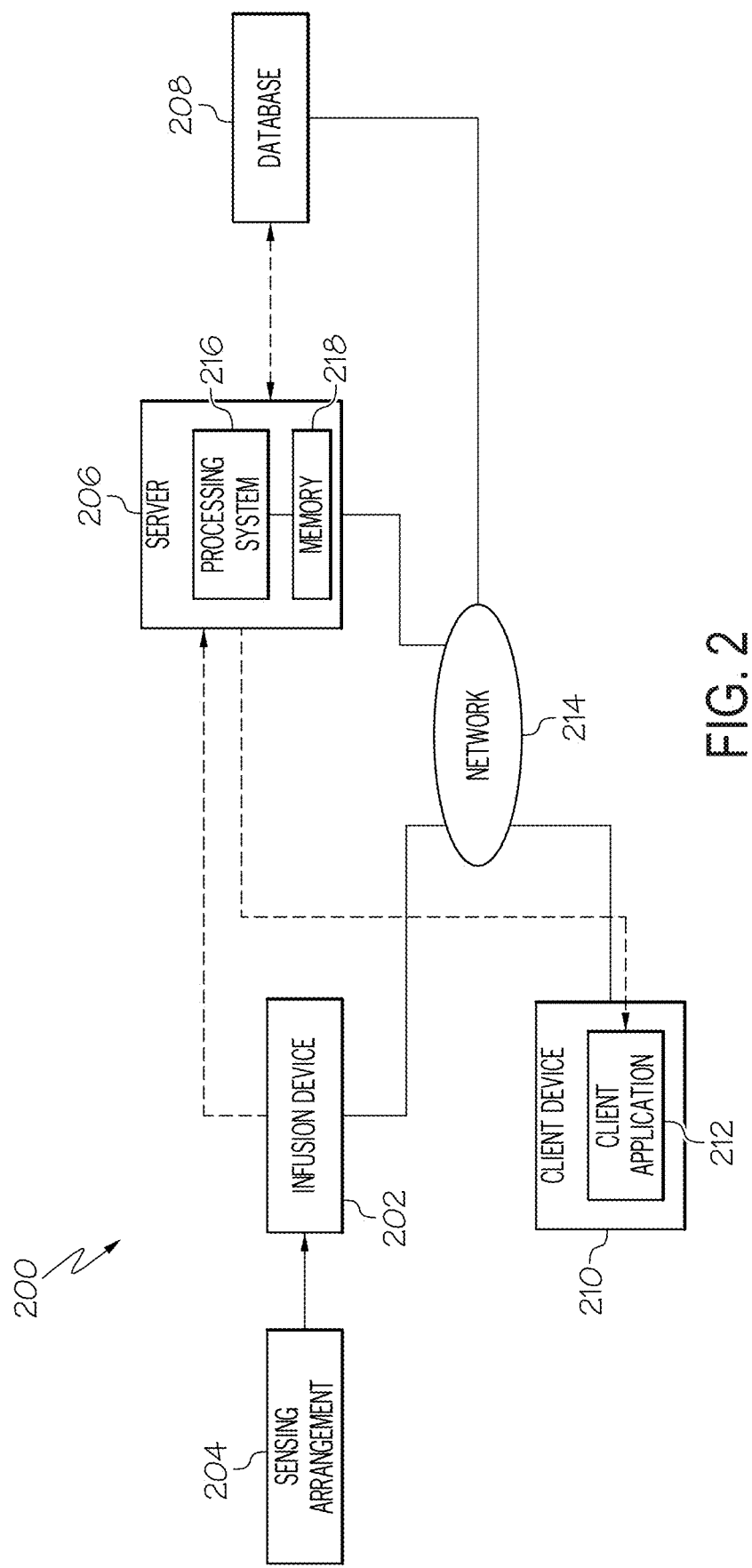
FIG. 2 depicts an exemplary embodiment of a patient management system 200 suitable for generating and presenting the snapshot GUI display of FIG. 1.

FIG. 2 depicts an exemplary embodiment of a patient management system 200 capable of generating and displaying the snapshot GUI display 100 of FIG. 1 for review and analysis of a user. The patient management system 200 includes an infusion device 202 that is communicatively coupled to a sensing arrangement 204 to obtain measurement data indicative of a physiological condition in the body of a patient, such as sensor glucose measurement values as described in greater detail below in the context of FIGS. 6-12. In exemplary embodiments, the infusion device 202 operates autonomously to regulate the patient's glucose level based on the sensor glucose measurement values received from the sensing arrangement 204.

In exemplary embodiments, the infusion device 202 periodically uploads or otherwise transmits the measurement data (e.g., sensor glucose measurement values and timestamps associated therewith) to a remote device 206 via a communications network 214, such as a wired and/or wireless computer network, a cellular network, a mobile broadband network, a radio network, or the like. Additionally, in some embodiments, the infusion device 202 also uploads delivery data and/or other information indicative of the amount of fluid delivered by the infusion device and the timing of fluid delivery, which may include, for example, information pertaining to the amount and timing of manually-initiated boluses and associated meal announcements. Some examples of an infusion device uploading measurement and delivery data to a remote device are described in United States Patent Application Publication Nos. 2015/0057807 and 2015/0057634, which are incorporated by reference herein in their entirety.

The remote device 206 is coupled to a database 208 configured to store or otherwise maintain the historical measurement and delivery data received from the infusion device 202 in association with a patient associated with the infusion device 202 (e.g., using unique patient identification information). The remote device 206 generally represents a server or another suitable electronic device configured to analyze or otherwise monitor the measurement and delivery data obtained for the patient associated with the infusion device 202 and generate a snapshot GUI display (e.g., snapshot GUI display 100) that may be presented on the remote device 206 or another electronic device 210, alternatively referred to herein as a client device. In practice, the remote device 206 may reside at a location that is physically distinct and/or separate from the infusion device 202, such as, for example, at a facility that is owned and/or operated by or otherwise affiliated with a manufacturer of the infusion device 202. For purposes of explanation, but without limitation, the remote device 206 may alternatively be referred to herein as a server.

In the illustrated embodiment, the server 206 generally represents a computing system or another combination of processing logic, circuitry, hardware, and/or other components configured to support the processes, tasks, operations, and/or functions described herein. In this regard, the server 206 includes a processing system 216, which may be implemented using any suitable processing system and/or device, such as, for example, one or more processors, central processing units (CPUs), controllers, microprocessors, microcontrollers, processing cores and/or other hardware computing resources configured to support the operation of the processing system 216 described herein. The processing system 216 may include or otherwise access a data storage element 218 (or memory) capable of storing programming instructions for execution by the processing system 216, that, when read and executed, cause processing system 216 to perform or otherwise support the processes, tasks, operations, and/or functions described herein. For example, in one embodiment, the instructions cause the processing system 216 to create, generate, or otherwise facilitate an application platform that generates or otherwise provides instances of a virtual application at run-time (or "on-demand") based at least in part upon data that is stored or otherwise maintained by the database 208. Depending on the embodiment, the memory 218 may be realized as a random-access memory (RAM), read only memory (ROM), flash memory, magnetic or optical mass storage, or any other suitable non-transitory short or long-term data storage or other computer-readable media, and/or any suitable combination thereof.

The client device 210 generally represents an electronic device coupled to the network 214 that may be utilized by a user to access and view data stored in the database 208 via the server 206. In practice, the client device 210 can be realized as any sort of personal computer, mobile telephone, tablet or other network-enabled electronic device that includes a display device, such as a monitor, screen, or another conventional electronic display, capable of graphically presenting data and/or information provided by the server 206 along with a user input device, such as a keyboard, a mouse, a touchscreen, or the like, capable of receiving input data and/or other information from the user of the client device 210. A user, such as the patient's doctor or another healthcare provider, manipulates the client device 210 to execute a client application 212, such as a web browser application, that contacts the server 206 via the network 214 using a networking protocol, such as the hypertext transport protocol (HTTP) or the like.

In exemplary embodiments described herein, a user of the client device 210 manipulates a user input device associated with the client device 210 to input or otherwise provide indication of the patient associated with the infusion device 202 along with a period of time for which the user would like to review, analyze, or otherwise assess measurement data associated with the patient. In response, the server 206 accesses the database 208 to retrieve or otherwise obtain historical measurement data associated with the identified patient for the identified time period and generates a snapshot GUI display (e.g., snapshot GUI display 100) that is presented on the display device associated with the client device 210 via the client application 212 executing thereon.

It should be appreciated that FIG. 2 depicts a simplified representation of a patient management system 200 for purposes of explanation and is not intended to limit the subject matter described herein in any way. For example, in various embodiments, a snapshot GUI display may be presented on any device within the patient management system 200 (e.g., the server 206, the infusion device 202, the sensing arrangement 204, or the like) and not necessarily on the client device 210. Moreover, in some embodiments, the infusion device 202 may be configured to store or otherwise maintain historical measurement and delivery data onboard the infusion device 202 and generate snapshot GUI displays on a display device associated with the infusion device 202, in which case the server 206, the database 208, and the client device 210 may not be present.

Figure 3:
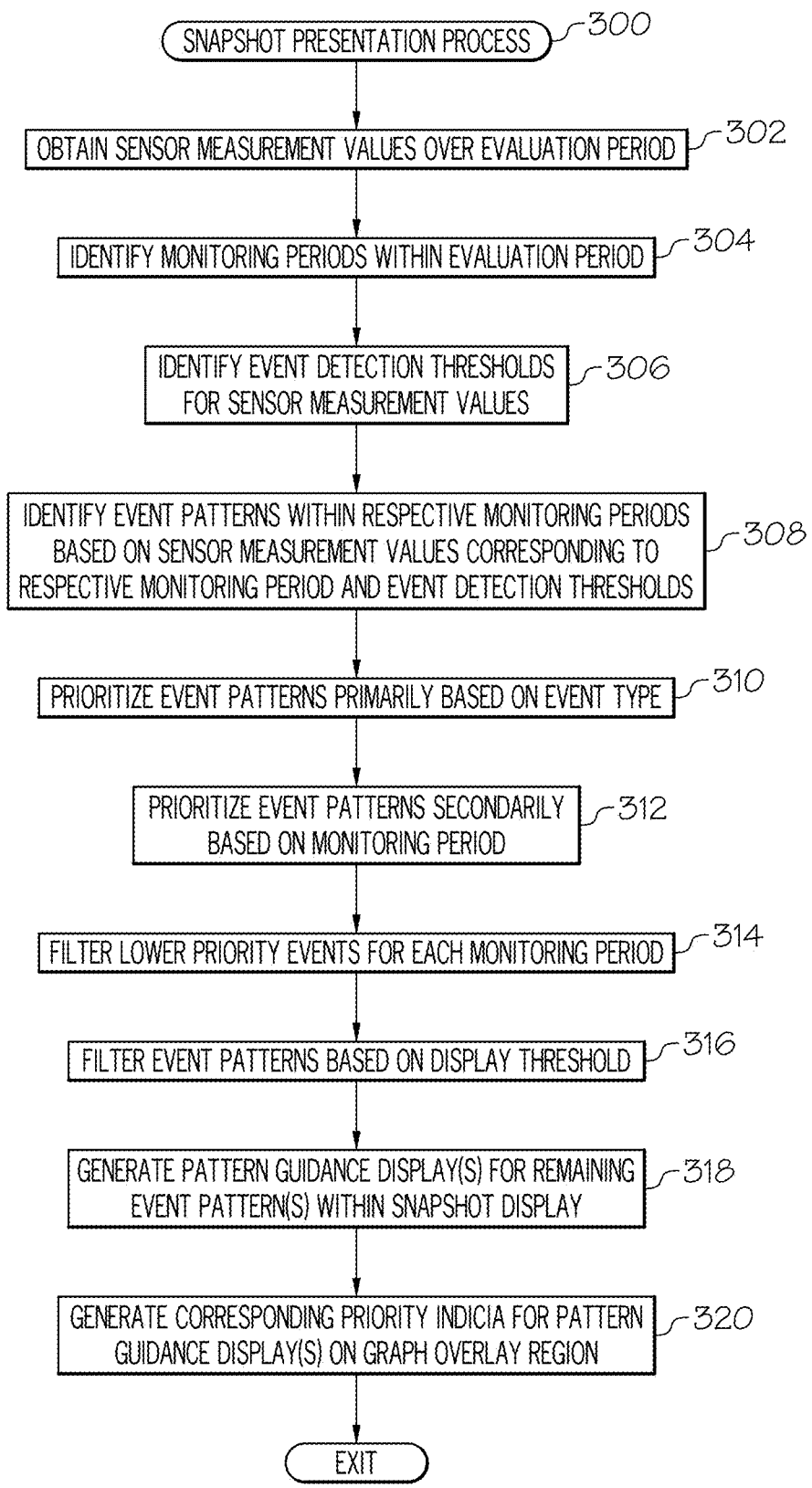
FIG. 3 is a flow diagram of an exemplary snapshot presentation process suitable for use with the patient management system of FIG. 2 to generate a snapshot GUI display in one or more exemplary embodiments.

FIG. 3 depicts an exemplary snapshot presentation process 300 suitable for implementation by a patient management system to provide a snapshot GUI display including information pertaining to preceding operation of an infusion device, such as snapshot GUI display 100 of FIG. 1. The various tasks performed in connection with the snapshot presentation process 300 may be performed by hardware, firmware, software executed by processing circuitry, or any combination thereof. For illustrative purposes, the following description refers to elements mentioned above in connection with FIG. 2. In practice, portions of the snapshot presentation process 300 may be performed by different elements of the patient management system 200, such as, for example, the infusion device 202, the sensing arrangement 204, the server 206, the database 208, the client device 210, the client application 212, and/or the processing system 216. It should be appreciated that the snapshot presentation process 300 may include any number of additional or alternative tasks, the tasks need not be performed in the illustrated order and/or the tasks may be performed concurrently, and/or the snapshot presentation process 300 may be incorporated into a more comprehensive procedure or process having additional functionality not described in detail herein. Moreover, one or more of the tasks shown and described in the context of FIG. 3 could be omitted from a practical embodiment of the snapshot presentation process 300 as long as the intended overall functionality remains intact.

The illustrated snapshot presentation process 300 begins by receiving or otherwise obtaining measurement data for the evaluation period being analyzed (task 302). In this regard, in response to receiving indication of a desired time period for the snapshot GUI display 100, the server 206 accesses the database 208 to obtain the patient's sensor measurement values having associated timestamps that are within the time period for the snapshot GUI display 100. For example, for the embodiment of FIG. 1 where the snapshot time period corresponds to Nov. 3, 2014 to Nov. 6, 2014, the server 206 obtains, from the database 208, the stored sensor measurement values previously obtained by the sensing arrangement 204 having timestamp indicating an associated date from Nov. 3, 2014 to Nov. 6, 2014.

After obtaining the measurement data for the evaluation period, the snapshot presentation process 300 continues by identifying a plurality of different monitoring periods within the evaluation period, identifying event detection thresholds or other parameters or criteria used for detecting event patterns based on the measurement data, and then analyzing the measurement data associated with each of the different monitoring periods with respect to the event detection thresholds to identify event patterns occurring within the respective monitoring periods (tasks 304, 306, 308). In this regard, sensor measurement values are classified into one or more monitoring periods based on the timestamps associated with those values falling within the time period associated with the respective monitoring period(s), and then the sensor measurement values within each monitoring period are analyzed with respect to the various event detection criteria to identify event patterns associated with the respective monitoring period. The sensor measurement values within a monitoring period may be compared to a glucose threshold value to identify a number of times that the sensor measurement values violated the glucose threshold value within the monitoring period, and an event pattern detected when the number is greater than one. For example, a hypoglycemic (or low glucose) event pattern may be identified when sensor measurement values within a monitoring period are below a lower glucose threshold value (e.g., 70 mg/dL) on two or more days within the evaluation period. Similarly, a hyperglycemic (or high glucose) event pattern may be identified when sensor measurement values within a monitoring period are above an upper glucose threshold value (e.g., 150 mg/dL) on two or more days within the evaluation period.

In exemplary embodiments, the different monitoring periods within the evaluation period include an overnight time period, a fasting time period, a breakfast time period, a lunch time period, and a dinner time period. Additionally, in some embodiments, additional monitoring periods may be identified relative to other events, such as, for example, meal indications corresponding to a meal bolus. In such embodiments, measurement values within a fixed period of time (e.g., three hours) preceding a meal indication may be associated with a pre-meal monitoring period, while measurement values within another fixed period time after the meal indication may be associated with a post-meal monitoring period. Depending on the embodiment, the monitoring periods may overlap (e.g., some sensor measurement values fall within multiple different monitoring periods), or the monitoring periods may be mutually exclusive so that each sensor measurement value falls within only one of the monitoring periods. Additionally, in some embodiments, the monitoring periods may be customizable on a patient-specific (or per-patient) basis, with the corresponding end points (e.g., starting and stopping times) or other reference values defining the end points (e.g., the amount of time before/after a meal indication for a pre- or post-meal monitoring period) for the different monitoring time periods being stored or otherwise maintained in the database 208 in association with the patient. The monitoring periods may be customizable on a per-user basis (e.g., doctor to doctor) in a similar manner, with the corresponding timing criteria for the different monitoring time periods being stored or otherwise maintained in the database 208 in association with the user of the client device 210.

Once the monitoring time periods to be analyzed are identified, the server 206 classifies or otherwise categorizes the patient's sensor glucose measurement values into the appropriate monitoring time periods, resulting in a subset of the patient's sensor glucose measurement values associated with each respective monitoring time period. Thereafter, for each monitoring period, the server 206 analyzes that subset of the patient's sensor glucose measurement values to identify any hypoglycemic or hyperglycemic event patterns associated with that respective monitoring period. As described above, the server 206 identifies a hypoglycemic event when one or more of the patient's sensor glucose measurement values within that subset are less than a lower glucose threshold value on at least two different days within the snapshot time period. Similarly, the server 206 identifies a hyperglycemic event when one or more of the patient's sensor glucose measurement values within the subset are greater than an upper glucose threshold value on at least two different days within the snapshot time period.

Additionally, in exemplary embodiments, the server 206 analyzes the subset of the patient's sensor glucose measurement values for the respective monitoring period to detect or otherwise identify a variability event pattern across multiple days within the snapshot time period. For example, in one embodiment, the server 206 identifies a variability event pattern when one or more the patient's sensor glucose measurement values for the monitoring period are less than the lower glucose threshold value on at least two different days within the snapshot time period and one or more of the patient's sensor glucose measurement values within the subset are greater than an upper glucose threshold value on at least two different days within the snapshot time period. In exemplary embodiments, the server 206 also calculates an interquartile range of the daily median sensor glucose measurement values within the monitoring period and detects a variability event pattern when the interquartile range is greater than a variability detection threshold (e.g., 80 mg/dL). It should be noted that the interquartile range is merely one exemplary way in which a variability event pattern may be detected, and in other embodiments, a variability event pattern may be detected based on other statistics calculated based on measurement values for a given monitoring period (e.g., standard deviation values, variance values, or the like).

In a similar manner as described above in the context of the monitoring periods, the detection threshold values or other detection criteria for event patterns may be customizable on a patient-specific (or per-patient) basis, with the corresponding detection threshold values (e.g., the lower glucose threshold value, the upper glucose threshold value, the variability detection threshold value, and the lie) being stored or otherwise maintained in the database 208 in association with the patient. Additionally, or alternatively, in some embodiments, the detection threshold values or other detection criteria may be customizable on a per-user basis (e.g., doctor to doctor) in a similar manner, with the corresponding detection criteria being stored or otherwise maintained in the database 208 in association with the user of the client device 210. Thus, the various criteria used for generating the event detection region 106 on the snapshot GUI display 100 may vary depending on either the patient being analyzed or the user of the client device 210.

Still referring to FIG. 3, after identifying event patterns associated with the different time periods, the snapshot presentation process 300 continues by prioritizing the event patterns according to one or more prioritization criteria to obtain a prioritized list of detected event patterns. In exemplary embodiments, the snapshot presentation process 300 prioritizes the event patterns primarily based on event type, and secondarily based on the monitoring period associated with the respective event patterns (tasks 310, 312). For example, in one embodiment, the server 206 prioritizes, sorts, or otherwise orders variability event patterns ahead of both hypoglycemic and hyperglycemic event patterns, with hypoglycemic event patterns being prioritized or ordered ahead of hyperglycemic event patterns. Thus, prioritization by event type results in variability event patterns being ordered first in a list or other data structure containing the detected event patterns, followed by hypoglycemic event patterns, followed by the hyperglycemic event patterns.

Thereafter, the server 206 prioritizes, sorts, or otherwise orders event patterns for each event type by their associated monitoring period. For example, the server 206 prioritizes, sorts, or otherwise orders the variability event patterns by monitoring period and orders the prioritized variability event patterns ahead of the hypoglycemic event patterns, which are also prioritized or otherwise ordered by monitoring period. In one embodiment, the server 206 prioritizes event patterns by monitoring period in the following order: the fasting time period or pre-breakfast time period, the overnight time period, the breakfast or post-breakfast time period, the dinner or post-dinner time period, the lunch or post-lunch time period, the pre-dinner time period, and the pre-lunch time period. Thus, in such an embodiment, the event patterns may be prioritized as follows: a variability event associated with the fasting time period or pre-breakfast time period, a variability event associated with the overnight time period, a variability event associated with the breakfast or post-breakfast time period, a variability event associated with the dinner or post-dinner time period, a variability event associated with the lunch or post-lunch time period, a variability event associated with the pre-dinner time period, and a variability event associated with the pre-lunch time period, followed by a hypoglycemic event associated with the fasting time period or pre-breakfast time period, a hypoglycemic event associated with the overnight time period, a hypoglycemic event associated with the breakfast or post-breakfast time period, a hypoglycemic event associated with the dinner or post-dinner time period, a hypoglycemic event associated with the lunch or post-lunch time period, a hypoglycemic event associated with the pre-dinner time period, and a hypoglycemic event associated with the pre-lunch time period, followed by a hyperglycemic event associated with the fasting time period or pre-breakfast time period, a hyperglycemic event associated with the overnight time period, a hyperglycemic event associated with the breakfast or post-breakfast time period, a hyperglycemic event associated with the dinner or post-dinner time period, a hyperglycemic event associated with the lunch or post-lunch time period, a hyperglycemic event associated with the pre-dinner time period, and a hyperglycemic event associated with the pre-lunch time period.

For example, referring to FIG. 1, prioritization by monitoring period results in a hyperglycemic event pattern detected within a fasting time period being ordered ahead of a hyperglycemic event pattern detected within an overnight time period (e.g., the period of time preceding 5:00 AM) in the prioritized list. In this regard, more significant time periods for purposes of glycemic control may be preferentially displayed over less significant time periods. For example, since the patient may be sleeping or waking up and less likely or less capable of responding to alerts or notifications generated by the infusion device 202, events occurring overnight or early in the morning prior to eating may require more attention or remedial action than events occurring during the day when the patient is awake and alert and capable of responding to alerts or notifications generated by the infusion device 202.

In a similar manner as described above, the prioritization criteria may be customizable or otherwise configurable on a per-patient or per-user basis and such particular prioritization criteria may be stored or otherwise maintained in the database 208 in association with that patient or user. Additionally, the ordering of the application of the prioritization criteria may be customizable or configurable. For example, in one alternative embodiment, the event patterns are prioritized primarily based on monitoring period and secondarily based on the event type associated with the respective event patterns.

In exemplary embodiments, after prioritizing the detected event patterns, the snapshot presentation process 300 continues by filtering the event patterns according to one or more filtering criteria to obtain a reduced prioritized list of detected event patterns for presentation on the snapshot GUI display. In exemplary embodiments, the snapshot presentation process 300 filters the prioritized list of detected event patterns first by event type priority within the respective monitoring periods to remove or exclude lower priority event patterns and thereby select or retain only the highest priority event pattern detected for each respective monitoring period (task 314). For example, if a hypoglycemic event pattern (e.g., sensor measurement values below a lower threshold value on at least two days), a hyperglycemic event pattern (e.g., sensor measurement values above an upper threshold value on at least two days), and a variability event pattern (e.g., sensor measurement values above an upper threshold value on at least two days and below a lower threshold value on at least two days) are all detected within a particular monitoring period, the server 206 may remove the hypoglycemic event pattern and the hyperglycemic event pattern associated with that monitoring period from the prioritized list of detected event patterns when the variability event type has the highest priority, so that the list retains only the variability event pattern associated with the monitoring period. In this regard, since remedial actions that may be taken by the patient or user to mitigate or otherwise address the highest priority event pattern may also influence the lower priority event patterns, removing lower priority event patterns allows the patient or user to focus on addressing more significant event patterns, which, in turn, could also result in other event patterns detected within that monitoring period being resolved. As noted above, the event type priorities may be customizable or otherwise configurable on a per-patient or per-user basis, such that particular prioritization criteria may be stored or otherwise maintained in the database 208 in association with that patient or user and the resulting types of events preferentially presented within the pattern detection region of the snapshot GUI display may vary depending on the user or patient.

After the filtering the prioritized list of detected event patterns by event type priority within the respective monitoring periods, the resulting list includes only one event pattern for each monitoring period during which an event pattern was detected, with the retained event pattern for a respective monitoring period being the highest priority event pattern within that monitoring period. For example, referring to the embodiment of FIG. 1, when the server 206 identifies a variability event pattern and a hypoglycemic and/or hyperglycemic event pattern within the lunch time monitoring period, only the variability event pattern associated with the lunch time period may remain in the prioritized list after filtering the lower priority event patterns detected within the lunch time period. Similarly, if the server 206 identified both a hypoglycemic event pattern and a hyperglycemic event pattern within the pre-dinner time period, only the hypoglycemic event pattern associated with the pre-dinner time period may remain in the prioritized list.

Still referring to FIG. 3, in exemplary embodiments, after filtering by event type priority within the respective monitoring periods, the snapshot presentation process 300 continues by filtering the list of event patterns based on a display threshold number of event patterns to remove or exclude lower priority event patterns and thereby select or retain only a limited number of the highest priority event patterns for presentation on the snapshot GUI display (task 316). For example, in the embodiment of FIG. 1, the display threshold number is equal to three, so that all event patterns after the first three event patterns in the prioritized list are removed or otherwise excluded, resulting in a filtered prioritized list that includes only the three highest priority event patterns remaining after filtering by event type priority within the respective monitoring periods. Thus, the hyperglycemic event pattern detected for an overnight monitoring period (e.g., the time period preceding the fasting monitoring period) may be filtered or otherwise removed from the list based on the fasting monitoring period being prioritized over the overnight monitoring period (e.g., task 312). Again, it should be noted that the display threshold number may be customizable or otherwise configurable on a per-patient or per-user basis, so that the number of pattern guidance displays presented within the pattern detection region of the snapshot GUI display may vary depending on the user or patient.

The snapshot presentation process 300 continues by generating or otherwise providing pattern guidance displays for the remaining event patterns in the filtered prioritized list within the snapshot GUI display along with corresponding indicia for the event patterns on the graph overlay region of the snapshot GUI display (tasks 318, 320). In exemplary embodiments, the pattern guidance displays are presented in a manner such that higher priority event patterns are preferentially displayed relative to lower priority event patterns, for example, by presenting the highest priority remaining event pattern above and/or to the left of the other remaining event patterns and presenting the lowest priority remaining event pattern below and/or to the right of the other remaining event patterns. The indicia for the remaining event patterns presented on the graph overlay region identify or otherwise indicate the relative priority of the detected event pattern along with the corresponding monitoring period relative to the time period depicted on the graph.

Referring to FIG. 1, prioritization by event type (e.g., task 310) and then by monitoring period (e.g., task 312) results in the variability event pattern detected within the lunch time period being ordered first in the prioritized list, followed by a hypoglycemic event pattern detected within the lunch time period, followed by a hypoglycemic event pattern detected within a pre-dinner time period, followed by a hyperglycemic event pattern detected within a fasting time period, followed by a hyperglycemic event pattern detected within an overnight time period, followed by a hyperglycemic event pattern detected within a dinner or post-dinner time period. Thereafter, filtering by event type priority within monitoring period (e.g., task 314) removes the lunch time hypoglycemic event pattern from the prioritized list, and filtering based on the display threshold (e.g., task 316) removes the overnight hyperglycemic event pattern and the dinner or post-dinner hyperglycemic event pattern, resulting in a filtered prioritized list of three event patterns that includes the lunch time variability event pattern, the pre-dinner hypoglycemic event pattern, and the fasting hyperglycemic event pattern.

The server 206 generates or otherwise provides (e.g., on or to the client application 212 on the client device 210) a pattern guidance display 120 associated with the lunch time variability event pattern that is preferentially displayed relative to (e.g., to the left of) the pattern guidance displays 130, 140 associated with the pre-dinner hypoglycemic event pattern and the fasting hyperglycemic event pattern, with the pre-dinner hypoglycemic guidance display 130 being preferentially displayed relative to the fasting hyperglycemic guidance display 140. As described above, the server 206 generates a marker 128 associated with the lunch time variability guidance display 120 having a position and dimension that encompasses, overlaps, or otherwise indicates the lunch time monitoring period that also includes an indication (e.g., the number 1) that the event pattern associated with the lunch time monitoring period is the highest priority event pattern detected. Similarly, the server 206 generates a second marker 138 having a position and dimension that encompasses, overlaps, or otherwise indicates the pre-dinner monitoring period and includes an indication (e.g., the number 2) that the event pattern associated with the pre-dinner monitoring period is the second highest priority event pattern detected, and the server 206 generates a third marker 148 having a position and dimension that encompasses, overlaps, or otherwise indicates the fasting monitoring period and includes an indication (e.g., the number 3) that the event pattern associated with the fasting monitoring period is the third highest priority event pattern detected.

Figure 4:
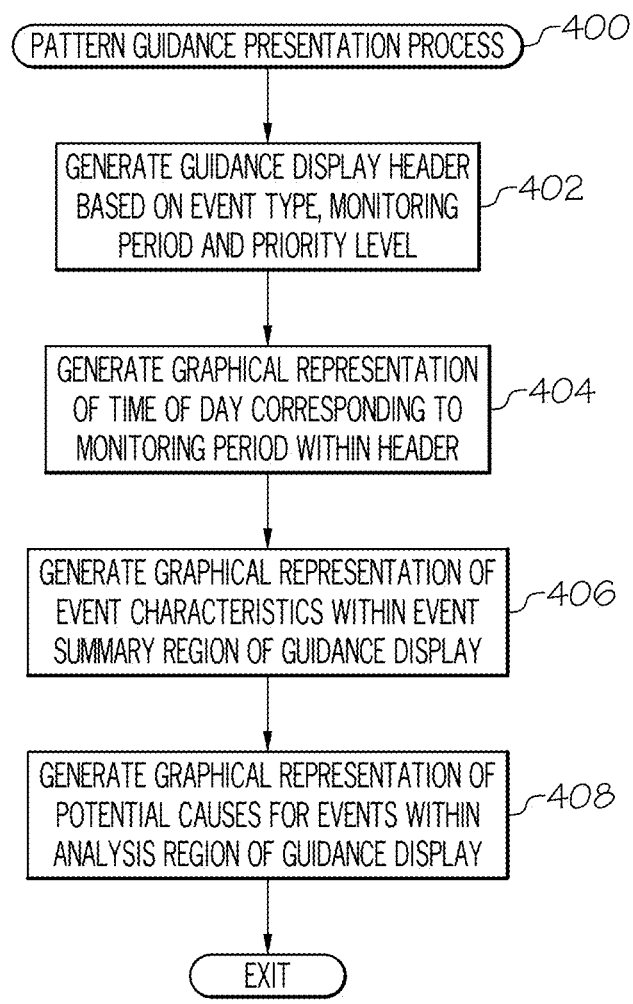
FIG. 4 is a flow diagram of an exemplary pattern guidance presentation process suitable for use with the patient management system of FIG. 2 in conjunction with the snapshot presentation process of FIG. 3 to populate an event pattern detection region of a snapshot GUI display in one or more exemplary embodiments.

FIG. 4 depicts an exemplary pattern guidance presentation process 400 suitable for implementation in conjunction with the snapshot presentation process 300 of FIG. 3 to generate pattern guidance displays within a pattern detection region of a snapshot GUI display, such as pattern guidance displays 120, 130, 140 within pattern detection region 106 of the snapshot GUI display 100 of FIG. 1. The various tasks performed in connection with the pattern guidance presentation process 400 may be performed by hardware, firmware, software executed by processing circuitry, or any combination thereof. For illustrative purposes, the following description refers to elements mentioned above in connection with FIG. 2. In practice, portions of the pattern guidance presentation process 400 may be performed by different elements of the patient management system 200; however, for purposes of explanation, the subject matter may be described in the context of the guidance presentation process 400 being performed by the server 206. It should be appreciated that the pattern guidance presentation process 400 may include any number of additional or alternative tasks, the tasks need not be performed in the illustrated order and/or the tasks may be performed concurrently, and/or the pattern guidance presentation process 400 may be incorporated into a more comprehensive procedure or process having additional functionality not described in detail herein. Moreover, one or more of the tasks shown and described in the context of FIG. 4 could be omitted from a practical embodiment of the pattern guidance presentation process 400 as long as the intended overall functionality remains intact.

In exemplary embodiments, the pattern guidance presentation process 400 is performed for each detected event pattern that remains in the filtered prioritized list (e.g., task 318) to populate the pattern detection region on a snapshot GUI display. The illustrated process 400 generates a header for the pattern guidance display based on the event type and monitoring period associated with the detected event pattern along with the priority of the detected event pattern in the filtered prioritized list (task 402). In this regard, the pattern guidance header identifies the type of event pattern that was detected, the monitoring period that event pattern was detected within, and the priority level associated with that event pattern based on the prioritization criteria. For example, referring to FIG. 1, the server 206 generates a header region 122 for the first guidance display 120 within the event pattern region 106 that identifies the first event pattern is a variability event with respect to the patient's sensor glucose values (e.g., "Variable SG") and that the event pattern was detected within a lunch time monitoring period, with the number one indicating the lunch time variability event is the highest priority event pattern detected. Similarly, the server 206 generates a header region 132 for the second guidance display 130 that identifies the second event pattern is a hypoglycemic event with respect to the patient's sensor glucose values (e.g., "Low SG") and that the event pattern was detected within a pre-dinner monitoring period, with the number two indicating the pre-dinner hypoglycemic event is the second highest priority event pattern detected. The server 206 also generates a header region 142 for the third guidance display 140 that identifies the third event pattern is a hyperglycemic event with respect to the patient's sensor glucose values (e.g., "High SG") and that the event pattern was detected within a fasting monitoring period, with the number three indicating the fasting hyperglycemic event is the third highest priority event pattern detected.

In exemplary embodiments, the guidance presentation process 400 also generates a graphical representation of the time of day corresponding to the respective monitoring periods associated with the displayed event patterns (task 404). In this manner, the time of day corresponding to a particular named monitoring period and the relationship between sensor glucose measurement values and that monitoring period may be made apparent to the user in conjunction with the markers 128, 138, 148 presented on the graph overlay region 108. For a monitoring period defined or otherwise referenced from another event or time (e.g., a meal announcement or maker), the server 206 may calculate or otherwise determine the end points for the current instance of that monitoring period within the current snapshot time period and provide graphical representation of that time period encompassing the period between those end points within the respective header region. For example, in FIG. 1, the time of day associated with the current instance of the pre-dinner monitoring period associated with pattern guidance display 130 could be calculated or otherwise determined based on respective timings of meal announcements or markers during the current snapshot time period depicted in the graph overlay region 108 that occur in the evening, while accounting for any offset values that are stored in the database 208 in association with the current patient or user and define the boundaries of the pre-dinner monitoring period relative to those meal announcements. That said, default time period end points may also be used in the absence of sufficient meal announcements within a designated dinner time period (e.g., which could also be defined by default end point values or be customizable). For other monitoring periods, the server 206 may obtain the stored end points associated with that monitoring period in the database 208 for the current patient or user and provide a graphical representation of the monitoring period time of day.

In the illustrated embodiment, the server 206 generates a graphical representation of the time of day associated with the lunch monitoring period (e.g., 11:00 AM-3:00 PM predefined lunch time period since insufficient evening meal announcements exist within that timeframe for calculating based on meal announcement timings) in the first header region 122, a graphical representation of the time of day associated with the pre-dinner monitoring period (e.g., the 5:00 PM-8:00 PM predefined time period since insufficient evening meal announcements exist within that timeframe for calculating based on meal announcement timings) in the second header region 132, and a graphical representation of the time of day associated with the fasting monitoring period (e.g., 5:00 AM-7:00 AM) in the third header region 142. As illustrated, the header may include a footnote symbol or other indicia that indicates whether a monitoring period capable of being adaptively and dynamically calculated based on meal announcements was able to be determined, and if not, provide indication that a fixed time of day is utilized due to insufficient meal announcements within a default timeframe (or predefined range of time) associated with that respective monitoring period.

Still referring to FIG. 4, the guidance presentation process 400 also generates a graphical representation of one or more characteristics summarizing, quantifying or otherwise describing the nature of the displayed event patterns, such as, for example, the severity, frequency, intensity, or the like (task 406). Thus, a user may quickly ascertain the relative significance or impact of the individual events that resulted in the detected event pattern with respect to the patient's physiological condition during the snapshot time period in conjunction with the relative priority of that event pattern. It should be noted that any number of different characteristics or metrics that summarize, quantify or otherwise describe the nature of a detected event pattern or the individual component events of the event pattern may be determined and presented, and the subject matter is not intended to be limited to any particular characteristics or metric presented in a pattern guidance display.

For example, for a variability event pattern associated with a given monitoring period, the number of days that a variability event was detected within that monitoring period may be determined and presented, thereby providing indication of the frequency or regularity of the variability event. For example, in the embodiment of FIG. 1, based on the sensor glucose measurement values corresponding to the lunch time monitoring period, the server 206 may calculate or otherwise determine that a variability event occurred on four different days within the snapshot time period and provide a graphical representation of the variability event frequency within an event pattern summary region 124 of the pattern guidance display 120 beneath the header region 122. In this example, a user may readily identify that the variability event is the highest priority event pattern detected within the snapshot time period while also identifying the occurrence of a variability event at during the lunch time period on every day of the snapshot time period, and thereby be apprised of the relative importance of addressing the lunch time variability event.

For low or high glucose event patterns, the number of days the sensor glucose measurement values violated one or more thresholds within that monitoring period or otherwise fell within distinct ranges of measurement values may also be determined and presented. For example, in the embodiment of FIG. 1, based on the sensor glucose measurement values corresponding to the pre-dinner monitoring period, the server 206 may calculate or otherwise determine the number of days within the snapshot time period that the sensor glucose measurement values were within the range between a hypoglycemic glucose threshold (e.g., 50 mg/dL) and a lower glucose target range threshold (e.g., 70 mg/dL) and provide a corresponding graphical representation of the lower severity hypoglycemic event frequency within an event pattern summary region 134 of the pattern guidance display 130, while also determining the number of days within the snapshot time period that those sensor glucose measurement values were below the hypoglycemic glucose threshold and provide a corresponding graphical representation of the higher severity hypoglycemic event frequency within the event pattern summary region 134. Similarly, the server 206 may calculate or otherwise determine, based on the sensor glucose measurement values corresponding to the fasting monitoring period, the number of days within the snapshot time period that the sensor glucose measurement values were within the range between an upper target range threshold (e.g., 150 mg/dL) and a hyperglycemic glucose threshold (e.g., 250 mg/dL) and provide a corresponding graphical representation of the lower severity hyperglycemic event frequency within event pattern summary region 144, while also determining the number of days within the snapshot time period that those sensor glucose measurement values were above the hyperglycemic glucose threshold and provide a corresponding graphical representation of the higher severity hyperglycemic event frequency within the event pattern summary region 144.

Referring again to FIG. 4, the guidance presentation process 400 also generates a graphical representation of one or more potential causes for the detected event pattern within the pattern guidance display (task 408). In this regard, the potential causes may be stored or otherwise maintained in the database 208 in association with the particular combination of event type and monitoring period (or time of day), with the server 206 retrieving or otherwise obtaining the appropriate potential causes that correspond to the current combination of event type and monitoring period presented on the snapshot display. For example, to populate the event pattern analysis region 126 of the pattern guidance display 120, the server 206 accesses the database 208 to identify the list of potential causes associated with the variability event type that are also associated with the lunch time monitoring period (or a time of day between 11:00 AM and 3:00 PM) and then generates or otherwise provides a graphical representation of that list of causes in the analysis region 126. In some embodiments, the potential causes may be phrased in a manner that suggests remedial actions that can be taken to resolve or correct the event pattern. In other embodiments described in greater detail below in the context of FIGS. 13-16, potential remedial actions (or corresponding logic rules for determining such remedial actions) may also be stored or otherwise maintained in the database 208 in association with the particular combination of event type and monitoring period (or time of day). In such embodiments, the server 206 may identify or otherwise determine the appropriate potential remedial actions (or logical rules therefor) that correspond to the current combination of event type and monitoring period presented on the snapshot display and then generate graphical representations of those remedial actions within the event pattern analysis region 126, 136, 146.

Referring to FIGS. 1-4, by virtue of the subject matter described above, a user may quickly ascertain or otherwise identify the most significant event patterns detected within a particular time period being evaluated on the snapshot GUI display 100, while also being able to quickly ascertain the relative impact or significance of the constituent events with respect to the patient's glycemic control, the temporal characteristics or significance of those events, and the potential causes or remedial actions for those events at the times of day during which they were detected. This is particularly useful in the context of a patient management system, such as patient management system 200 of FIG. 2, where the doctor or other medical professional or healthcare provider monitoring the glycemic control of the patient associated with the infusion device 202 utilizes a client device 210 to access and review historical data associated with the patient over a select period of time from the database 208 via the server 206. In exemplary embodiments, the server 206 generates or otherwise provides a snapshot GUI display 100 within a client application 212 on the client device 210 that includes pattern guidance displays 120, 130, 140 associated with the highest priority event patterns detected based on the patient's historical measurement data within the desired evaluation period in conjunction with a performance metric region 104 and graph overlay region 108 that also reflect the patient's historical measurement data within the desired evaluation period. As a result, the snapshot GUI display 100 allows the user of the client device 210 to quickly assess the general characteristics or nature of the glycemic control for the patient achieved by the infusion device 202, while also apprising the user of the most notable event patterns detected within the desired evaluation period, their relative significance or impact, and their potential causes or remedies. Thus, the snapshot GUI display 100 can aid a doctor or other care provider seeking to integrate continuous glucose monitoring and/or other autonomous glucose regulation by the infusion device 202 into his or her practice in an efficient manner by detecting, prioritizing, filtering, and characterizing event patterns automatically (e.g., without requiring manual input or analysis). This, in turn, facilitates improved patient outcomes.

Diabetes Data Management System Overview

Figure 5:
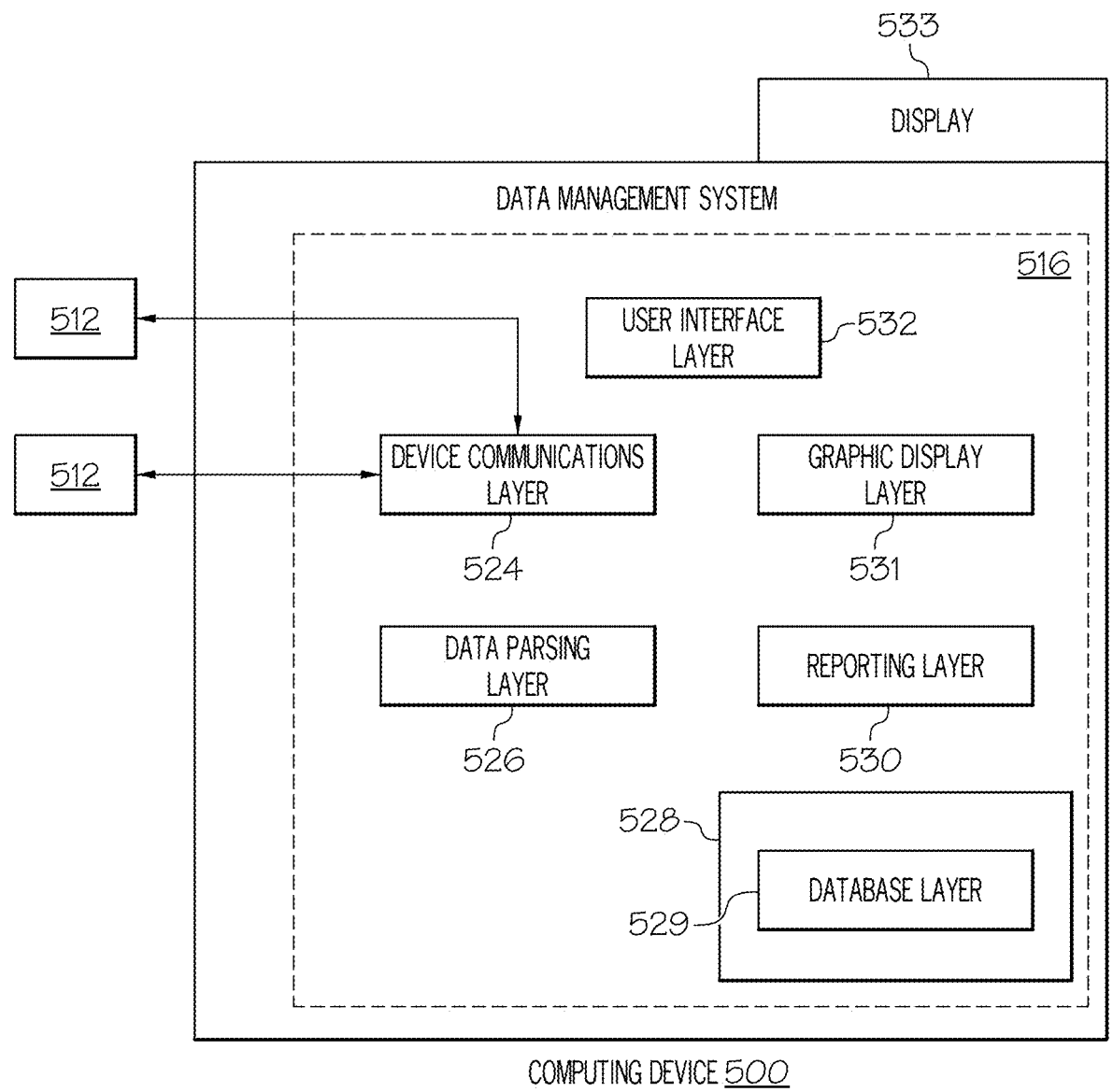
FIG. 5 depicts an embodiment of a computing device for a diabetes data management system in accordance with one or more embodiments.

FIG. 5 illustrates a computing device 500 including a display 533 suitable for presenting a snapshot GUI display 100 as part of a diabetes data management system in conjunction with the processes 300, 400 of FIGS. 3-4 described above. The diabetes data management system (DDMS) may be referred to as the Medtronic MiniMed CARELINK™ system or as a medical data management system (MDMS) in some embodiments. The DDMS may be housed on a server or a plurality of servers which a user or a health care professional may access via a communications network via the Internet or the World Wide Web. Some models of the DDMS, which is described as an MDMS, are described in U.S. Patent Application Publication Nos. 2006/0031094 and 2013/0338630, which is herein incorporated by reference in their entirety.

While description of embodiments may be made in regard to monitoring medical or biological conditions for subjects having diabetes, the systems and processes herein are applicable to monitoring medical or biological conditions for cardiac subjects, cancer subjects, HIV subjects, subjects with other disease, infection, or controllable conditions, or various combinations thereof.

In embodiments of the invention, the DDMS may be installed in a computing device in a health care provider's office, such as a doctor's office, a nurse's office, a clinic, an emergency room, an urgent care office. Health care providers may be reluctant to utilize a system where their confidential patient data is to be stored in a computing device such as a server on the Internet.

The DDMS may be installed on a computing device 500. The computing device 500 may be coupled to a display 533. In some embodiments, the computing device 500 may be in a physical device separate from the display (such as in a personal computer, a mini-computer, etc.) In some embodiments, the computing device 500 may be in a single physical enclosure or device with the display 533 such as a laptop where the display 533 is integrated into the computing device. In embodiments of the invention, the computing device 500 hosting the DDMS may be, but is not limited to, a desktop computer, a laptop computer, a server, a network computer, a personal digital assistant (PDA), a portable telephone including computer functions, a pager with a large visible display, an insulin pump including a display, a glucose sensor including a display, a glucose meter including a display, and/or a combination insulin pump/glucose sensor having a display. The computing device may also be an insulin pump coupled to a display, a glucose meter coupled to a display, or a glucose sensor coupled to a display. The computing device 500 may also be a server located on the Internet that is accessible via a browser installed on a laptop computer, desktop computer, a network computer, or a PDA. The computing device 500 may also be a server located in a doctor's office that is accessible via a browser installed on a portable computing device, e.g., laptop, PDA, network computer, portable phone, which has wireless capabilities and can communicate via one of the wireless communication protocols such as Bluetooth and IEEE 802.11 protocols.

In the embodiment shown in FIG. 5, the data management system 516 comprises a group of interrelated software modules or layers that specialize in different tasks. The system software includes a device communication layer 524, a data parsing layer 526, a database layer 528, database storage devices 529, a reporting layer 530, a graph display layer 531, and a user interface layer 532. The diabetes data management system may communicate with a plurality of subject support devices 512, two of which are illustrated in FIG. 5. Although the different reference numerals refer to a number of layers, (e.g., a device communication layer, a data parsing layer, a database layer), each layer may include a single software module or a plurality of software modules. For example, the device communications layer 524 may include a number of interacting software modules, libraries, etc. In embodiments of the invention, the data management system 516 may be installed onto a non-volatile storage area (memory such as flash memory, hard disk, removable hard, DVD-RW, CD-RW) of the computing device 500. If the data management system 516 is selected or initiated, the system 516 may be loaded into a volatile storage (memory such as DRAM, SRAM, RAM, DDRAM) for execution.

The device communication layer 524 is responsible for interfacing with at least one, and, in further embodiments, to a plurality of different types of subject support devices 512, such as, for example, blood glucose meters, glucose sensors/monitors, or an infusion pump. In one embodiment, the device communication layer 524 may be configured to communicate with a single type of subject support device 512. However, in more comprehensive embodiments, the device communication layer 524 is configured to communicate with multiple different types of subject support devices 512, such as devices made from multiple different manufacturers, multiple different models from a particular manufacturer and/or multiple different devices that provide different functions (such as infusion functions, sensing functions, metering functions, communication functions, user interface functions, or combinations thereof). By providing an ability to interface with multiple different types of subject support devices 512, the diabetes data management system 516 may collect data from a significantly greater number of discrete sources. Such embodiments may provide expanded and improved data analysis capabilities by including a greater number of subjects and groups of subjects in statistical or other forms of analysis that can benefit from larger amounts of sample data and/or greater diversity in sample data, and, thereby, improve capabilities of determining appropriate treatment parameters, diagnostics, or the like.

The device communication layer 524 allows the DDMS 516 to receive information from and transmit information to or from each subject support device 512 in the system 516. Depending upon the embodiment and context of use, the type of information that may be communicated between the system 516 and device 512 may include, but is not limited to, data, programs, updated software, education materials, warning messages, notifications, device settings, therapy parameters, or the like. The device communication layer 524 may include suitable routines for detecting the type of subject support device 512 in communication with the system 516 and implementing appropriate communication protocols for that type of device 512. Alternatively, or in addition, the subject support device 512 may communicate information in packets or other data arrangements, where the communication includes a preamble or other portion that includes device identification information for identifying the type of the subject support device. Alternatively, or in addition, the subject support device 512 may include suitable user-operable interfaces for allowing a user to enter information, such as by selecting an optional icon or text or other device identifier that corresponds to the type of subject support device used by that user. Such information may be communicated to the system 516, through a network connection. In yet further embodiments, the system 516 may detect the type of subject support device 512 it is communicating with in the manner described above and then may send a message requiring the user to verify that the system 516 properly detected the type of subject support device being used by the user. For systems 516 that are capable of communicating with multiple different types of subject support devices 512, the device communication layer 524 may be capable of implementing multiple different communication protocols and selects a protocol that is appropriate for the detected type of subject support device.

The data-parsing layer 526 is responsible for validating the integrity of device data received and for inputting it correctly into a database 529. A cyclic redundancy check (CRC) process for checking the integrity of the received data may be employed. Alternatively, or in addition, data may be received in packets or other data arrangements, where preambles or other portions of the data include device type identification information. Such preambles or other portions of the received data may further include device serial numbers or other identification information that may be used for validating the authenticity of the received information. In such embodiments, the system 516 may compare received identification information with pre-stored information to evaluate whether the received information is from a valid source.

The database layer 528 may include a centralized database repository that is responsible for warehousing and archiving stored data in an organized format for later access, and retrieval. The database layer 528 operates with one or more data storage device(s) 529 suitable for storing and providing access to data in the manner described herein. Such data storage device(s) 529 may comprise, for example, one or more hard discs, optical discs, tapes, digital libraries or other suitable digital or analog storage media and associated drive devices, drive arrays or the like.

Data may be stored and archived for various purposes, depending upon the embodiment and environment of use. Information regarding specific subjects and patient support devices may be stored and archived and made available to those specific subjects, their authorized healthcare providers and/or authorized healthcare payor entities for analyzing the subject's condition. Also, certain information regarding groups of subjects or groups of subject support devices may be made available more generally for healthcare providers, subjects, personnel of the entity administering the system 516 or other entities, for analyzing group data or other forms of conglomerate data.

Embodiments of the database layer 528 and other components of the system 516 may employ suitable data security measures for securing personal medical information of subjects, while also allowing non-personal medical information to be more generally available for analysis. Embodiments may be configured for compliance with suitable government regulations, industry standards, policies or the like, including, but not limited to the Health Insurance Portability and Accountability Act of 1996 (HIPAA).

The database layer 528 may be configured to limit access of each user to types of information pre-authorized for that user. For example, a subject may be allowed access to his or her individual medical information (with individual identifiers) stored by the database layer 528, but not allowed access to other subject's individual medical information (with individual identifiers). Similarly, a subject's authorized healthcare provider or payor entity may be provided access to some or all of the subject's individual medical information (with individual identifiers) stored by the database layer 528, but not allowed access to another individual's personal information. Also, an operator or administrator-user (on a separate computer communicating with the computing device 500) may be provided access to some or all subject information, depending upon the role of the operator or administrator. On the other hand, a subject, healthcare provider, operator, administrator or other entity, may be authorized to access general information of unidentified individuals, groups or conglomerates (without individual identifiers) stored by the database layer 528 in the data storage devices 529.

In embodiments of the invention, the database layer 528 may store preference profiles. In the database layer 528, for example, each user may store information regarding specific parameters that correspond to the user. Illustratively, these parameters could include target blood glucose or sensor glucose levels, what type of equipment the users utilize (insulin pump, glucose sensor, blood glucose meter, etc.) and could be stored in a record, a file, or a memory location in the data storage device(s) 529 in the database layer. As described above, preference profiles may include various threshold values, monitoring period values, prioritization criteria, filtering criteria, and/or other user-specific values for parameters utilized by the processes 300, 400 described above to generate a snapshot GUI display, such as snapshot GUI display 100, on the display 533 or a support device 512 in a personalized or patient-specific manner.

The DDMS 516 may measure, analyze, and track either blood glucose (BG) or sensor glucose (SG) readings for a user. In embodiments of the invention, the medical data management system may measure, track, or analyze both BG and SG readings for the user. Accordingly, although certain reports may mention or illustrate BG or SG only, the reports may monitor and display results for the other one of the glucose readings or for both of the glucose readings.

The reporting layer 530 may include a report wizard program that pulls data from selected locations in the database 529 and generates report information from the desired parameters of interest. The reporting layer 530 may be configured to generate multiple different types of reports, each having different information and/or showing information in different formats (arrangements or styles), where the type of report may be selectable by the user. A plurality of pre-set types of report (with pre-defined types of content and format) may be available and selectable by a user. At least some of the pre-set types of reports may be common, industry standard report types with which many healthcare providers should be familiar. In exemplary embodiments described herein, the reporting layer 530 also facilitates generation of a snapshot report including a snapshot GUI display, such as snapshot GUI display 100 of FIG. 1.

In embodiments of the invention, the database layer 528 may calculate values for various medical information that is to be displayed on the reports generated by the report or reporting layer 530. For example, the database layer 528 may calculate average blood glucose or sensor glucose readings for specified timeframes. In embodiments of the invention, the reporting layer 530 may calculate values for medical or physical information that is to be displayed on the reports. For example, a user may select parameters which are then utilized by the reporting layer 530 to generate medical information values corresponding to the selected parameters. In other embodiments of the invention, the user may select a parameter profile that previously existed in the database layer 528.

Alternatively, or in addition, the report wizard may allow a user to design a custom type of report. For example, the report wizard may allow a user to define and input parameters (such as parameters specifying the type of content data, the time period of such data, the format of the report, or the like) and may select data from the database and arrange the data in a printable or displayable arrangement, based on the user-defined parameters. In further embodiments, the report wizard may interface with or provide data for use by other programs that may be available to users, such as common report generating, formatting or statistical analysis programs. In this manner, users may import data from the system 516 into further reporting tools familiar to the user. The reporting layer 530 may generate reports in displayable form to allow a user to view reports on a standard display device, printable form to allow a user to print reports on standard printers, or other suitable forms for access by a user. Embodiments may operate with conventional file format schemes for simplifying storing, printing and transmitting functions, including, but not limited to PDF, JPEG, or the like. Illustratively, a user may select a type of report and parameters for the report and the reporting layer 530 may create the report in a PDF format. A PDF plug-in may be initiated to help create the report and also to allow the user to view the report. Under these operating conditions, the user may print the report utilizing the PDF plug-in. In certain embodiments in which security measures are implemented, for example, to meet government regulations, industry standards or policies that restrict communication of subject's personal information, some or all reports may be generated in a form (or with suitable software controls) to inhibit printing, or electronic transfer (such as a non-printable and/or non-capable format). In yet further embodiments, the system 516 may allow a user generating a report to designate the report as non-printable and/or non-transferable, whereby the system 516 will provide the report in a form that inhibits printing and/or electronic transfer.

The reporting layer 530 may transfer selected reports to the graph display layer 531. The graph display layer 531 receives information regarding the selected reports and converts the data into a format that can be displayed or shown on a display 533.

In embodiments of the invention, the reporting layer 530 may store a number of the user's parameters. Illustratively, the reporting layer 530 may store the type of carbohydrate units, a blood glucose movement or sensor glucose reading, a carbohydrate conversion factor, and timeframes for specific types of reports. These examples are meant to be illustrative and not limiting.

Data analysis and presentations of the reported information may be employed to develop and support diagnostic and therapeutic parameters. Where information on the report relates to an individual subject, the diagnostic and therapeutic parameters may be used to assess the health status and relative well-being of that subject, assess the subject's compliance to a therapy, as well as to develop or modify treatment for the subject and assess the subject's behaviors that affect his/her therapy. Where information on the report relates to groups of subjects or conglomerates of data, the diagnostic and therapeutic parameters may be used to assess the health status and relative well-being of groups of subjects with similar medical conditions, such as, but not limited to, diabetic subjects, cardiac subjects, diabetic subjects having a particular type of diabetes or cardiac condition, subjects of a particular age, sex or other demographic group, subjects with conditions that influence therapeutic decisions such as but not limited to pregnancy, obesity, hypoglycemic unawareness, learning disorders, limited ability to care for self, various levels of insulin resistance, combinations thereof, or the like.

The user interface layer 532 supports interactions with the end user, for example, for user login and data access, software navigation, data input, user selection of desired report types and the display of selected information. Users may also input parameters to be utilized in the selected reports via the user interface layer 532. Examples of users include but are not limited to: healthcare providers, healthcare payer entities, system operators or administrators, researchers, business entities, healthcare institutions and organizations, or the like, depending upon the service being provided by the system and depending upon the invention embodiment. More comprehensive embodiments are capable of interacting with some or all of the above-noted types of users, wherein different types of users have access to different services or data or different levels of services or data.

In an example embodiment, the user interface layer 532 provides one or more websites accessible by users on the Internet. The user interface layer may include or operate with at least one (or multiple) suitable network server(s) to provide the website(s) over the Internet and to allow access, world-wide, from Internet-connected computers using standard Internet browser software. The website(s) may be accessed by various types of users, including but not limited to subjects, healthcare providers, researchers, business entities, healthcare institutions and organizations, payor entities, pharmaceutical partners or other sources of pharmaceuticals or medical equipment, and/or support personnel or other personnel running the system 516, depending upon the embodiment of use.

In another example embodiment, where the DDMS 516 is located on one computing device 500, the user interface layer 532 provides a number of menus to the user to navigate through the DDMS. These menus may be created utilizing any menu format, including but not limited to HTML, XML, or Active Server pages. A user may access the DDMS 516 to perform one or more of a variety of tasks, such as accessing general information made available on a website to all subjects or groups of subjects. The user interface layer 532 of the DDMS 516 may allow a user to access specific information or to generate reports regarding that subject's medical condition or that subject's medical device(s) 512, to transfer data or other information from that subject's support device(s) 512 to the system 516, to transfer data, programs, program updates or other information from the system 516 to the subject's support device(s) 512, to manually enter information into the system 516, to engage in a remote consultation exchange with a healthcare provider, or to modify the custom settings in a subject's supported device and/or in a subject's DDMS/MDMS data file.

The system 516 may provide access to different optional resources or activities (including accessing different information items and services) to different users and to different types or groups of users, such that each user may have a customized experience and/or each type or group of users (e.g., all users, diabetic users, cardio users, healthcare provider-user or payor-user, or the like) may have a different set of information items or services available on the system. The system 516 may include or employ one or more suitable resource provisioning program or system for allocating appropriate resources to each user or type of user, based on a pre-defined authorization plan. Resource provisioning systems are well known in connection with provisioning of electronic office resources (email, software programs under license, sensitive data, etc.) in an office environment, for example, in a local area network LAN for an office, company or firm. In one example embodiment, such resource provisioning systems is adapted to control access to medical information and services on the DDMS 516, based on the type of user and/or the identity of the user.

Upon entering successful verification of the user's identification information and password, the user may be provided access to secure, personalized information stored on the DDMS 516. For example, the user may be provided access to a secure, personalized location in the DDMS 516 which has been assigned to the subject. This personalized location may be referred to as a personalized screen, a home screen, a home menu, a personalized page, etc. The personalized location may provide a personalized home screen to the subject, including selectable icons or menu items for selecting optional activities, including, for example, an option to transfer device data from a subject's supported device 512 to the system 516, manually enter additional data into the system 516, modify the subject's custom settings, and/or view and print reports. Reports may include data specific to the subject's condition, including but not limited to, data obtained from the subject's support device(s) 512, data manually entered, data from medical libraries or other networked therapy management systems, data from the subjects or groups of subjects, or the like. Where the reports include subject-specific information and subject identification information, the reports may be generated from some or all subject data stored in a secure storage area (e.g., storage devices 529) employed by the database layer 528.

The user may select an option to transfer (send) device data to the medical data management system 516. If the system 516 receives a user's request to transfer device data to the system, the system 516 may provide the user with step-by-step instructions on how to transfer data from the subject's supported device(s) 512. For example, the DDMS 516 may have a plurality of different stored instruction sets for instructing users how to download data from different types of subject support devices, where each instruction set relates to a particular type of subject supported device (e.g., pump, sensor, meter, or the like), a particular manufacturer's version of a type of subject support device, or the like. Registration information received from the user during registration may include information regarding the type of subject support device(s) 512 used by the subject. The system 516 employs that information to select the stored instruction set(s) associated with the particular subject's support device(s) 512 for display to the user.

Other activities or resources available to the user on the system 516 may include an option for manually entering information to the DDMS/MDMS 516. For example, from the user's personalized menu or location, the user may select an option to manually enter additional information into the system 516.

Further optional activities or resources may be available to the user on the DDMS 516. For example, from the user's personalized menu, the user may select an option to receive data, software, software updates, treatment recommendations or other information from the system 516 on the subject's support device(s) 512. If the system 516 receives a request from a user to receive data, software, software updates, treatment recommendations or other information, the system 516 may provide the user with a list or other arrangement of multiple selectable icons or other indicia representing available data, software, software updates or other information available to the user.

Yet further optional activities or resources may be available to the user on the medical data management system 516 including, for example, an option for the user to customize or otherwise further personalize the user's personalized location or menu. In particular, from the user's personalized location, the user may select an option to customize parameters for the user. In addition, the user may create profiles of customizable parameters. When the system 516 receives such a request from a user, the system 516 may provide the user with a list or other arrangement of multiple selectable icons or other indicia representing parameters that may be modified to accommodate the user's preferences. When a user selects one or more of the icons or other indicia, the system 516 may receive the user's request and makes the requested modification.

Infusion System Overview

Figure 6:
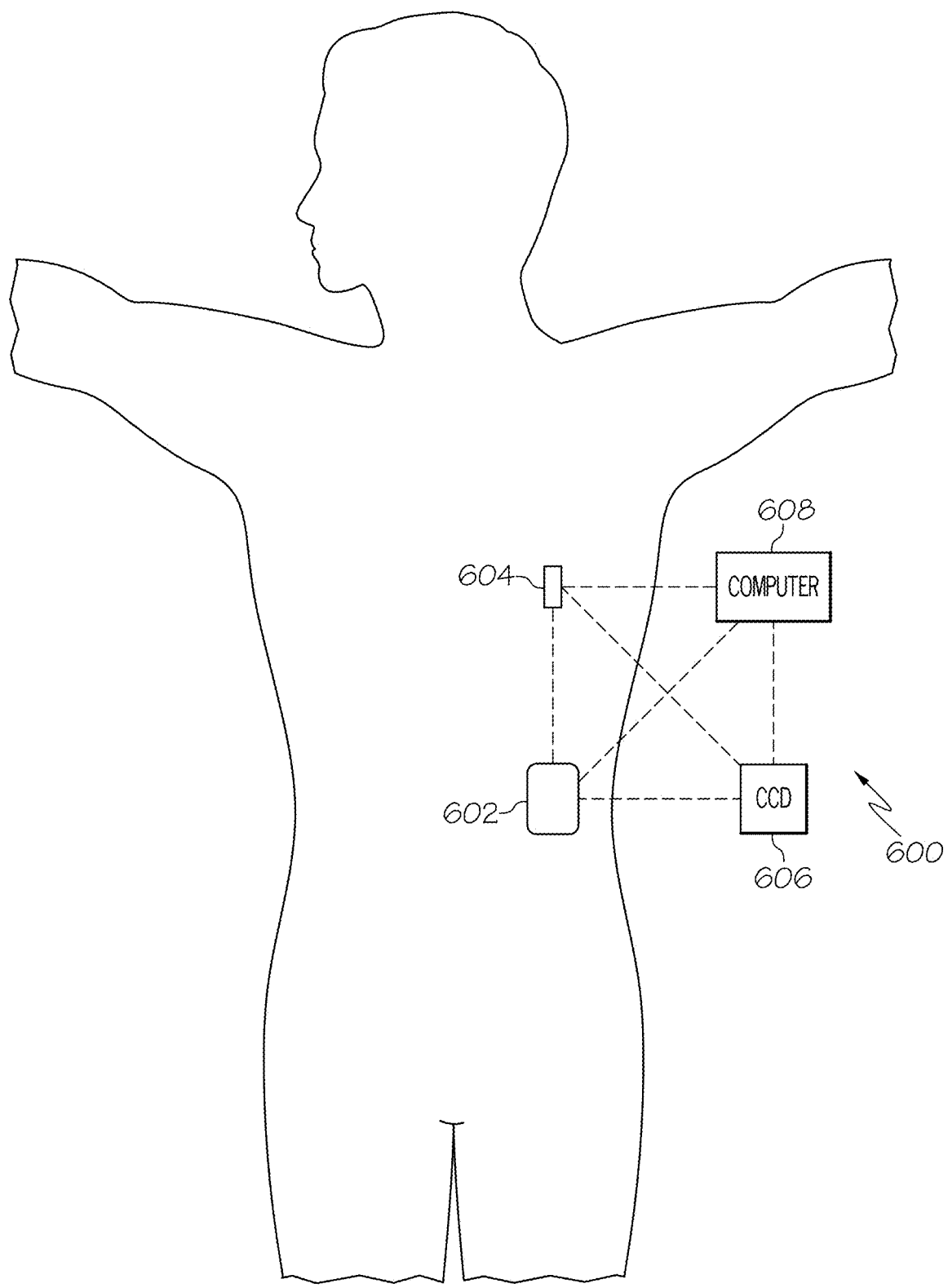
FIG. 6 depicts an exemplary embodiment of an infusion system.

FIG. 6 depicts one exemplary embodiment of an infusion system 600 that includes, without limitation, a fluid infusion device (or infusion pump) 602, a sensing arrangement 604, a command control device (CCD) 606, and a computer 608, which could be realized as any one of the computing devices 206, 210, 500, 512 described above. The components of an infusion system 600 may be realized using different platforms, designs, and configurations, and the embodiment shown in FIG. 6 is not exhaustive or limiting. In practice, the infusion device 602 and the sensing arrangement 604 are secured at desired locations on the body of a user (or patient), as illustrated in FIG. 6. In this regard, the locations at which the infusion device 602 and the sensing arrangement 604 are secured to the body of the user in FIG. 6 are provided only as a representative, non-limiting, example. The elements of the infusion system 600 may be similar to those described in U.S. Pat. No. 8,674,288, the subject matter of which is hereby incorporated by reference in its entirety.

In the illustrated embodiment of FIG. 6, the infusion device 602 is designed as a portable medical device suitable for infusing a fluid, a liquid, a gel, or other agent into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 604 generally represents the components of the infusion system 600 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 604 may include electronics and enzymes reactive to a biological or physiological condition of the user, such as a blood glucose level, or the like, and provide data indicative of the blood glucose level to the infusion device 602, the CCD 606 and/or the computer 608. For example, the infusion device 602, the CCD 606 and/or the computer 608 may include a display for presenting information or data to the user based on the sensor data received from the sensing arrangement 604, such as, for example, a current glucose level of the user, a graph or chart of the user's glucose level versus time, device status indicators, alert messages, or the like. In other embodiments, the infusion device 602, the CCD 606 and/or the computer 608 may include electronics and software that are configured to analyze sensor data and operate the infusion device 602 to deliver fluid to the body of the user based on the sensor data and/or preprogrammed delivery routines. Thus, in exemplary embodiments, one or more of the infusion device 602, the sensing arrangement 604, the CCD 606, and/or the computer 608 includes a transmitter, a receiver, and/or other transceiver electronics that allow for communication with other components of the infusion system 600, so that the sensing arrangement 604 may transmit sensor data or monitor data to one or more of the infusion device 602, the CCD 606 and/or the computer 608.

Still referring to FIG. 6, in various embodiments, the sensing arrangement 604 may be secured to the body of the user or embedded in the body of the user at a location that is remote from the location at which the infusion device 602 is secured to the body of the user. In various other embodiments, the sensing arrangement 604 may be incorporated within the infusion device 602. In other embodiments, the sensing arrangement 604 may be separate and apart from the infusion device 602, and may be, for example, part of the CCD 606. In such embodiments, the sensing arrangement 604 may be configured to receive a biological sample, analyte, or the like, to measure a condition of the user.

In various embodiments, the CCD 606 and/or the computer 608 may include electronics and other components configured to perform processing, delivery routine storage, and to control the infusion device 602 in a manner that is influenced by sensor data measured by and/or received from the sensing arrangement 604. By including control functions in the CCD 606 and/or the computer 608, the infusion device 602 may be made with more simplified electronics. However, in other embodiments, the infusion device 602 may include all control functions, and may operate without the CCD 606 and/or the computer 608. In various embodiments, the CCD 606 may be a portable electronic device. In addition, in various embodiments, the infusion device 602 and/or the sensing arrangement 604 may be configured to transmit data to the CCD 606 and/or the computer 608 for display or processing of the data by the CCD 606 and/or the computer 608.

In some embodiments, the CCD 606 and/or the computer 608 may provide information to the user that facilitates the user's subsequent use of the infusion device 602. For example, the CCD 606 may provide information to the user to allow the user to determine the rate or dose of medication to be administered into the user's body. In other embodiments, the CCD 606 may provide information to the infusion device 602 to autonomously control the rate or dose of medication administered into the body of the user. In some embodiments, the sensing arrangement 604 may be integrated into the CCD 606. Such embodiments may allow the user to monitor a condition by providing, for example, a sample of his or her blood to the sensing arrangement 604 to assess his or her condition. In some embodiments, the sensing arrangement 604 and the CCD 606 may be used for determining glucose levels in the blood and/or body fluids of the user without the use of, or necessity of, a wire or cable connection between the infusion device 602 and the sensing arrangement 604 and/or the CCD 606.

In one or more exemplary embodiments, the sensing arrangement 604 and/or the infusion device 602 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402,153, all of which are incorporated herein by reference in their entirety. In such embodiments, the sensing arrangement 604 is configured to sense or measure a condition of the user, such as, blood glucose level or the like. The infusion device 602 is configured to deliver fluid in response to the condition sensed by the sensing arrangement 604. In turn, the sensing arrangement 604 continues to sense or otherwise quantify a current condition of the user, thereby allowing the infusion device 602 to deliver fluid continuously in response to the condition currently (or most recently) sensed by the sensing arrangement 604 indefinitely. In some embodiments, the sensing arrangement 604 and/or the infusion device 602 may be configured to utilize the closed-loop system only for a portion of the day, for example only when the user is asleep or awake.

Figure 7:
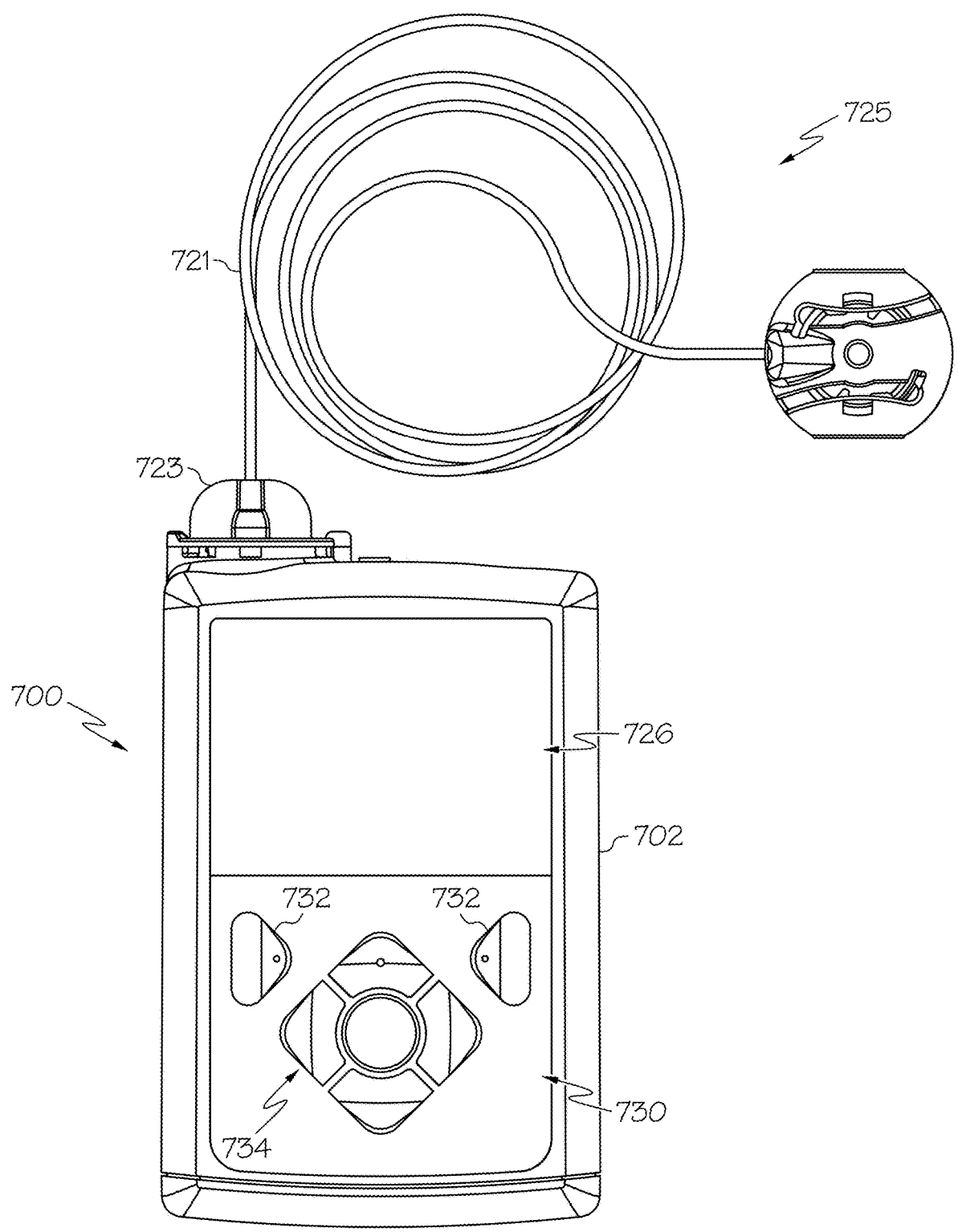
FIG. 7 depicts a plan view of an exemplary embodiment of a fluid infusion device suitable for use in the infusion system of FIG. 6.
Figure 8:
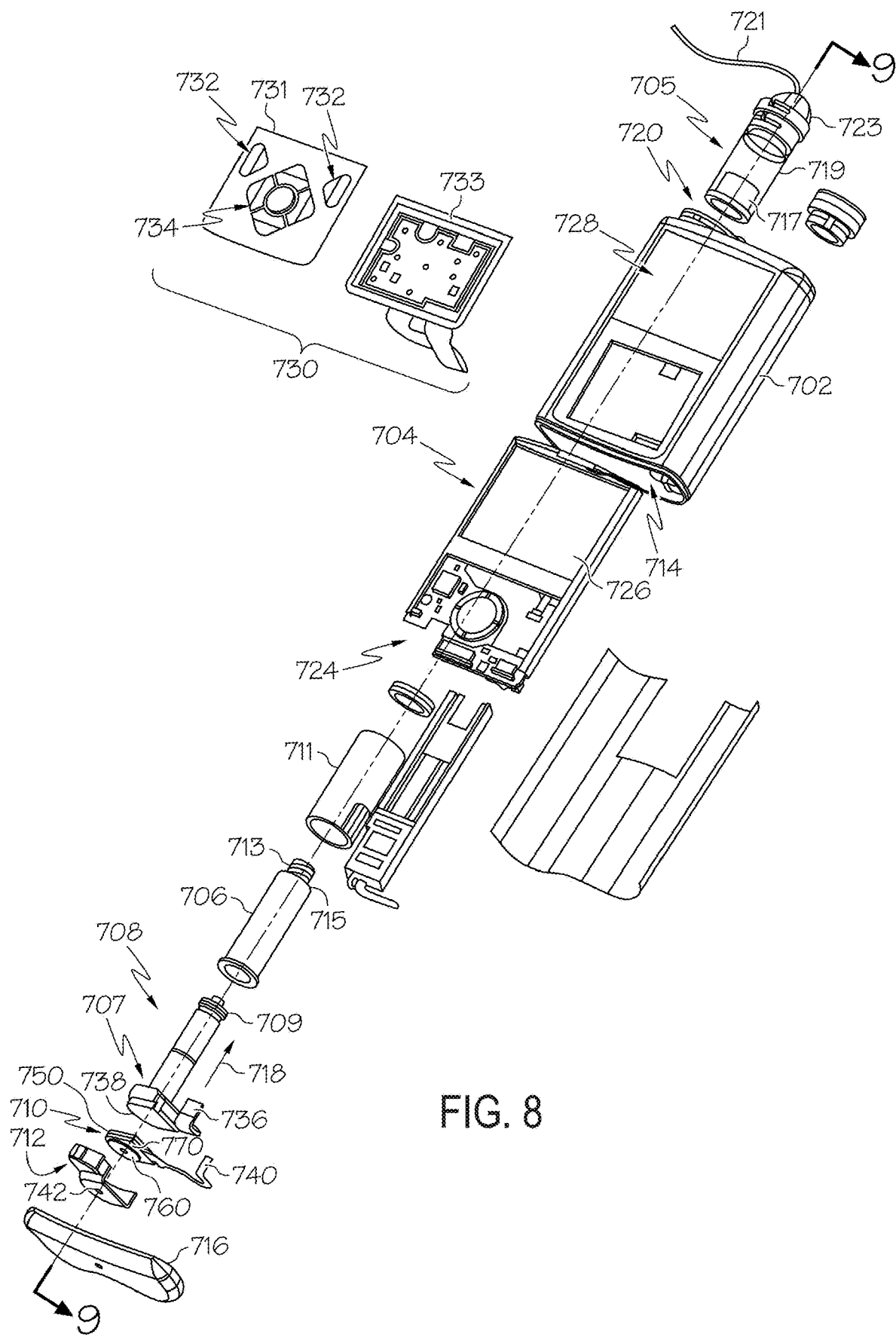
FIG. 8 is an exploded perspective view of the fluid infusion device of FIG. 7.
Figure 9:
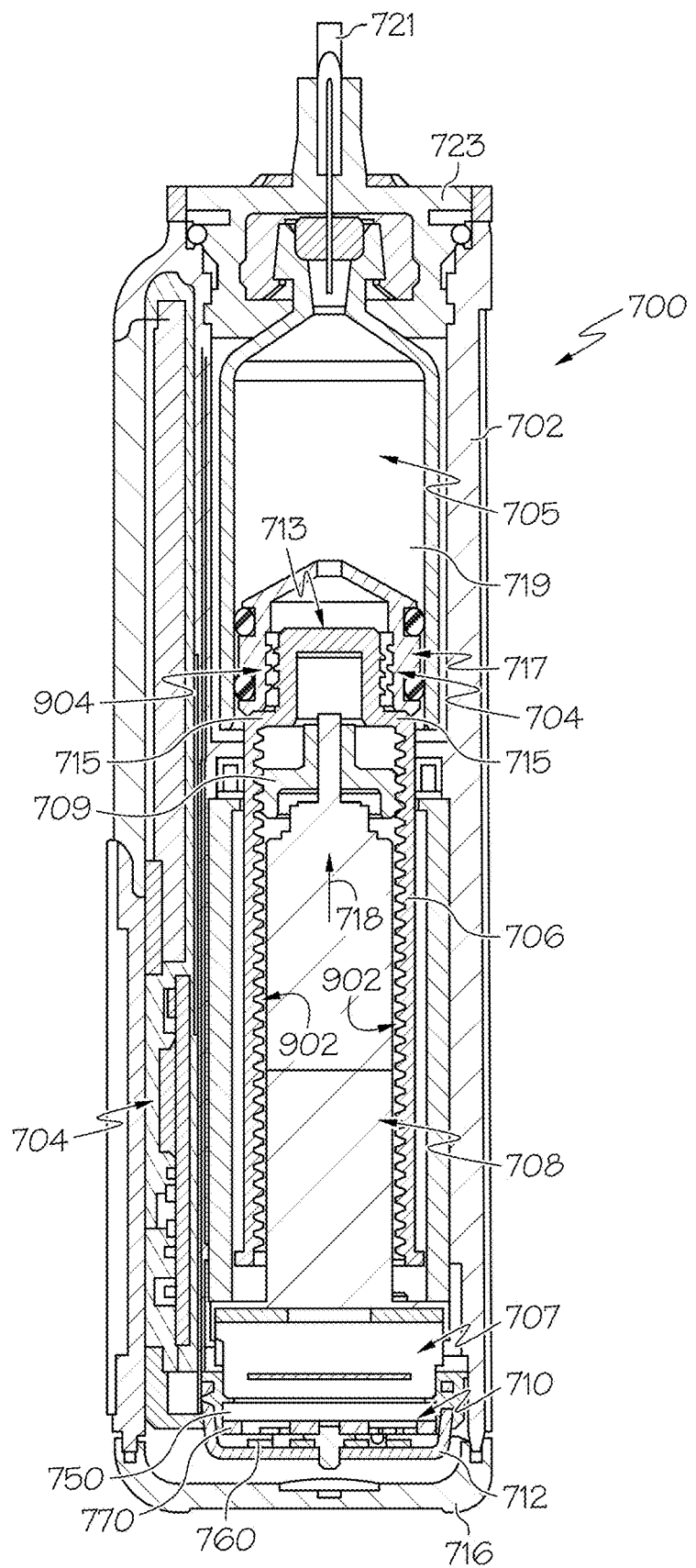
FIG. 9 is a cross-sectional view of the fluid infusion device of FIGS. 7-8 as viewed along line 9-9 in FIG. 8 when assembled with a reservoir inserted in the infusion device.

FIGS. 7-9 depict one exemplary embodiment of a fluid infusion device 700 (or alternatively, infusion pump) suitable for use in an infusion system, such as, for example, as infusion device 602 in the infusion system 600 of FIG. 6. The fluid infusion device 700 is a portable medical device designed to be carried or worn by a patient (or user), and the fluid infusion device 700 may leverage any number of conventional features, components, elements, and characteristics of existing fluid infusion devices, such as, for example, some of the features, components, elements, and/or characteristics described in U.S. Pat. Nos. 6,485,465 and 7,621,893. It should be appreciated that FIGS. 7-9 depict some aspects of the infusion device 700 in a simplified manner; in practice, the infusion device 700 could include additional elements, features, or components that are not shown or described in detail herein.

As best illustrated in FIGS. 7-8, the illustrated embodiment of the fluid infusion device 700 includes a housing 702 adapted to receive a fluid-containing reservoir 705. An opening 720 in the housing 702 accommodates a fitting 723 (or cap) for the reservoir 705, with the fitting 723 being configured to mate or otherwise interface with tubing 721 of an infusion set 725 that provides a fluid path to/from the body of the user. In this manner, fluid communication from the interior of the reservoir 705 to the user is established via the tubing 721. The illustrated fluid infusion device 700 includes a human-machine interface (HMI) 730 (or user interface) that includes elements 732, 734 that can be manipulated by the user to administer a bolus of fluid (e.g., insulin), to change therapy settings, to change user preferences, to select display features, and the like. The infusion device also includes a display element 726, such as a liquid crystal display (LCD) or another suitable display element, that can be used to present various types of information or data to the user, such as, without limitation: the current glucose level of the patient; the time; a graph or chart of the patient's glucose level versus time; device status indicators; etc.

The housing 702 is formed from a substantially rigid material having a hollow interior 714 adapted to allow an electronics assembly 704, a sliding member (or slide) 706, a drive system 708, a sensor assembly 710, and a drive system capping member 712 to be disposed therein in addition to the reservoir 705, with the contents of the housing 702 being enclosed by a housing capping member 716. The opening 720, the slide 706, and the drive system 708 are coaxially aligned in an axial direction (indicated by arrow 718), whereby the drive system 708 facilitates linear displacement of the slide 706 in the axial direction 718 to dispense fluid from the reservoir 705 (after the reservoir 705 has been inserted into opening 720), with the sensor assembly 710 being configured to measure axial forces (e.g., forces aligned with the axial direction 718) exerted on the sensor assembly 710 responsive to operating the drive system 708 to displace the slide 706. In various embodiments, the sensor assembly 710 may be utilized to detect one or more of the following: an occlusion in a fluid path that slows, prevents, or otherwise degrades fluid delivery from the reservoir 705 to a user's body; when the reservoir 705 is empty; when the slide 706 is properly seated with the reservoir 705; when a fluid dose has been delivered; when the infusion pump 700 is subjected to shock or vibration; when the infusion pump 700 requires maintenance.

Depending on the embodiment, the fluid-containing reservoir 705 may be realized as a syringe, a vial, a cartridge, a bag, or the like. In certain embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. As best illustrated in FIGS. 8-9, the reservoir 705 typically includes a reservoir barrel 719 that contains the fluid and is concentrically and/or coaxially aligned with the slide 706 (e.g., in the axial direction 718) when the reservoir 705 is inserted into the infusion pump 700. The end of the reservoir 705 proximate the opening 720 may include or otherwise mate with the fitting 723, which secures the reservoir 705 in the housing 702 and prevents displacement of the reservoir 705 in the axial direction 718 with respect to the housing 702 after the reservoir 705 is inserted into the housing 702. As described above, the fitting 723 extends from (or through) the opening 720 of the housing 702 and mates with tubing 721 to establish fluid communication from the interior of the reservoir 705 (e.g., reservoir barrel 719) to the user via the tubing 721 and infusion set 725. The opposing end of the reservoir 705 proximate the slide 706 includes a plunger 717 (or stopper) positioned to push fluid from inside the barrel 719 of the reservoir 705 along a fluid path through tubing 721 to a user. The slide 706 is configured to mechanically couple or otherwise engage with the plunger 717, thereby becoming seated with the plunger 717 and/or reservoir 705. Fluid is forced from the reservoir 705 via tubing 721 as the drive system 708 is operated to displace the slide 706 in the axial direction 718 toward the opening 720 in the housing 702.

In the illustrated embodiment of FIGS. 8-9, the drive system 708 includes a motor assembly 707 and a drive screw 709. The motor assembly 707 includes a motor that is coupled to drive train components of the drive system 708 that are configured to convert rotational motor motion to a translational displacement of the slide 706 in the axial direction 718, and thereby engaging and displacing the plunger 717 of the reservoir 705 in the axial direction 718. In some embodiments, the motor assembly 707 may also be powered to translate the slide 706 in the opposing direction (e.g., the direction opposite direction 718) to retract and/or detach from the reservoir 705 to allow the reservoir 705 to be replaced. In exemplary embodiments, the motor assembly 707 includes a brushless DC (BLDC) motor having one or more permanent magnets mounted, affixed, or otherwise disposed on its rotor. However, the subject matter described herein is not necessarily limited to use with BLDC motors, and in alternative embodiments, the motor may be realized as a solenoid motor, an AC motor, a stepper motor, a piezoelectric caterpillar drive, a shape memory actuator drive, an electrochemical gas cell, a thermally driven gas cell, a bimetallic actuator, or the like. The drive train components may comprise one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. In this regard, although the illustrated embodiment of the infusion pump utilizes a coaxially aligned drive train, the motor could be arranged in an offset or otherwise non-coaxial manner, relative to the longitudinal axis of the reservoir 705.

As best shown in FIG. 9, the drive screw 709 mates with threads 902 internal to the slide 706. When the motor assembly 707 is powered and operated, the drive screw 709 rotates, and the slide 706 is forced to translate in the axial direction 718. In an exemplary embodiment, the infusion pump 700 includes a sleeve 711 to prevent the slide 706 from rotating when the drive screw 709 of the drive system 708 rotates. Thus, rotation of the drive screw 709 causes the slide 706 to extend or retract relative to the drive motor assembly 707. When the fluid infusion device is assembled and operational, the slide 706 contacts the plunger 717 to engage the reservoir 705 and control delivery of fluid from the infusion pump 700. In an exemplary embodiment, the shoulder portion 715 of the slide 706 contacts or otherwise engages the plunger 717 to displace the plunger 717 in the axial direction 718. In alternative embodiments, the slide 706 may include a threaded tip 713 capable of being detachably engaged with internal threads 904 on the plunger 717 of the reservoir 705, as described in detail in U.S. Pat. Nos. 6,248,093 and 6,485,465, which are incorporated by reference herein.

As illustrated in FIG. 8, the electronics assembly 704 includes control electronics 724 coupled to the display element 726, with the housing 702 including a transparent window portion 728 that is aligned with the display element 726 to allow the display 726 to be viewed by the user when the electronics assembly 704 is disposed within the interior 714 of the housing 702. The control electronics 724 generally represent the hardware, firmware, processing logic and/or software (or combinations thereof) configured to control operation of the motor assembly 707 and/or drive system 708, as described in greater detail below in the context of FIG. 10. Whether such functionality is implemented as hardware, firmware, a state machine, or software depends upon the particular application and design constraints imposed on the embodiment. Those familiar with the concepts described here may implement such functionality in a suitable manner for each particular application, but such implementation decisions should not be interpreted as being restrictive or limiting. In an exemplary embodiment, the control electronics 724 includes one or more programmable controllers that may be programmed to control operation of the infusion pump 700.

The motor assembly 707 includes one or more electrical leads 736 adapted to be electrically coupled to the electronics assembly 704 to establish communication between the control electronics 724 and the motor assembly 707. In response to command signals from the control electronics 724 that operate a motor driver (e.g., a power converter) to regulate the amount of power supplied to the motor from a power supply, the motor actuates the drive train components of the drive system 708 to displace the slide 706 in the axial direction 718 to force fluid from the reservoir 705 along a fluid path (including tubing 721 and an infusion set), thereby administering doses of the fluid contained in the reservoir 705 into the user's body. Preferably, the power supply is realized one or more batteries contained within the housing 702. Alternatively, the power supply may be a solar panel, capacitor, AC or DC power supplied through a power cord, or the like. In some embodiments, the control electronics 724 may operate the motor of the motor assembly 707 and/or drive system 708 in a stepwise manner, typically on an intermittent basis; to administer discrete precise doses of the fluid to the user according to programmed delivery profiles.

Referring to FIGS. 7-9, as described above, the user interface 730 includes HMI elements, such as buttons 732 and a directional pad 734, that are formed on a graphic keypad overlay 731 that overlies a keypad assembly 733, which includes features corresponding to the buttons 732, directional pad 734 or other user interface items indicated by the graphic keypad overlay 731. When assembled, the keypad assembly 733 is coupled to the control electronics 724, thereby allowing the HMI elements 732, 734 to be manipulated by the user to interact with the control electronics 724 and control operation of the infusion pump 700, for example, to administer a bolus of insulin, to change therapy settings, to change user preferences, to select display features, to set or disable alarms and reminders, and the like. In this regard, the control electronics 724 maintains and/or provides information to the display 726 regarding program parameters, delivery profiles, pump operation, alarms, warnings, statuses, or the like, which may be adjusted using the HMI elements 732, 734. In various embodiments, the HMI elements 732, 734 may be realized as physical objects (e.g., buttons, knobs, joysticks, and the like) or virtual objects (e.g., using touch-sensing and/or proximity-sensing technologies). For example, in some embodiments, the display 726 may be realized as a touch screen or touch-sensitive display, and in such embodiments, the features and/or functionality of the HMI elements 732, 734 may be integrated into the display 726 and the HMI 730 may not be present. In some embodiments, the electronics assembly 704 may also include alert generating elements coupled to the control electronics 724 and suitably configured to generate one or more types of feedback, such as, without limitation: audible feedback; visual feedback; haptic (physical) feedback; or the like.

Referring to FIGS. 8-9, in accordance with one or more embodiments, the sensor assembly 710 includes a back plate structure 750 and a loading element 760. The loading element 760 is disposed between the capping member 712 and a beam structure 770 that includes one or more beams having sensing elements disposed thereon that are influenced by compressive force applied to the sensor assembly 710 that deflects the one or more beams, as described in greater detail in U.S. Pat. No. 8,474,332, which is incorporated by reference herein. In exemplary embodiments, the back plate structure 750 is affixed, adhered, mounted, or otherwise mechanically coupled to the bottom surface 738 of the drive system 708 such that the back plate structure 750 resides between the bottom surface 738 of the drive system 708 and the housing cap 716. The drive system capping member 712 is contoured to accommodate and conform to the bottom of the sensor assembly 710 and the drive system 708. The drive system capping member 712 may be affixed to the interior of the housing 702 to prevent displacement of the sensor assembly 710 in the direction opposite the direction of force provided by the drive system 708 (e.g., the direction opposite direction 718). Thus, the sensor assembly 710 is positioned between the motor assembly 707 and secured by the capping member 712, which prevents displacement of the sensor assembly 710 in a downward direction opposite the direction of arrow 718, such that the sensor assembly 710 is subjected to a reactionary compressive force when the drive system 708 and/or motor assembly 707 is operated to displace the slide 706 in the axial direction 718 in opposition to the fluid pressure in the reservoir 705. Under normal operating conditions, the compressive force applied to the sensor assembly 710 is correlated with the fluid pressure in the reservoir 705. As shown, electrical leads 740 are adapted to electrically couple the sensing elements of the sensor assembly 710 to the electronics assembly 704 to establish communication to the control electronics 724, wherein the control electronics 724 are configured to measure, receive, or otherwise obtain electrical signals from the sensing elements of the sensor assembly 710 that are indicative of the force applied by the drive system 708 in the axial direction 718.

Figure 10:
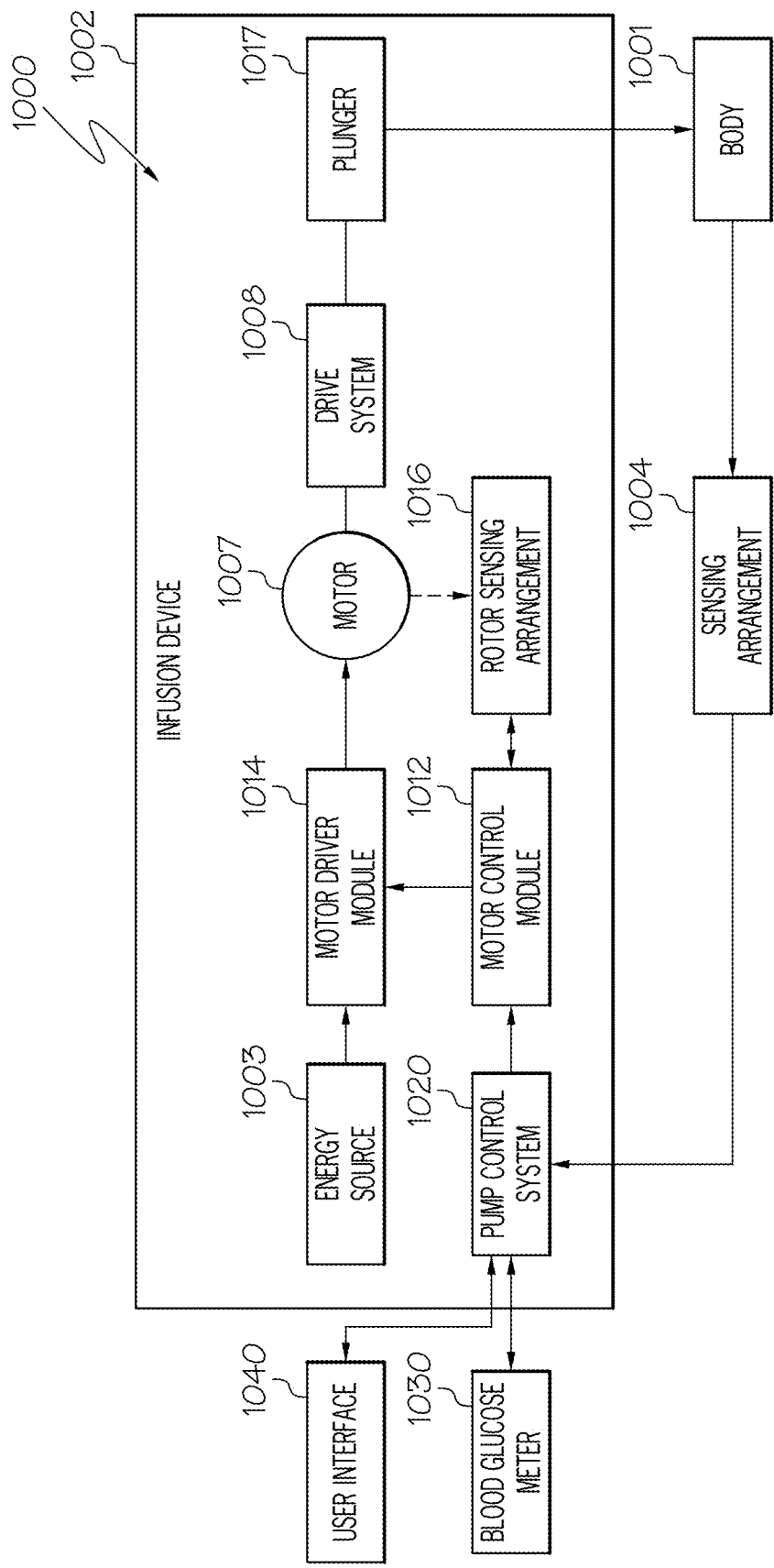
FIG. 10 is a block diagram of an exemplary control system suitable for use in a fluid infusion device, such as the fluid infusion device of FIG. 2, 6 or 7.

FIG. 10 depicts an exemplary embodiment of a control system 1000 suitable for use with an infusion device 1002, such as any one of the infusion devices 202, 602, 700 described above. The control system 1000 is capable of controlling or otherwise regulating a physiological condition in the body 1001 of a user to a desired (or target) value or otherwise maintain the condition within a range of acceptable values in an automated or autonomous manner. In one or more exemplary embodiments, the condition being regulated is sensed, detected, measured or otherwise quantified by a sensing arrangement 1004 (e.g., sensing arrangement 604) communicatively coupled to the infusion device 1002. However, it should be noted that in alternative embodiments, the condition being regulated by the control system 1000 may be correlative to the measured values obtained by the sensing arrangement 1004. That said, for clarity and purposes of explanation, the subject matter may be described herein in the context of the sensing arrangement 1004 being realized as a glucose sensing arrangement that senses, detects, measures or otherwise quantifies the user's glucose level, which is being regulated in the body 1001 of the user by the control system 1000.

In exemplary embodiments, the sensing arrangement 1004 includes one or more interstitial glucose sensing elements that generate or otherwise output electrical signals having a signal characteristic that is correlative to, influenced by, or otherwise indicative of the relative interstitial fluid glucose level in the body 1001 of the user. The output electrical signals are filtered or otherwise processed to obtain a measurement value indicative of the user's interstitial fluid glucose level. In exemplary embodiments, a blood glucose meter 1030, such as a finger stick device, is utilized to directly sense, detect, measure or otherwise quantify the blood glucose in the body 1001 of the user. In this regard, the blood glucose meter 1030 outputs or otherwise provides a measured blood glucose value that may be utilized as a reference measurement for calibrating the sensing arrangement 1004 and converting a measurement value indicative of the user's interstitial fluid glucose level into a corresponding calibrated blood glucose value. For purposes of explanation, the calibrated blood glucose value calculated based on the electrical signals output by the sensing element(s) of the sensing arrangement 1004 may alternatively be referred to herein as the sensor glucose value, the sensed glucose value, or variants thereof.

In the illustrated embodiment, the pump control system 1020 generally represents the electronics and other components of the infusion device 1002 that control operation of the fluid infusion device 1002 according to a desired infusion delivery program in a manner that is influenced by the sensed glucose value indicative of a current glucose level in the body 1001 of the user. For example, to support a closed-loop operating mode, the pump control system 1020 maintains, receives, or otherwise obtains a target or commanded glucose value, and automatically generates or otherwise determines dosage commands for operating an actuation arrangement, such as a motor 1007, to displace the plunger 1017 and deliver insulin to the body 1001 of the user based on the difference between a sensed glucose value and the target glucose value. In other operating modes, the pump control system 1020 may generate or otherwise determine dosage commands configured to maintain the sensed glucose value below an upper glucose limit, above a lower glucose limit, or otherwise within a desired range of glucose values. In practice, the infusion device 1002 may store or otherwise maintain the target value, upper and/or lower glucose limit(s), and/or other glucose threshold value(s) in a data storage element accessible to the pump control system 1020.

The target glucose value and other threshold glucose values may be received from an external component (e.g., CCD 606 and/or computing device 608) or be input by a user via a user interface element 1040 associated with the infusion device 1002. In practice, the one or more user interface element(s) 1040 associated with the infusion device 1002 typically include at least one input user interface element, such as, for example, a button, a keypad, a keyboard, a knob, a joystick, a mouse, a touch panel, a touchscreen, a microphone or another audio input device, and/or the like. Additionally, the one or more user interface element(s) 1040 include at least one output user interface element, such as, for example, a display element (e.g., a light-emitting diode or the like), a display device (e.g., a liquid crystal display or the like), a speaker or another audio output device, a haptic feedback device, or the like, for providing notifications or other information to the user. It should be noted that although FIG. 10 depicts the user interface element(s) 1040 as being separate from the infusion device 1002, in practice, one or more of the user interface element(s) 1040 may be integrated with the infusion device 1002. Furthermore, in some embodiments, one or more user interface element(s) 1040 are integrated with the sensing arrangement 1004 in addition to and/or in alternative to the user interface element(s) 1040 integrated with the infusion device 1002. The user interface element(s) 1040 may be manipulated by the user to operate the infusion device 1002 to deliver correction boluses, adjust target and/or threshold values, modify the delivery control scheme or operating mode, and the like, as desired.

Still referring to FIG. 10, in the illustrated embodiment, the infusion device 1002 includes a motor control module 1012 coupled to a motor 1007 (e.g., motor assembly 707) that is operable to displace a plunger 1017 (e.g., plunger 717) in a reservoir (e.g., reservoir 705) and provide a desired amount of fluid to the body 1001 of a user. In this regard, displacement of the plunger 1017 results in the delivery of a fluid that is capable of influencing the condition in the body 1001 of the user to the body 1001 of the user via a fluid delivery path (e.g., via tubing 721 of an infusion set 725). A motor driver module 1014 is coupled between an energy source 1003 and the motor 1007. The motor control module 1012 is coupled to the motor driver module 1014, and the motor control module 1012 generates or otherwise provides command signals that operate the motor driver module 1014 to provide current (or power) from the energy source 1003 to the motor 1007 to displace the plunger 1017 in response to receiving, from a pump control system 1020, a dosage command indicative of the desired amount of fluid to be delivered.

In exemplary embodiments, the energy source 1003 is realized as a battery housed within the infusion device 1002 (e.g., within housing 702) that provides direct current (DC) power. In this regard, the motor driver module 1014 generally represents the combination of circuitry, hardware and/or other electrical components configured to convert or otherwise transfer DC power provided by the energy source 1003 into alternating electrical signals applied to respective phases of the stator windings of the motor 1007 that result in current flowing through the stator windings that generates a stator magnetic field and causes the rotor of the motor 1007 to rotate. The motor control module 1012 is configured to receive or otherwise obtain a commanded dosage from the pump control system 1020, convert the commanded dosage to a commanded translational displacement of the plunger 1017, and command, signal, or otherwise operate the motor driver module 1014 to cause the rotor of the motor 1007 to rotate by an amount that produces the commanded translational displacement of the plunger 1017. For example, the motor control module 1012 may determine an amount of rotation of the rotor required to produce translational displacement of the plunger 1017 that achieves the commanded dosage received from the pump control system 1020. Based on the current rotational position (or orientation) of the rotor with respect to the stator that is indicated by the output of the rotor sensing arrangement 1016, the motor control module 1012 determines the appropriate sequence of alternating electrical signals to be applied to the respective phases of the stator windings that should rotate the rotor by the determined amount of rotation from its current position (or orientation). In embodiments where the motor 1007 is realized as a BLDC motor, the alternating electrical signals commutate the respective phases of the stator windings at the appropriate orientation of the rotor magnetic poles with respect to the stator and in the appropriate order to provide a rotating stator magnetic field that rotates the rotor in the desired direction. Thereafter, the motor control module 1012 operates the motor driver module 1014 to apply the determined alternating electrical signals (e.g., the command signals) to the stator windings of the motor 1007 to achieve the desired delivery of fluid to the user.

When the motor control module 1012 is operating the motor driver module 1014, current flows from the energy source 1003 through the stator windings of the motor 1007 to produce a stator magnetic field that interacts with the rotor magnetic field. In some embodiments, after the motor control module 1012 operates the motor driver module 1014 and/or motor 1007 to achieve the commanded dosage, the motor control module 1012 ceases operating the motor driver module 1014 and/or motor 1007 until a subsequent dosage command is received. In this regard, the motor driver module 1014 and the motor 1007 enter an idle state during which the motor driver module 1014 effectively disconnects or isolates the stator windings of the motor 1007 from the energy source 1003. In other words, current does not flow from the energy source 1003 through the stator windings of the motor 1007 when the motor 1007 is idle, and thus, the motor 1007 does not consume power from the energy source 1003 in the idle state, thereby improving efficiency.

Depending on the embodiment, the motor control module 1012 may be implemented or realized with a general-purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In exemplary embodiments, the motor control module 1012 includes or otherwise accesses a data storage element or memory, including any sort of random access memory (RAM), read only memory (ROM), flash memory, registers, hard disks, removable disks, magnetic or optical mass storage, or any other short or long-term storage media or other non-transitory computer-readable medium, which is capable of storing programming instructions for execution by the motor control module 1012. The computer-executable programming instructions, when read and executed by the motor control module 1012, cause the motor control module 1012 to perform or otherwise support the tasks, operations, functions, and processes described herein.

It should be appreciated that FIG. 10 is a simplified representation of the infusion device 1002 for purposes of explanation and is not intended to limit the subject matter described herein in any way. In this regard, depending on the embodiment, some features and/or functionality of the sensing arrangement 1004 may be implemented by or otherwise integrated into the pump control system 1020, or vice versa. Similarly, in practice, the features and/or functionality of the motor control module 1012 may be implemented by or otherwise integrated into the pump control system 1020, or vice versa. Furthermore, the features and/or functionality of the pump control system 1020 may be implemented by control electronics 724 located in the fluid infusion device 700, while in alternative embodiments, the pump control system 1020 may be implemented by a remote computing device that is physically distinct and/or separate from the infusion device 1002, such as, for example, the CCD 606 or the computing device 608.

Figure 11:
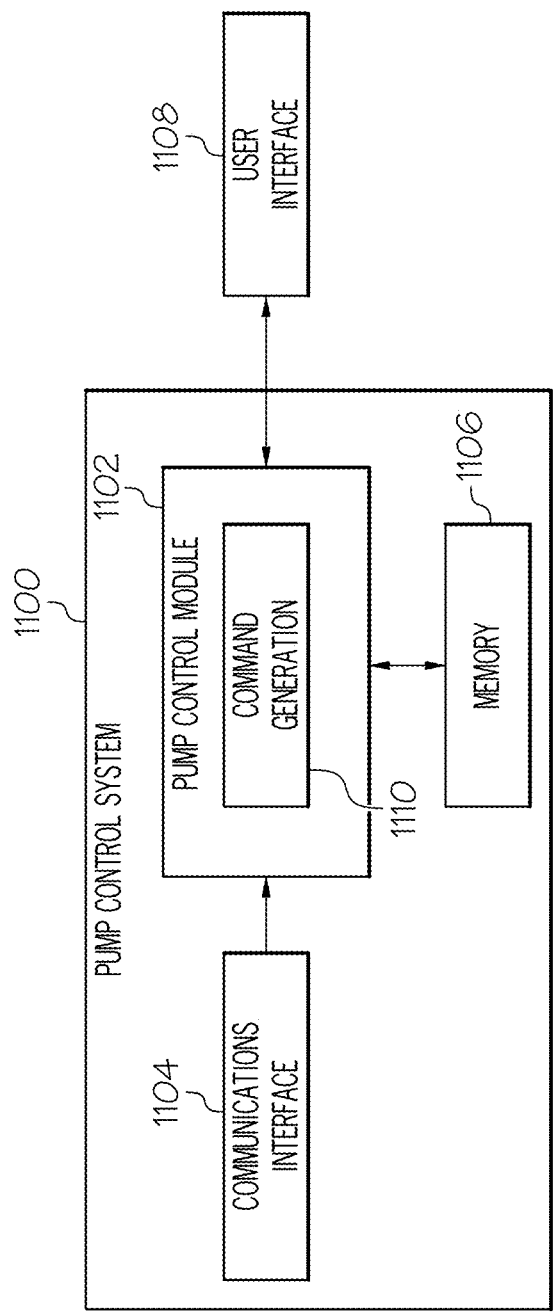
FIG. 11 is a block diagram of an exemplary pump control system suitable for use in the control system of FIG. 10.

FIG. 11 depicts an exemplary embodiment of a pump control system 1100 suitable for use as the pump control system 1020 in FIG. 10 in accordance with one or more embodiments. The illustrated pump control system 1100 includes, without limitation, a pump control module 1102, a communications interface 1104, and a data storage element (or memory) 1106. The pump control module 1102 is coupled to the communications interface 1104 and the memory 1106, and the pump control module 1102 is suitably configured to support the operations, tasks, and/or processes described herein. In exemplary embodiments, the pump control module 1102 is also coupled to one or more user interface elements 1108 (e.g., user interface 730, 1040) for receiving user input and providing notifications, alerts, or other therapy information to the user. Although FIG. 11 depicts the user interface element 1108 as being separate from the pump control system 1100, in various alternative embodiments, the user interface element 1108 may be integrated with the pump control system 1100 (e.g., as part of the infusion device 700, 1002), the sensing arrangement 1004 or another element of an infusion system 600 (e.g., the computer 608 or CCD 606).

Referring to FIG. 11 and with reference to FIG. 10, the communications interface 1104 generally represents the hardware, circuitry, logic, firmware and/or other components of the pump control system 1100 that are coupled to the pump control module 1102 and configured to support communications between the pump control system 1100 and the sensing arrangement 1004. In this regard, the communications interface 1104 may include or otherwise be coupled to one or more transceiver modules capable of supporting wireless communications between the pump control system 1020, 1100 and the sensing arrangement 1004 or another electronic device 206, 210, 500, 512, 606, 608 in an infusion system 600 or a management system 200, 516. For example, the communications interface 1104 may be utilized to receive sensor measurement values or other measurement data from a sensing arrangement 604, 1004 as well as upload such sensor measurement values to a server 206 or other computing device 210, 500, 512, 1008 for purposes of generating a report including a snapshot GUI display as described above in the context of FIGS. 1-6. In other embodiments, the communications interface 1104 may be configured to support wired communications to/from the sensing arrangement 1004.

The pump control module 1102 generally represents the hardware, circuitry, logic, firmware and/or other component of the pump control system 1100 that is coupled to the communications interface 1104 and configured to determine dosage commands for operating the motor 1007 to deliver fluid to the body 1001 based on data received from the sensing arrangement 1004 and perform various additional tasks, operations, functions and/or operations described herein. For example, in exemplary embodiments, pump control module 1102 implements or otherwise executes a command generation application 1110 that supports one or more autonomous operating modes and calculates or otherwise determines dosage commands for operating the motor 1007 of the infusion device 1002 in an autonomous operating mode based at least in part on a current measurement value for a condition in the body 1001 of the user. For example, in a closed-loop operating mode, the command generation application 1110 may determine a dosage command for operating the motor 1007 to deliver insulin to the body 1001 of the user based at least in part on the current glucose measurement value most recently received from the sensing arrangement 1004 to regulate the user's blood glucose level to a target reference glucose value. Additionally, the command generation application 610 may generate dosage commands for boluses that are manually-initiated or otherwise instructed by a user via a user interface element 1108.

Still referring to FIG. 11, depending on the embodiment, the pump control module 1102 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the pump control module 1102, or in any practical combination thereof. In exemplary embodiments, the pump control module 1102 includes or otherwise accesses the data storage element or memory 1106, which may be realized using any sort of non-transitory computer-readable medium capable of storing programming instructions for execution by the pump control module 1102. The computer-executable programming instructions, when read and executed by the pump control module 1102, cause the pump control module 1102 to implement or otherwise generate the command generation application 1110 and perform the tasks, operations, functions, and processes described in greater detail below.

It should be understood that FIG. 11 is a simplified representation of a pump control system 1100 for purposes of explanation and is not intended to limit the subject matter described herein in any way. For example, in some embodiments, the features and/or functionality of the motor control module 1012 may be implemented by or otherwise integrated into the pump control system 1100 and/or the pump control module 1102, for example, by the command generation application 1110 converting the dosage command into a corresponding motor command, in which case, the separate motor control module 1012 may be absent from an embodiment of the infusion device 1002.

Figure 12:
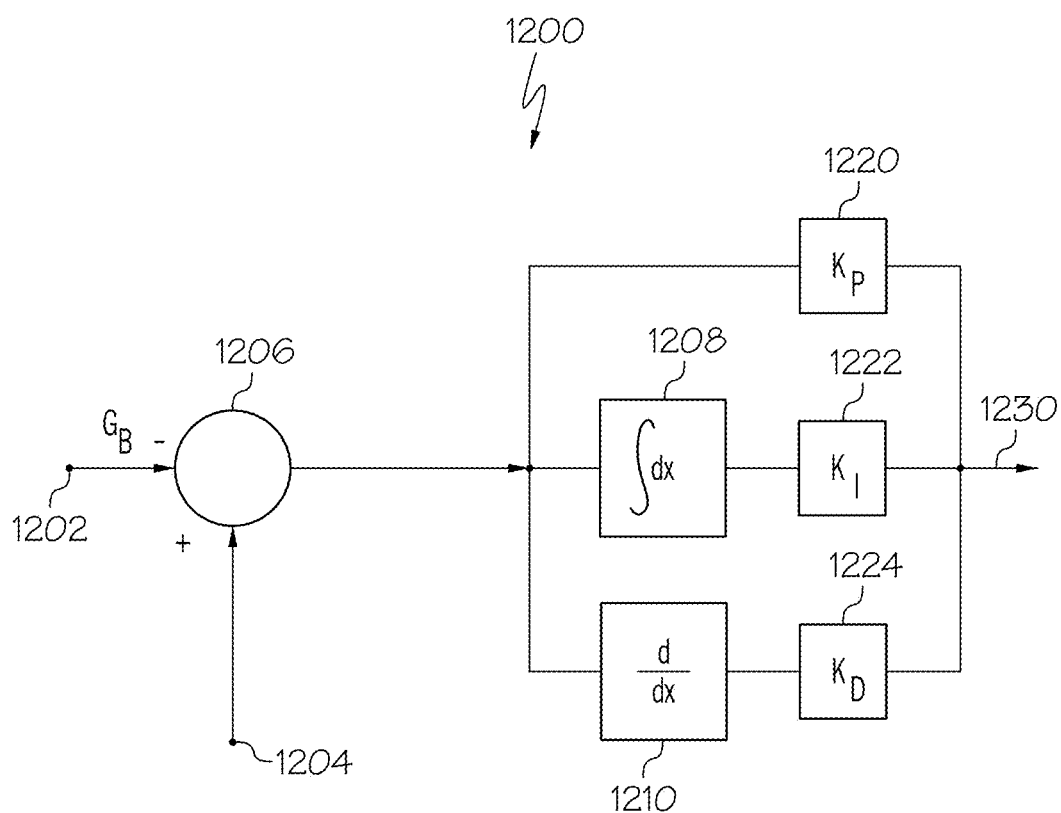
FIG. 12 is a block diagram of a closed-loop control system that may be implemented or otherwise supported by the pump control system in the fluid infusion device of FIG. 10 in one or more exemplary embodiments.

FIG. 12 depicts an exemplary closed-loop control system 1200 that may be implemented by a pump control system 1020, 1100 to provide a closed-loop operating mode that autonomously regulates a condition in the body of a user to a reference (or target) value. It should be appreciated that FIG. 12 is a simplified representation of the control system 1200 for purposes of explanation and is not intended to limit the subject matter described herein in any way.

In exemplary embodiments, the control system 1200 receives or otherwise obtains a target glucose value at input 1202. In some embodiments, the target glucose value may be stored or otherwise maintained by the infusion device 1002 (e.g., in memory 1106), however, in some alternative embodiments, the target value may be received from an external component (e.g., CCD 606 and/or computer 608). In one or more embodiments, the target glucose value may be dynamically calculated or otherwise determined prior to entering the closed-loop operating mode based on one or more patient-specific control parameters. For example, the target blood glucose value may be calculated based at least in part on a patient-specific reference basal rate and a patient-specific daily insulin requirement, which are determined based on historical delivery information over a preceding interval of time (e.g., the amount of insulin delivered over the preceding 24 hours). The control system 1200 also receives or otherwise obtains a current glucose measurement value (e.g., the most recently obtained sensor glucose value) from the sensing arrangement 1004 at input 1204. The illustrated control system 1200 implements or otherwise provides proportional-integral-derivative (PID) control to determine or otherwise generate delivery commands for operating the motor 1007 based at least in part on the difference between the target glucose value and the current glucose measurement value. In this regard, the PID control attempts to minimize the difference between the measured value and the target value, and thereby regulates the measured value to the desired value. PID control parameters are applied to the difference between the target glucose level at input 1202 and the measured glucose level at input 1204 to generate or otherwise determine a dosage (or delivery) command provided at output 1230. Based on that delivery command, the motor control module 1012 operates the motor 1007 to deliver insulin to the body of the user to influence the user's glucose level, and thereby reduce the difference between a subsequently measured glucose level and the target glucose level.

The illustrated control system 1200 includes or otherwise implements a summation block 1206 configured to determine a difference between the target value obtained at input 1202 and the measured value obtained from the sensing arrangement 1004 at input 1204, for example, by subtracting the target value from the measured value. The output of the summation block 1206 represents the difference between the measured and target values, which is then provided to each of a proportional term path, an integral term path, and a derivative term path. The proportional term path includes a gain block 1220 that multiplies the difference by a proportional gain coefficient, KP, to obtain the proportional term. The integral term path includes an integration block 1208 that integrates the difference and a gain block 1222 that multiplies the integrated difference by an integral gain coefficient, to obtain the integral term. The derivative term path includes a derivative block 1210 that determines the derivative of the difference and a gain block 1224 that multiplies the derivative of the difference by a derivative gain coefficient, $K_D$, to obtain the derivative term. The proportional term, the integral term, and the derivative term are then added or otherwise combined to obtain a delivery command that is utilized to operate the motor at output 1230. Various implementation details pertaining to closed-loop PID control and determine gain coefficients are described in greater detail in U.S. Pat. No. 7,402,153, which is incorporated by reference.

In one or more exemplary embodiments, the PID gain coefficients are user-specific (or patient-specific) and dynamically calculated or otherwise determined prior to entering the closed-loop operating mode based on historical insulin delivery information (e.g., amounts and/or timings of previous dosages, historical correction bolus information, or the like), historical sensor measurement values, historical reference blood glucose measurement values, user-reported or user-input events (e.g., meals, exercise, and the like), and the like. In this regard, one or more patient-specific control parameters (e.g., an insulin sensitivity factor, a daily insulin requirement, an insulin limit, a reference basal rate, a reference fasting glucose, an active insulin action duration, pharmodynamical time constants, or the like) may be utilized to compensate, correct, or otherwise adjust the PID gain coefficients to account for various operating conditions experienced and/or exhibited by the infusion device 1002. The PID gain coefficients may be maintained by the memory 1106 accessible to the pump control module 1102. In this regard, the memory 1106 may include a plurality of registers associated with the control parameters for the PID control. For example, a first parameter register may store the target glucose value and be accessed by or otherwise coupled to the summation block 1206 at input 1202, and similarly, a second parameter register accessed by the proportional gain block 1220 may store the proportional gain coefficient, a third parameter register accessed by the integration gain block 1222 may store the integration gain coefficient, and a fourth parameter register accessed by the derivative gain block 1224 may store the derivative gain coefficient.

Therapeutic Recommendations for Event Pattern Mitigation

As described in greater detail below, in exemplary embodiments, at least one of the detected event patterns presented in a snapshot GUI display is analyzed to determine one or more recommended remedial actions for addressing the detected event pattern. In this regard, based on the type of event pattern detected, the patient's current therapy regimen, and the patient's physiological condition, recommended modifications or adjustments to the patient's current therapy regimen may be determined and indicated on the snapshot GUI display. In one or more embodiments, logic rules or formula are maintained and utilized to determine how the patient's current therapy regimen should be modified given the patient's current therapy configuration, the patient's physiological condition, the event pattern type, and potentially other patient-specific variables or factors (e.g., the monitoring period associated with the event pattern, the severity or frequency of events, and the like). Thus, the recommended remedial actions may vary depending on the patient's current therapy regimen and dosages, the patient's A1C or glucose levels, the type of event pattern detected, and so on.

Figure 13:
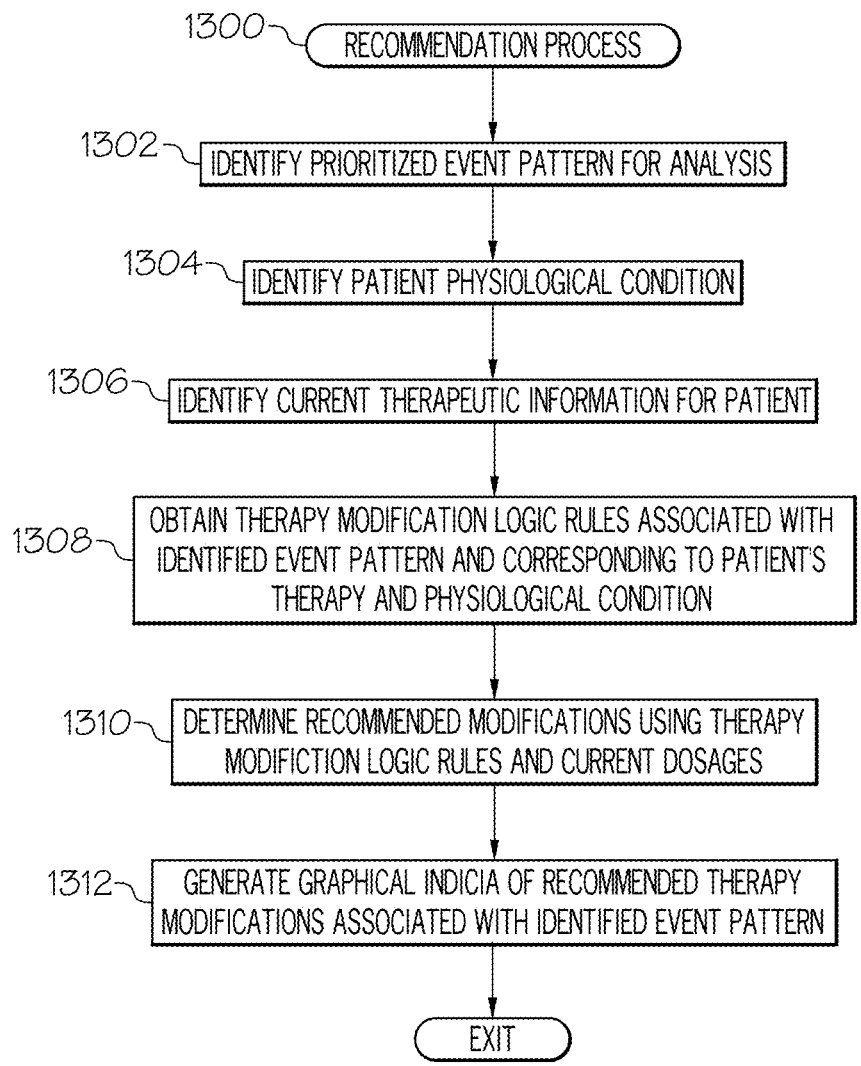
FIG. 13 is a flow diagram of an exemplary recommendation process suitable for use with the patient management system of FIG. 2 to recommend remedial actions in conjunction with the snapshot presentation process of FIG. 3 or the pattern guidance presentation process of FIG. 4.

FIG. 13 depicts an exemplary recommendation process 1300 suitable for implementation by a patient management system in connection with one or more of the presentation processes 300, 400 described above to provide recommended therapeutic remedial actions for resolving, correcting, or otherwise mitigating an event pattern presented on a GUI display, such as snapshot GUI display 100 of FIG. 1. The various tasks performed in connection with the recommendation process 1300 may be performed by hardware, firmware, software executed by processing circuitry, or any combination thereof. For illustrative purposes, the following description refers to elements mentioned above in connection with FIG. 2. In practice, portions of the recommendation process 1300 may be performed by different elements of the patient management system 200, such as, for example, the infusion device 202, the sensing arrangement 204, the server 206, the database 208, the client device 210, the client application 212, and/or the processing system 216. It should be appreciated that the recommendation process 1300 may include any number of additional or alternative tasks, the tasks need not be performed in the illustrated order and/or the tasks may be performed concurrently, and/or the recommendation process 1300 may be incorporated into a more comprehensive procedure or process having additional functionality not described in detail herein. Moreover, one or more of the tasks shown and described in the context of FIG. 13 could be omitted from a practical embodiment of the recommendation process 1300 as long as the intended overall functionality remains intact.

The recommendation process 1300 initializes or begins by identifying or otherwise determining the event pattern to be analyzed for recommending therapeutic remedial actions (task 1302). In one or more exemplary embodiments, only the highest priority event pattern from among the prioritized event patterns is identified for analysis. In this regard, remedial actions that may be taken by a patient or user to mitigate or otherwise address the highest priority event pattern could also influence or resolve the lower priority event patterns, and hence, providing multiple different recommended therapeutic remedial actions for multiple different event patterns could be unnecessary and confusing. However, in alternative embodiments, each of the prioritized event patterns displayed on a GUI display (e.g., each of the remaining event patterns in the filtered prioritized list at 318) may be identified and analyzed by the recommendation process 1300 to provide multiple different options for therapy modifications that could be undertaken. In yet other embodiments, the recommendation process 1300 may be triggered or initiated by user selection of a particular event pattern for analysis (e.g., from within the event pattern analysis region or another GUI display), whereby the event pattern whose selection triggered the recommendation process 1300 is identified as the event pattern for analysis.

In the illustrated embodiment, the recommendation process 1300 continues by identifying, obtaining or otherwise determining physiological information associated with the patient (task 1304). In this regard, the server 206 obtains or calculates physiological information associated with the patient, such as, for example, the estimated A1C (or alternatively, glycohemoglobin or glycated hemoglobin) level calculated based on the sensor glucose measurement values over the snapshot time period, the average sensor glucose measurement values over the snapshot time period, the average reference blood glucose measurement values (e.g., from a blood glucose meter) over the snapshot time period, and the like. Depending on the embodiment, the server 206 may obtain the patient physiological information from the database 208 and/or infusion device 202, or the server 206 may obtain historical sensor measurements from the database 208 and/or infusion device 202 and utilize the obtained historical measurements to calculate the physiological information associated with the patient for the snapshot time period.

The recommendation process 1300 also identifies, obtains or otherwise determines current therapeutic information for the patient (task 1306). In this regard, the recommendation process 1300 identified or determines the current medications, dosages, types of therapy, and other therapeutic settings or configurations associated with the patient. For example, the database 208 may maintain a patient profile or similar record or entry that maintains an association between one or more patient identifiers and the current therapy assigned or associated with the patient, including, the current medications prescribed to the patient, the type or manner of administration (e.g., basal infusion, boluses or manual injections, oral administration, or the like), the number and/or amount of dosages prescribed to the patient, and potentially other information characterizing the current therapy associated with the patient. The patient profile in the database 208 may also include other clinical or physiological data associated with the patient that may influence suggested or recommended therapy modifications, such as, for example, the patient's height, weight, cholesterol levels, blood pressure, activity metrics or data, sleep quality data, and the like. In other embodiments, the current therapy information may be stored or maintained at one of the infusion device 202 and the client device 210 and retrieved by the server 206 via the network 214.

The recommendation process 1300 continues by identifying or otherwise obtaining therapeutic modification logic associated with the identified event pattern and corresponding to the physiological condition of the patient and current patient therapy (task 1308). In exemplary embodiments, the database 208 maintains one or more tables or lists of logic rules for determining therapy adjustments or modifications in association with a particular combination of event pattern, medications involved in the patient's therapy, and the patient's physiological condition. Thus, different types of adjustments or modifications may be indicated for a particular event pattern, depending on the particular physiological condition of the patient. For example, an event pattern could potentially be resolved by increasing or decreasing a dosage of a particular medication rather than adding or removing a medication to the patient's therapy, depending on the estimated A1C level and/or the mean sensor glucose level for the patient. As another example, adjustments or modifications may be indicated (or not indicated) for a particular event pattern based on the patient's specific glycemic goals or other objectives that may be established by the patient's healthcare provider, or whether or not such goals or objectives have already been achieved. In exemplary embodiments, after identifying the event pattern to be analyzed for a particular patient and the relevant physiological information and combination of medications for the patient, the server 206 accesses the database 208 (or alternatively another device 202, 210 via the network 214) to retrieve the corresponding therapy modification logic rules associated with the identified event pattern and corresponding to the combination of the detected event pattern, combination of medications, and the patient's physiological condition.

Still referring to FIG. 13, the recommendation process 1300 continues by determining one or more therapeutic modifications for mitigating, resolving, or otherwise addressing the event pattern by applying the obtained therapy modification logic rules using the patient's current therapy configuration and physiological condition (task 1310). In exemplary embodiments, the server 206 applies the obtained therapy modification logic rules associated with the event pattern to the current dosages associated with the patient's current therapy to determine recommended therapy modifications for mitigating, resolving, or otherwise addressing the event pattern. For example, if the current dosage of a particular medication or combination of medications is less than a threshold dosage (e.g., one half of the maximum dosage), then the therapy modification logic rules may identify or otherwise indicate an amount by which a particular medication should be increased. Conversely, when the current dosage of the particular medication or combination of medications is greater than the threshold dosage, then the therapy modification logic rules may identify or otherwise indicate another medication that should be added to the patient's therapy. For dual therapy or other therapy configurations with multiple medications, the therapy modification logic rules may identify or otherwise indicate which of the medications should have its dosage adjusted when the combined dosage is less than a threshold for the combined medications.

In some embodiments, the therapy modification logic rules utilized by the recommendation process 1300 may also consider patient physiological information, such as, for example, sensor glucose measurement values or one or more performance metrics calculated based on the historical measurement data for the patient. In this regard, a recommended therapy modification could be influenced by one or more of the estimated A1C level calculated based on sensor glucose measurement values over the snapshot time period or the estimated percentage(s) of the snapshot time period during which the patient's sensor glucose measurement values were above an upper glucose threshold value (e.g., 150 mg/dL), below a lower glucose threshold value (e.g., 70 mg/dL), or between the upper and lower glucose threshold values corresponding to a target sensor glucose range. Thus, the recommended therapy modification chosen or selected by the recommendation process 1300 may be one that is likely to resolve, mitigate, or otherwise address the identified event pattern, while secondarily being most likely to improve one or more performance metrics or other aspects of regulating the patient's physiological condition.

In various embodiments, the recommendation process 1300 may also account for other patient-specific variables which may be stored or otherwise maintained in association with the patient's profile or electronic medical record in the database 208. For example, the patient's A1C goal, previous therapies, allergies and drug intolerances, information characterizing the patient's renal function, information characterizing the patient's hepatic function, and the like may be stored in the database 208 and factored in or otherwise accounted for by the therapy modification logic rules. Thus, the recommended therapeutic remedial actions identified by the recommendation process 1300 may be the most appropriate actions for addressing the identified event pattern, accounting for the patient's physiological condition or glycemic issues, goals or objectives, allergies and drug intolerances, and potentially other clinical variables.

Table 1 represents an exemplary set of therapy modification logic rules that may be maintained in a database 208. It should be noted that Table 1 merely depicts one particular example of therapy modification logic rules for dual combination therapies with a particular A1C level for a particular event pattern, and in practice, the database 208 may maintain any number of different tables to variously accommodate any number of potential event patterns that may be detected, in combination with any number of potential therapy configurations and dosages (including treatment naïve or naïve therapy, monotherapy, and the like), in association with different A1C levels, glucose levels, or other glycemic statuses. In some embodiments, the therapy modification logic rule tables may be stablished or promulgated by a regulatory agency, however, in alternative embodiments, the therapy modification logic rules may be configurable or otherwise specific to a particular doctor, hospital, or other care provider. Accordingly, the subject matter described herein is not limited to the example therapy modification logic rules of Table 1.

Table 1 depicts therapy modification logic rules associated with a hyperglycemic event pattern associated with a post-meal monitoring period for estimated A1C levels below a threshold value of 9%. The logic rules depend on the particular dual combination therapy that the patient it utilizing (e.g., any two of Metformin (Met), a dipeptidyl peptidase 4 (DPP-4) inhibitor, a glucagon-like peptide-1 (GLP-1) receptor agonist, Sulfonylurea or glinide (SU/glinide), Thiazolidenedione (TZD), a sodium-glucose cotransporter 2 (SGLT-2) inhibitor, or basal insulin), and whether or not the current dosage information is less than one half of the maximum dosage associated with the particular dual combination therapy. For example, for a patient with a current therapy configuration of Metformin and a DPP-4 inhibitor (Met+DPP-4) with a current dosage less than one half the maximum dosage of the dual combination, a therapeutic modification of increasing the dosage of the DPP-4 inhibitor may be identified and recommended or otherwise indicated on a snapshot GUI display for the patient. Alternatively, for a patient with a current therapy configuration of Metformin and Thiazolidenedione (Met+TZD) with a current dosage less than one half the maximum dosage of the dual combination, therapeutic modifications of adding one of a DPP-4 inhibitor, a GLP-1 receptor agonist, a SGLT-2 inhibitor, an alpha-glucosidase inhibitor (AGI), or pre-meal rapid-acting insulin may be identified and recommended or otherwise indicated on a snapshot GUI display for the patient, thereby allowing the patient, doctor, nurse, or other clinician to readily identify the need to increase medications and which options are likely to be best for the patient given the patient's current therapy configuration.

TABLE 1

| Dual Combination Therapy Configuration | If . . . <½ Max dose of Dual Combination | If ≥½ Max dose of Dual Combination, Then Add one of the following: |
|---|---|---|
| Met + DPP-4 | Increase dose of DPP-4 if appropriate; Also, Add one of the drugs on right: | SGLT-2<br>AGI<br>Pre-meal rapid-acting insulin |
| Met + GLP-1 | Increase dose of GLP-1 if appropriate; Also, Add one of the drugs on right: | SGLT-2<br>AGI<br>Pre-meal rapid-acting insulin |
| Met + SU/glinide | Increase dose of SU/glinide if appropriate; Also, Add one of the drugs on right: | DPP-4<br>GLP-1<br>SGLT-2<br>AGI<br>Pre-meal rapid-acting insulin |
| Met + TZD | Add one of the drugs on right: | DPP-4<br>GLP-1<br>SGLT-2<br>AGI<br>Pre-meal rapid-acting insulin |
| Met + SGLT-2 | Increase dose of SGLT-2 if appropriate; Also, Add one of the drugs on right: | DPP-4<br>GLP-1<br>AGI<br>Pre-meal rapid-acting insulin |
| Met + Basal insulin | Add one of the drugs on right: | DPP-4<br>GLP-1<br>SGLT-2<br>AGI<br>Pre-meal rapid-acting insulin |
| SU/glinide + DPP-4 | Increase dose of SU/glinide and/or DPP-4 if appropriate; Also, Add one of the drugs on right: | Met + SGLT-2<br>Met + AGI<br>Met + Pre-meal rapid-acting insulin |
| SU/glinide + GLP-1 | Increase dose of SU/glinide and/or GLP-1 if appropriate; Also, Add one of the drugs on right: | Met + SGLT-2<br>Met + AGI<br>Met + Pre-meal rapid-acting insulin |
| SU/glinide + TZD | Increase dose of SU/glinide if appropriate; Also, Add one of the drugs on right: | Met + DPP-4<br>Met + GLP-1<br>Met + SGLT-2<br>Met + AGI<br>Met + Pre-meal rapid-acting insulin |
| SU/glinide + SGLT-2 | Increase dose of SU/glinide and/or SGLT-2 if appropriate; Also, Add one of the drugs on right: | Met + DPP-4<br>Met + GLP-1<br>Met + AGI<br>Met + Pre-meal rapid-acting insulin |
| SU/glinide + Basal insulin | Increase dose of SU/glinide, if appropriate; Also, Add one of the drugs on right: | Met + DPP-4<br>Met + GLP-1<br>Met + SGLT-2<br>Met + AGI<br>Met + Pre-meal rapid-acting insulin |
| TZD + DPP-4 | Increase dose of TZD and/or DPP-4, if appropriate Also, Add one of the drugs on right: | Met + SGLT-2<br>Met + AGI<br>Met + Pre-meal rapid-acting insulin |
| TZD + GLP-1 | Increase dose of TZD and/or GLP-1, if appropriate; Also, Add one of the drugs on right: | Met + SGLT-2<br>Met + AGI<br>Met + SU/glinide<br>Met + Pre-meal rapid-acting insulin |
| TZD + SGLT-2 | Increase dose of TZD and/or SGLT-2, if appropriate; Also, Add one of the drugs on right: | Met + DPP-4<br>Met + GLP-1<br>Met + AGI<br>Met + SU/glinide<br>Met + Pre-meal rapid-acting insulin |
| TZD + Basal insulin | Increase dose of TZD, if appropriate; Also, Add one of the drugs on right: | Met + DPP-4<br>Met + GLP-1<br>Met + SGLT-2<br>Met + AGI<br>Met + SU/glinide<br>Met + Pre-meal rapid-acting insulin |
| DPP-4 + SGLT-2 | Increase dose of DPP-4 and/or SGLT-2, if appropriate; Also, Add one of the drugs on right: | Met + AGI<br>Met + SU/glinide<br>Met + Pre-meal rapid-acting insulin |

TABLE 1-continued

| Dual Combination Therapy Configuration | If . . . <½ Max dose of Dual Combination | If ≥½ Max dose of Dual Combination, Then Add one of the following: |
|---|---|---|
| GLP-1 + SGLT-2 | Increase dose of GLP-1 and/or SGLT-2, if appropriate; Also, Add one of the drugs on right: | Met + AGI<br>Met + SU/glinide<br>Met + Pre-meal rapid-acting insulin |
| Basal insulin + SGLT-2 | Increase dose of SGLT-2 if appropriate; Also, Add one of the drugs on right: | Met + DPP-4<br>Met + GLP-1<br>Met + AGI<br>Met + SU/glinide<br>Met + Pre-meal rapid-acting insulin |

Still referring to FIG. 13, after determining the recommended modifications to the patient's current therapy configuration, the recommendation process 1300 generates or otherwise provides graphical indicia of the recommended therapy changes in graphical association with the identified event pattern (task 1312). In one or more embodiments, the server 206 generates recommended therapy modifications when populating the event pattern analysis region associated with the identified event, for example, by displaying recommended therapy modifications for the highest priority event pattern in its associated event pattern analysis region of the pattern guidance display. In another embodiment, the server 206 generates or otherwise provides the recommended therapy modifications in response to selection of a particular event pattern for analysis (e.g., from within the event pattern analysis region). In various embodiments, the graphical indicia of a recommended therapy modification may be realized as a graphical representation or depiction of text stored in the database 208 (e.g., in association with the therapy modification logic rules, in association the therapy configuration for which the recommended therapy modification is an option, or the like).

Figure 14:
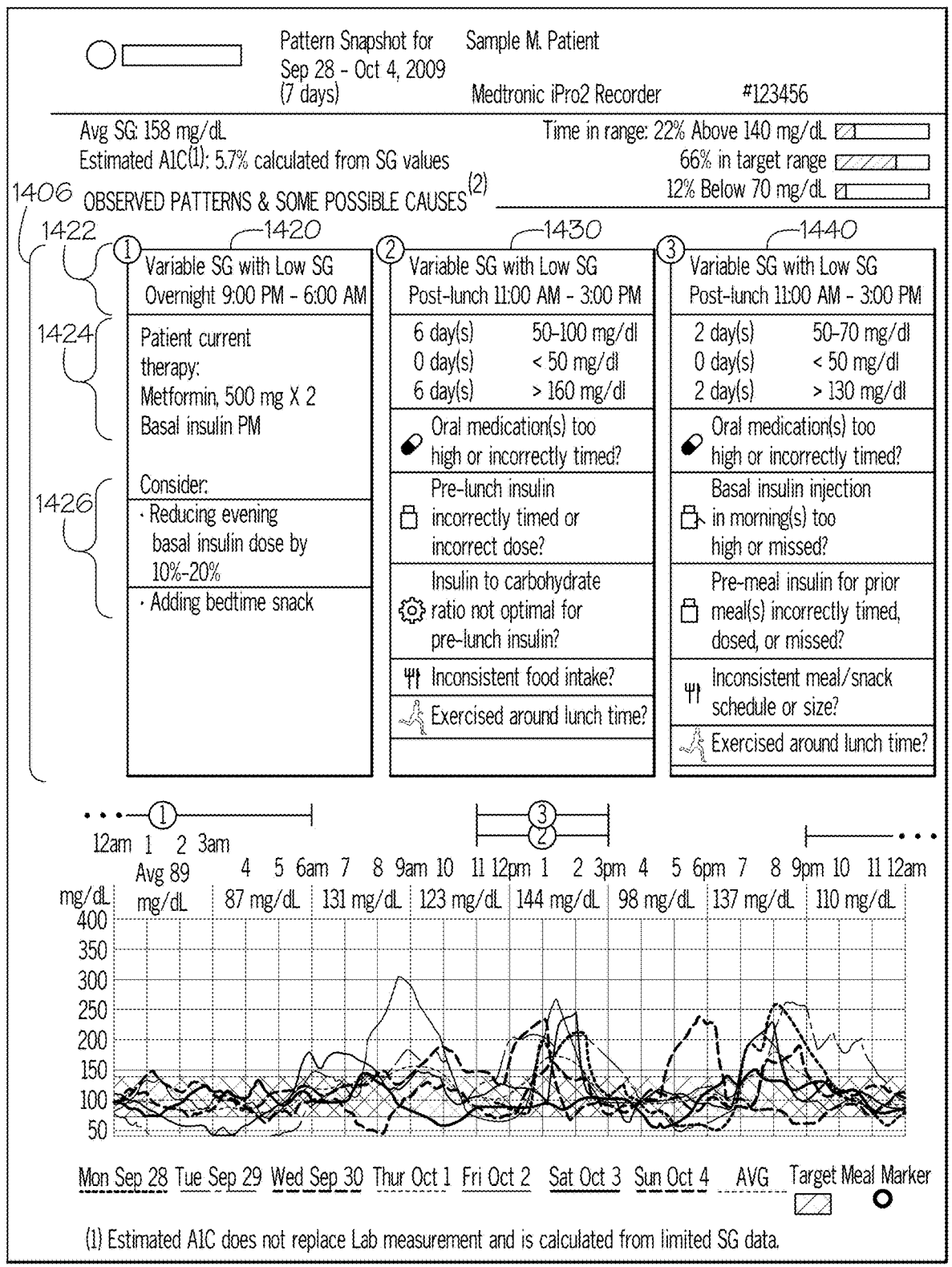

FIG. 14 depicts an exemplary embodiment of a snapshot GUI display 1400 (or report) that may be presented on a display device associated with an electronic device, such as the client device 210, in connection with the recommendation process 1300 of FIG. 13. Similar to the snapshot GUI display 100 of FIG. 1, the snapshot GUI display 1400 includes a pattern detection region 1406 including a plurality of pattern guidance displays 1420, 1430, 1440 corresponding to patterns of events identified during the snapshot time period based on the patient's sensor glucose measurement values for the snapshot time period. In the illustrated embodiment of FIG. 14, the highest prioritized detected event pattern, a variability event associated with the overnight time period, is identified by the recommendation process 1300 for recommending therapy modifications capable of addressing the overnight variability event given the patient's current therapy.

As described above in the context of FIG. 13, the server 206 accesses the database 208 using the patient's identification information to identify the current therapy configuration for the patient (500 milligrams of metformin twice daily and basal insulin in the evening) and obtain the therapy modification logic rules associated with the dual combination therapy of metformin and basal insulin. In exemplary embodiments, the obtained therapy modification logic rules also correspond to the patient's estimated A1C level for the snapshot time period. For example, there may be one set of variability event therapy modification logic rules for the metformin and basal insulin dual therapy combination associated with A1C levels below a threshold value of 9% and another set of variability event therapy modification logic rules for the metformin and basal insulin dual therapy combination associated with A1C levels above the threshold value of 9%, with the server 206 selecting the therapy modification logic rules associated with A1C levels below the threshold value based on the patient's estimated A1C level for the snapshot time period of 5.7%.

Based on the obtained therapy modification rules and the patient's current dosages, the server 206 identifies a recommended therapy modification of reducing the basal insulin dosage to address the overnight variability event. In this regard, the server 206 may identify a modification to the dosage or delivery rate of insulin to be delivered by the infusion device 202 during future instances of the monitoring period associated with the highest prioritized detected event pattern (e.g., the basal dosage during the overnight time period). Thereafter, one or more autonomous operating modes supported by the infusion device 202 may be modified, adjusted, or otherwise reconfigured to autonomously regulate the condition of the patient in accordance with the recommended dosage modification in response to a user input. For example, the patient or other user (e.g., the patient's doctor or another clinician) could then interact with the infusion device 202 (e.g., by manipulating user interface 1040) to reprogram or reconfigure one or more parameters, limits, targets, set points, or other settings associated with the control scheme or algorithm implemented by the infusion device 202 to achieve the modified dosage when autonomously regulating the patient's glucose level during the time of day corresponding to the monitoring period associated with the detected event pattern (e.g., during overnight closed-loop operation). To reduce the evening basal insulin dosage by 10% to 20% as indicated in analysis region 1426, the overnight basal infusion rate setting of the infusion device 202 may be reduced by the corresponding percentage, or the amount of insulin injected at bedtime may be reduced by the corresponding percentage.

In some embodiments, the graphical representation of a modification to the dosage or delivery rate of insulin to be delivered by the infusion device 202 during future instances of the monitoring period may be selectable or associated with a button or similar selectable GUI element that facilitates the client device 210 or the server 206 automatically reprogramming the infusion device 202 (e.g., by transmitting corresponding commands, code or other programming instructions to the infusion device 202 via the network 214) for implementing the modified dosage during the relevant time period. Additionally, in the illustrated embodiment, the server 206 utilizes the obtained therapy modification rules to identify another recommended therapeutic remedial action of adding a bedtime snack to increase the patient's glucose level. In this regard, in some embodiments, a recommended therapeutic remedial action may be identified based on the patient exhibiting sensor glucose measurement values above or below a threshold (e.g., below the lower glucose threshold value for the overnight monitoring time period associated with the highest priority variability event) and/or a duration of time during which those measurements are exhibited within the monitoring period.

In a similar manner as described above in the context of FIGS. 1-4, the server 206 generates a header region 1422 with graphical indicia of the overnight variability event. In connection with the recommendation process 1300, the server 206 generates a current therapy summary region 1424 that includes graphical indicia of the patient's current therapy configuration along with an analysis region 1426 that includes graphical indicia of the recommended remedial actions identified based on therapy modification rules associated with the patient's current therapy configuration. In some embodiments, the therapy summary and analysis regions 1424, 1426 are presented in response to user selection of the overnight variability event pattern guidance display 1420 or the header region 1422 in lieu of other summary and analysis regions (e.g., regions 124, 126). In this regard, the recommendation process 1300 may be triggered or initiated to generate and populate the therapy summary and analysis regions 1424, 1426 presented in response to user selection of the overnight variability event pattern guidance display 1420 or the header region 1422. In other embodiments, therapy summary and analysis regions 1424, 1426 may automatically be presented for the highest priority event pattern in lieu of other summary and analysis regions (e.g., regions 124, 126) upon initial generation of the snapshot GUI display 1400.

Although not illustrated in FIG. 14, in various alternative embodiments, the recommendation process 1300 may be automatically performed with respect to the other displayed event patterns to populate the remaining pattern guidance displays 1430, 1440 in addition to pattern guidance display 1420. Alternatively, the recommendation process 1300 may be performed with respect to one of the other displayed event patterns in response to selection of the respective pattern guidance display 1430, 1440. However, as noted above, remedial actions that may be taken to mitigate or otherwise address lower priority event pattern could be redundant, unnecessary, and/or confusing in view of recommended remedial actions for the highest priority event pattern.

Figure 15:
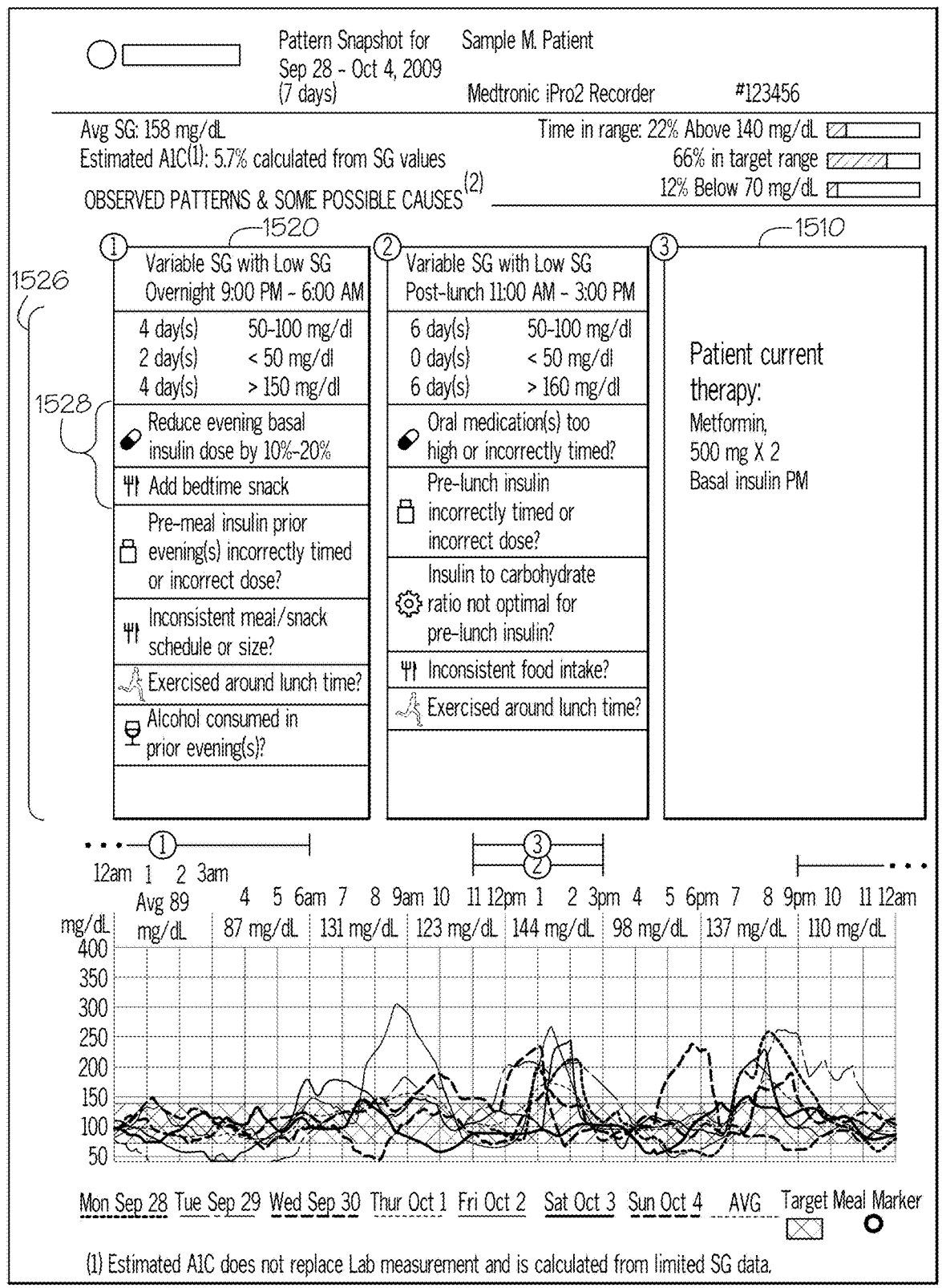

FIG. 15 depicts another exemplary embodiment of a snapshot GUI display 1500 that may be presented on or by an electronic device in connection with the recommendation process 1300 of FIG. 13. The snapshot GUI display 1500 includes a patient therapy region 1510 that includes graphical indicia of the patient's current therapy configuration, which could be rendered outside of or alongside of the pattern detection region. In the embodiment of FIG. 15, the event pattern analysis region 1526 of the highest priority pattern guidance display 1520 includes graphical indicia of the recommended therapeutic remedial actions 1528 identified by the recommendation process 1300 while the current patient therapy configuration is concurrently presented within the patient therapy region 1510. In one or more embodiments, the recommended therapeutic remedial actions 1528 are prioritized or ordered first among the information presented within the event pattern analysis region 1526, for example, by displaying the recommended therapeutic remedial actions 1528 above the potential causes or other information related to the overnight variability event pattern.

FIG. 16 depicts another exemplary embodiment of a snapshot GUI display 1600 that may be presented on or by an electronic device in connection with the recommendation process 1300 of FIG. 13. The snapshot GUI display 1600 includes a patient therapy region 1610 that includes graphical indicia of the patient's current therapy configuration which is displayed proximate the pattern detection region 1606. In the embodiment of FIG. 16, the pattern detection region 1606 includes a menu or list of pattern guidance displays 1620, 1630, 1640 ranked or ordered according to prioritization, with graphical indicia of the recommended therapeutic remedial actions 1628 being presented below the highest priority event pattern guidance display 1620 in graphical association with or proximity to the highest priority event pattern. In this regard, in some embodiments, the pattern guidance displays 1620, 1630, 1640 may be expandable or collapsible to display recommended therapeutic remedial actions in response to user selection of respective ones of the pattern guidance displays 1620, 1630, 1640. In such embodiments, the recommendation process 1300 may be initiated or otherwise performed with respect to a selected event pattern to determine recommended therapeutic remedial actions for populating the expanded pattern guidance display region upon or in response to user selection of the respective event pattern.

The snapshot GUI display 1600 also includes a supplemental information region 1650 that may include disclaimer language or other explanatory information or guidance pertaining to the recommended therapeutic remedial actions 1628, such as, for example, potential side effects associated with proposed medications to be added to the patient's therapy regimen, or the like. The supplemental information region 1650 may be displayed adjacent to or otherwise in graphical association with the pattern detection region 1606 or the selected pattern guidance display 1620. Information presented in the supplemental information region 1650 may be stored or maintained in the database 208 and retrieved by the server 206 for presentation. In other embodiments, rules or formula for generating the supplemental information may be stored or maintained in the database 208 and retrieved by the server 206 for dynamically determining the supplemental information to be presented in the region 1650 based on the patient's current therapy configuration, physiological condition, or other patient-specific variables or factors.

It should be noted that FIGS. 14-16 depict merely some exemplary GUI displays for presenting recommended therapeutic remedial actions, and the subject matter described herein is not necessarily limited to any particular manner of presentation. By virtue of the recommendation process 1300 of FIG. 13, detected event patterns exhibited by a particular patient and that patient's particular therapy configuration, physiological condition, and potentially other patient-specific variables may be synthesized and analyzed to determine comprehensive therapeutic recommendations for remedying, resolving, mitigating, or otherwise addressing a particular event pattern in a manner that accounts for the patient's current therapy and physiological condition. The recommended therapeutic remedial actions may also account for various patient-specific variables to provide recommendations that reflect a relatively comprehensive review of the patient's medical records, history and prior therapies. The recommended therapeutic remedial actions are then presented in connection with other graphical indicia pertaining to detected event pattern, thereby clearly conveying to the patient or other user the nature of the event pattern and potential ways to address the event pattern, which, in turn, leads to better patient outcomes.

It should be noted that although the subject matter may be described herein primarily in the context of a patient with Type 2 diabetes taking any one of a wide variety of medications (orals, non-insulin injectables, and insulin) in connection with an infusion device or continuous glucose monitoring, the subject matter described herein is not necessarily limited to use with infusion devices, continuous glucose monitoring, Type 2 diabetes, or the medications described herein. Moreover, in exemplary embodiments, the recommendation processes described herein support modularity or adaptability to accommodate potential new classes of medications and/or new indications for existing classes of medications. For example, the therapeutic modification logic rules may have a modular design that allows for a new module of logic rules pertaining to a new class of medication to be inserted or otherwise configured among logic rules pertaining to existing classes of medications, thereby allowing the therapeutic modification logic rules to be readily updated to accommodate new classes of medication. Similarly, indications for existing classes of medications may be modular, allowing for changes with respect to the indications for those classes or medications that do not impact other classes or medications or the overall hierarchy or flow associated with the therapeutic modification logic rules. Such modularity of the therapeutic modification logic rules facilitates inclusion and prioritization of new classes of medication and/or new indications for existing classes without substantial redesign of the recommendation algorithms or hardware.

Streamlined Snapshot Displays Including Detected Event Patterns with Therapeutic Recommendations Referring now to FIGS. 17-20, in one or more exemplary embodiments, a streamlined snapshot GUI display is provided to convey patient information pertaining to past operation of a fluid infusion device or other monitoring device (e.g., a continuous glucose monitor) with improved clarity, discriminability and consistency, and thereby improving comprehensibility of the snapshot GUI display. In this regard, regions with relatively higher visual consistency and/or relatively less content variability on a patient-to-patient basis, such as the header and graph overlay regions, are visually prioritized over regions where the displayed information is more likely to vary from patient-to-patient, such as the pattern detection region, the patient therapy region, and/or other supplemental information regions. This improves detectability of important information within the visually prioritized regions, such as, for example, the patient's current therapy regimen or the patient's historical measurement data for the patient's glucose level over the snapshot time period that provides the foundation or underlying basis for information presented in the other regions of the display. Additionally, detected event patterns are presented in a top-down manner according to prioritization, thereby improving the detectability and discriminability of the higher priority event pattern(s). The detected event pattern regions are also capable of dynamically increasing or decreasing the amount of displayed information associated with a respective event pattern, thereby improving conciseness of the overall display, while also potentially allowing for improved legibility by increasing available display area for other information.

Figure 17:
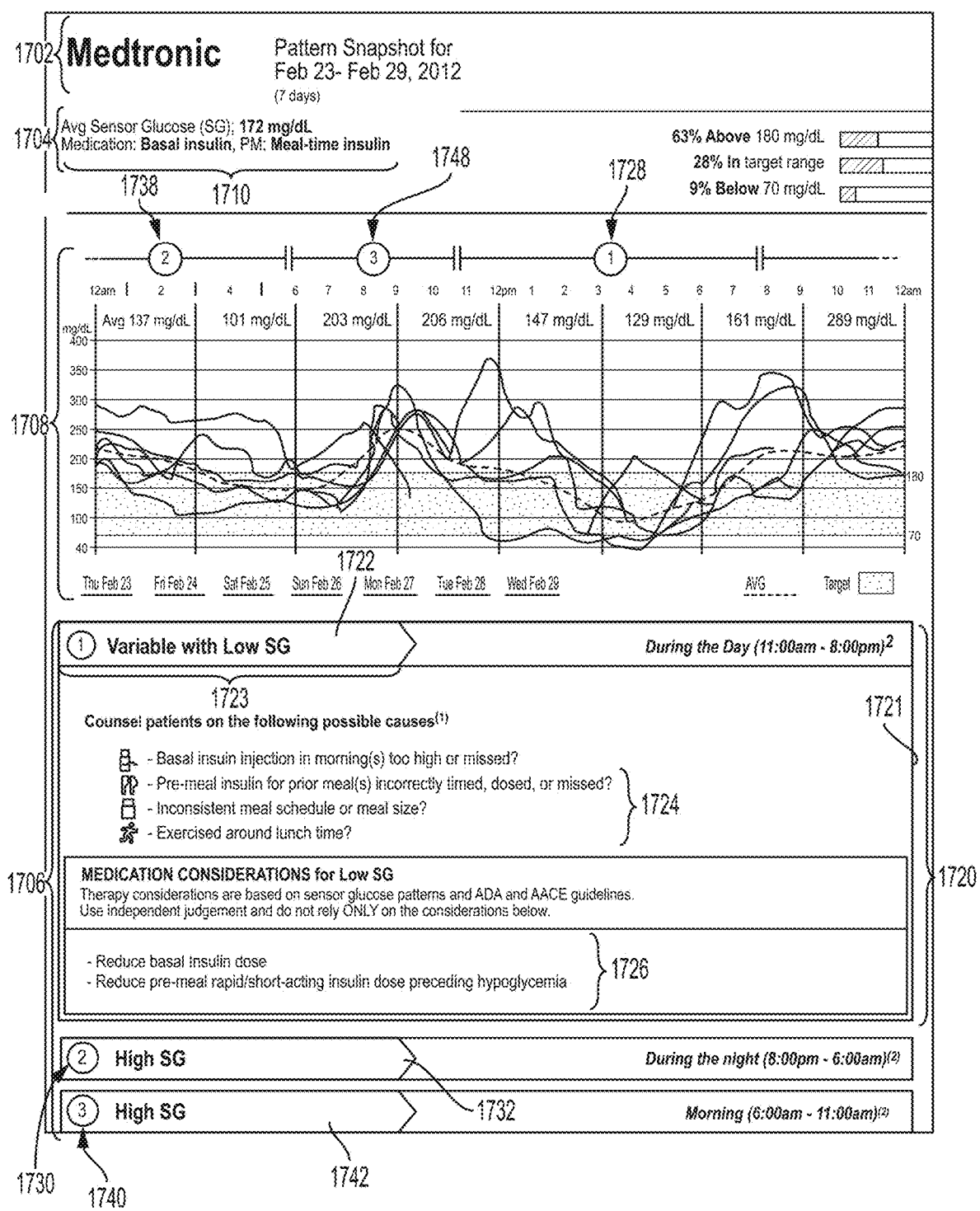
FIGS. 17-20 depict exemplary embodiments of snapshot GUI displays including expandable and collapsible pattern guidance displays suitable for presentation on a display device associated with a computing device in accordance with one or more embodiments.

Referring to FIG. 17, similar to the snapshot GUI display 100 described above in the context of FIGS. 1-4, the streamlined snapshot GUI display 1700 includes a patient information header region 1702 presented at the top of the snapshot GUI display 1700 above a performance metric region 1704. In the streamlined snapshot GUI display 1700, a graph overlay region 1708 closer to the top of the snapshot GUI display 1700 above an event pattern detection region 1706.

In the illustrated embodiment, similar to the performance metric region 104 in FIG. 1, the performance metric region 1704 includes graphical representations or other indicia of the values for various performance metrics summarizing the patient's condition over the snapshot time period that are calculated based on the historical measurement data for the patient's glucose level over the time period associated with the snapshot GUI display 1700. Additionally, the performance metric region 1704 includes graphical representations 1710 (or other graphical indicia) of the patient's current therapy regimen. In this regard, the displayed therapy regimen information 1710 includes a listing of the medications or other medicaments the patient is currently taking. In the illustrated embodiment, the current patient therapy information 1710 indicates the patient administers basal insulin injections in the evening and also administers meal-time insulin.

Figure 18:
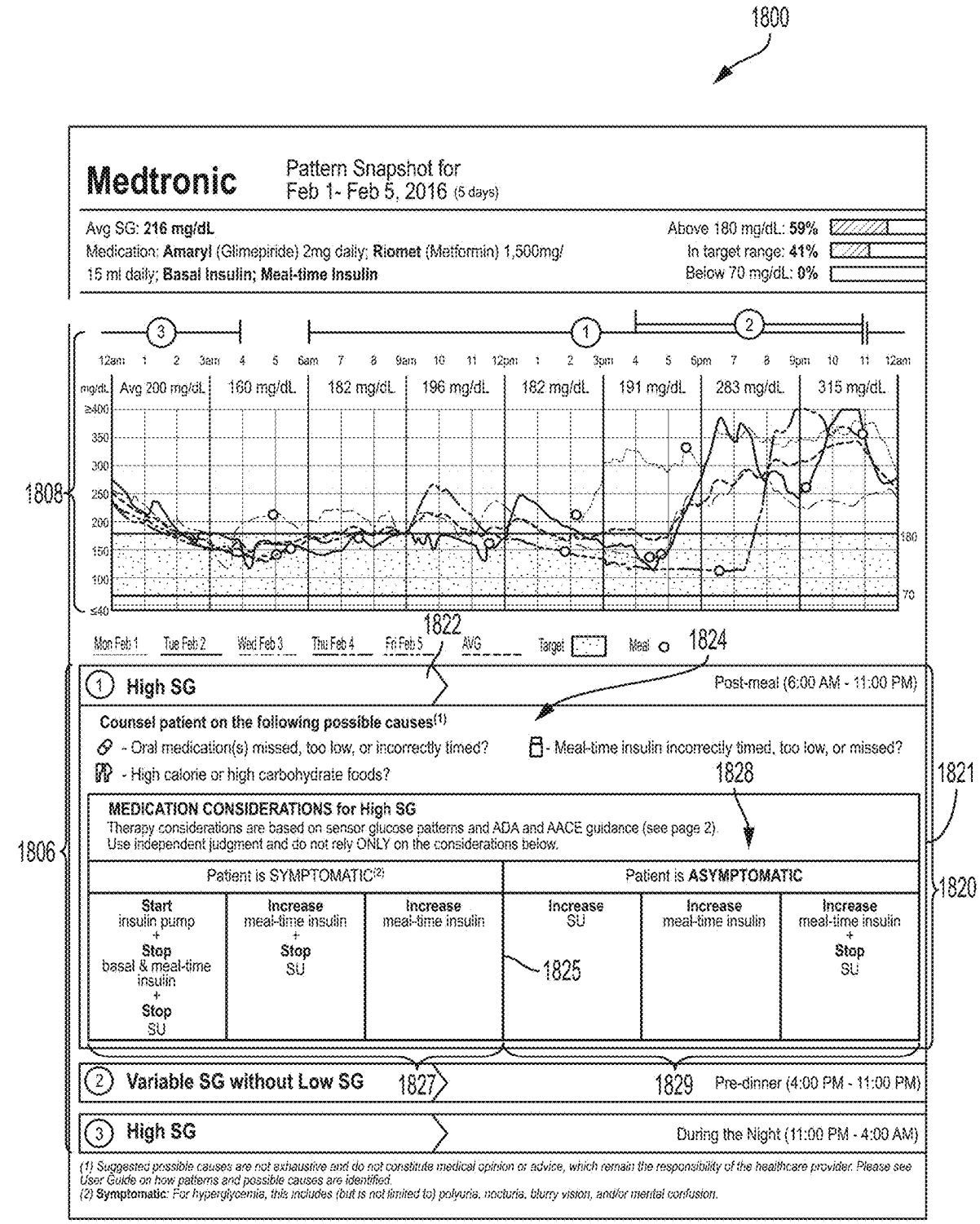
Figure 19:
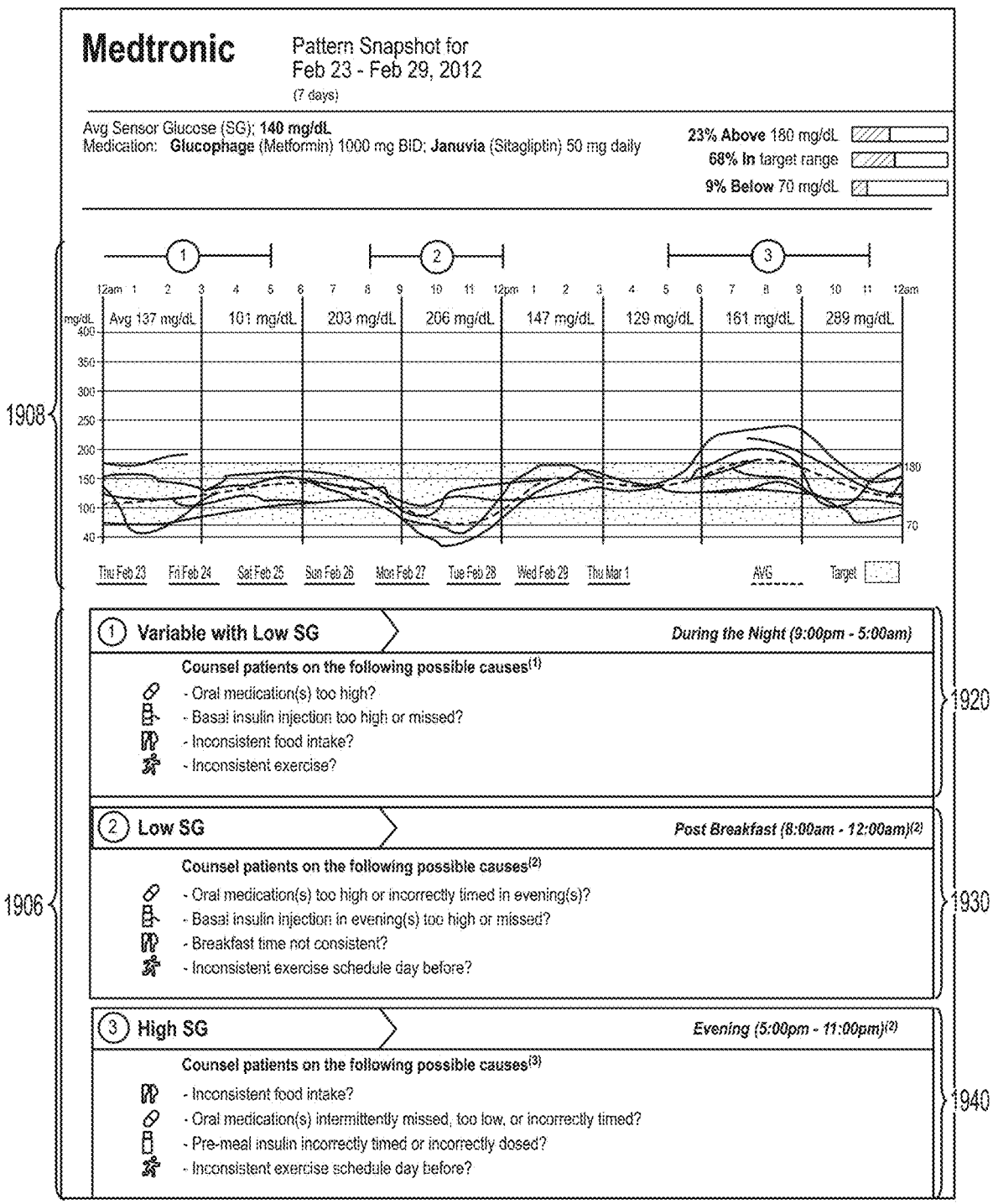

As depicted in FIGS. 18-19, for other types of medications or medicaments, for each medication or medicament, the displayed therapy regimen information includes the frequency at which the respective medication or medicament is administered or taken by the patient (e.g., daily, twice a day (BID), three times a day (TID), four times a day (QID), etc.) along with a dosage associated with each instance, and for a medication or medicament taken at an uncommon time, an indication of the time when taken (e.g., morning (AM), evening (PM), breakfast, lunch, dinner, bedtime, etc.). In exemplary embodiments, the brand name is bolded or otherwise visually emphasized, while the generic name, dosage, frequency, or other temporal indicia are not emphasized. For example, if 850 milligrams of GLUCOPHAGE® is taken twice a day at breakfast and dinner, the corresponding listing in the displayed therapy regimen information may be displayed as "Glucophage (metformin), 850 mg BID." Alternatively, if 850 milligrams of GLUCOPHAGE® is taken twice a day at breakfast and lunch, which is not a commonly expected time for a dose, the corresponding listing in the displayed therapy regimen information may be displayed as "Glucophage (metformin), 850 mg BID, breakfast and lunch."

Still referring to FIG. 17, the graph overlay region 1708 is displayed immediately below and adjacent to the performance metric region 1704 and above the event pattern detection region 1706. This arrangement is consistent with the order in which the patient's doctor or other clinician is likely to be interested in reviewing the patient's history, and thereby improves clarity of the snapshot GUI display 1700 and detectability of the graph overlay region 1708 by directing the viewer's eyes towards the graph overlay region 1708 via preferential placement above the event pattern detection region 1706. This improves the perceived flow of the snapshot GUI display 1700 while also improving comprehensibility of the information subsequently presented in the event pattern detection region 1706 by conveying the relevant underlying historical measurement data for the patient to the viewer first. Additionally, since the general look and feel of the graph overlay region 1708 is independent of the patient's physiological condition (e.g., whether or not the patient has type 1 diabetes or type 2 diabetes), the perceived consistency of the snapshot GUI display 1700 across a patient population is improved.

Similar to the graph overlay region 108 of FIG. 1, the graph overlay region 1708 includes graphical representations of historical measurement data for the patient's glucose level over the snapshot time period with respect to time and a visually distinguishable overlay region that indicates a personalized target range for the patient's sensor glucose measurement values, with the graphical representation of the measurements, meal markers, or other indicia for each different day or date depicted on the graph overlay region 1708 being rendered visually distinct from graphical representations corresponding to other days or dates. The illustrated graph overlay region 1708 also includes graphical representations of multiday averages of the measurement data for different periods or times of day, for example, every three-hour segment of the day. The graph overlay region 1708 also includes graphical indicia 1728, 1738, 1748 of highest priority detected event patterns in a manner that establishes an association between the detected event pattern, the time of day associated with its corresponding monitoring period, and its relative priority level.

The event pattern detection region 1706 is presented below the graph overlay region 1708 and includes a plurality of pattern guidance displays 1720, 1730, 1740 corresponding to the three highest prioritized event patterns identified during the snapshot time period based on the patient's sensor glucose measurement values for the snapshot time period. The pattern guidance displays 1720, 1730, 1740 are expandable or collapsible to dynamically increase or decrease the amount of information presented in association with a respective event pattern. In the embodiment of FIG. 17, the second and third priority event pattern guidance displays 1730, 1740 are collapsed or not expanded, while the highest priority event pattern guidance display 1720 is expanded to display an event pattern analysis region 1724 associated with the event pattern and a therapy analysis region 1726 for the event pattern within a window 1721 associated with the header region 1722 for the highest priority event pattern guidance display 1720. The event pattern analysis region 1724 includes list of potential causes phrased in a manner that suggests remedial actions that can be taken to resolve or correct the variability event, while the therapy analysis region 1726 includes recommended therapeutic remedial actions for resolving or correcting the variability event. The list of potential causes may be personalized or otherwise tailored for the medications or classes of medications corresponding to the patient's current therapy regimen (e.g., a possible cause related to insulin will not be displayed if the patient is not taking insulin). The contents of the analysis regions 1724, 1726 may be identified, determined, or otherwise generated as described above in the context of FIGS. 1-4 and FIGS. 13-16.

The header regions 1722, 1732, 1742 for each of the pattern guidance displays 1720, 1730, 1740 includes a number indicating the priority of the respective event pattern, an identification of the type of event pattern detected, and the time period or timeframe associated with the detected event pattern. In exemplary embodiments, the header regions 1722, 1732, 1742 are selectable or otherwise manipulable to dynamically increase or decrease the displayed information associated with the respective event pattern. In this regard, FIG. 17 depicts an example where the highest priority event header region 1722 has been selected or otherwise activated to expand the window 1721 associated with the highest priority event below the highest priority event header region 1722 to display the analysis regions 1724, 1726 associated with the highest priority event above the lower priority event pattern guidance displays 1730, 1740 (e.g., between the highest priority event header region 1722 and the second highest priority event header region 1732), while the other header regions 1732, 1742 are in their deselected or deactivated states to remove or otherwise hide the analysis regions associated with the lower priority event pattern guidance displays 1730, 1740. In some embodiments, the markers 1728, 1738, 1748 corresponding to the respective pattern guidance displays 1720, 1730, 1740 may also be selectable or otherwise manipulable to dynamically increase or decrease the displayed information associated with the respective event pattern. For example, to expand the highest priority event pattern guidance window 1721, a user may select either the highest priority event header region 1722 or the highest priority event marker 1728 within the graph overlay region 1708. Additionally, in some embodiments, the highest priority event pattern guidance display 1720 may be automatically activated or expanded by default (and the lower priority event pattern guidance displays 1730, 1740 collapsed or condensed by default) upon presentation of the snapshot GUI display 1700 even in the absence of any user selection.

By allowing event pattern information to be selectively and dynamically hidden or added to the display, the perceived clarity and conciseness of the event pattern detection region 1706 is improved, which, in turn may help aid the comprehensibility of the displayed information. Additionally, freeing up display area on the display device by hiding information associated with lower priority event pattern guidance displays 1730, 1740 may allow for the legibility of the displayed information associated with the higher priority event pattern guidance display 1720 to be improved by increasing the size of the text, icons, or other graphical elements that make up the analysis regions 1724, 1726 to fill the available display area.

In exemplary embodiments, the event pattern markers 1728, 1738, 1748 and header regions 1722, 1732, 1742 utilize different colors that differentiate one another and indicate whether a detected event pattern involves a low or high glucose level. For example, the marker 1728 associated with the low glucose variability event may be rendered using red, pink, or a similar hue to indicate a relatively higher potential severity associated with the event, and similarly, at least a portion of the header region 1722 may be rendered using the same color (e.g., the portion 1723 of the header region 1722 encompassing the identification of the event type and priority). Such color-coordination conveys or otherwise implies the importance and severity of the event pattern consistent with society and reduces the amount of time required for a user to identify the most significant event patterns on the graph overlay region 1708. Conversely, markers 1738, 1748 and header regions 1732, 1742 associated with a high glucose level may incorporate yellow or a similar hue to indicate a relatively lower severity.

FIG. 18 depicts another exemplary embodiment of a streamlined snapshot GUI display 1800. In the embodiment of FIG. 18, the expanded window 1821 for the highest priority event pattern guidance display 1820 in the event pattern detection region 1806 below the graph overlay region 1808 includes a tabular representation 1828 of recommended therapeutic remedial actions within the therapy analysis region 1826 for resolving or correcting the low glucose event. In this regard, the table 1828 of recommended therapeutic remedial actions indicates a plurality of different potential therapeutic remedial actions that may be appropriate for the patient's current therapy regimen. The different potential therapeutic remedial actions are differentiated by a visually distinguishable vertical divider 1825 into a first subset 1827 of potential remedial actions for a symptomatic patient and a second subset 1829 of potential remedial actions if the patient is asymptomatic. In the illustrated embodiment, the tabular therapy analysis region 1826 is presented within the expanded window 1821 associated with the highest priority event pattern header region 1822 beneath the event pattern analysis region 1824 and above the header regions and guidance displays for the lower priority event patterns.

As described above in the context of FIG. 13, the potential therapeutic remedial actions presented in the various columns of the table 1828 are determined for the corresponding event pattern based on the patient's current therapy configuration. Each column of the table 1828 is unique relative to other columns in the table 1828, and each column includes one or more potential therapeutic remedial actions, such as, for example, a modified dosage (or cessation) of a current medication or medicament, an additional medication or medicament, and/or a combination thereof. The table 1828 of potential therapeutic modifications allows the patient's doctor or clinician to readily identify a broad set of potential therapy modifications that may be appropriate given the patient's current therapy configuration and physiological condition, from which the patient's doctor or clinician can then utilize his or her professional judgment to determine how to modify the patient's therapy to achieve an optimal outcome.

FIG. 19 depicts another exemplary embodiment of a streamlined snapshot GUI display 1900 where each of the event pattern guidance displays 1920, 1930, 1940 within the event pattern detection region 1906 beneath the graph overlay region 1908 are expanded. In such an embodiment, the amount of information presented within the respective pattern guidance displays 1920, 1930, 1940 may be reduced to maintain legibility, for example, by limiting the number of potential causes presented within the respective pattern analysis regions, limiting the number of recommended therapeutic remedial actions within the respective therapy analysis regions, or a combination thereof. In the illustrated embodiment, the pattern guidance displays 1920, 1930, 1940 only include pattern analysis regions associated with the respective event patterns. In this regard, the respective therapy analysis regions may be hidden or otherwise removed from the display to increase the available display area for expanding multiple pattern guidance displays, while also improving clarity by decluttering the display and eliminating potential confusion that could arise by presenting a number of recommended therapeutic remedial actions attempting to individually resolve different event patterns, which could potentially conflict with one another or exacerbate another aspect of the patient's physiological condition. Thus, in such scenarios where the patient's doctor or clinician is concurrently considering or reviewing multiple different event patterns, the patient's doctor or clinician can use his or her judgment in determining how to modify the patient's therapy to achieve an optimal outcome.

Figure 20:
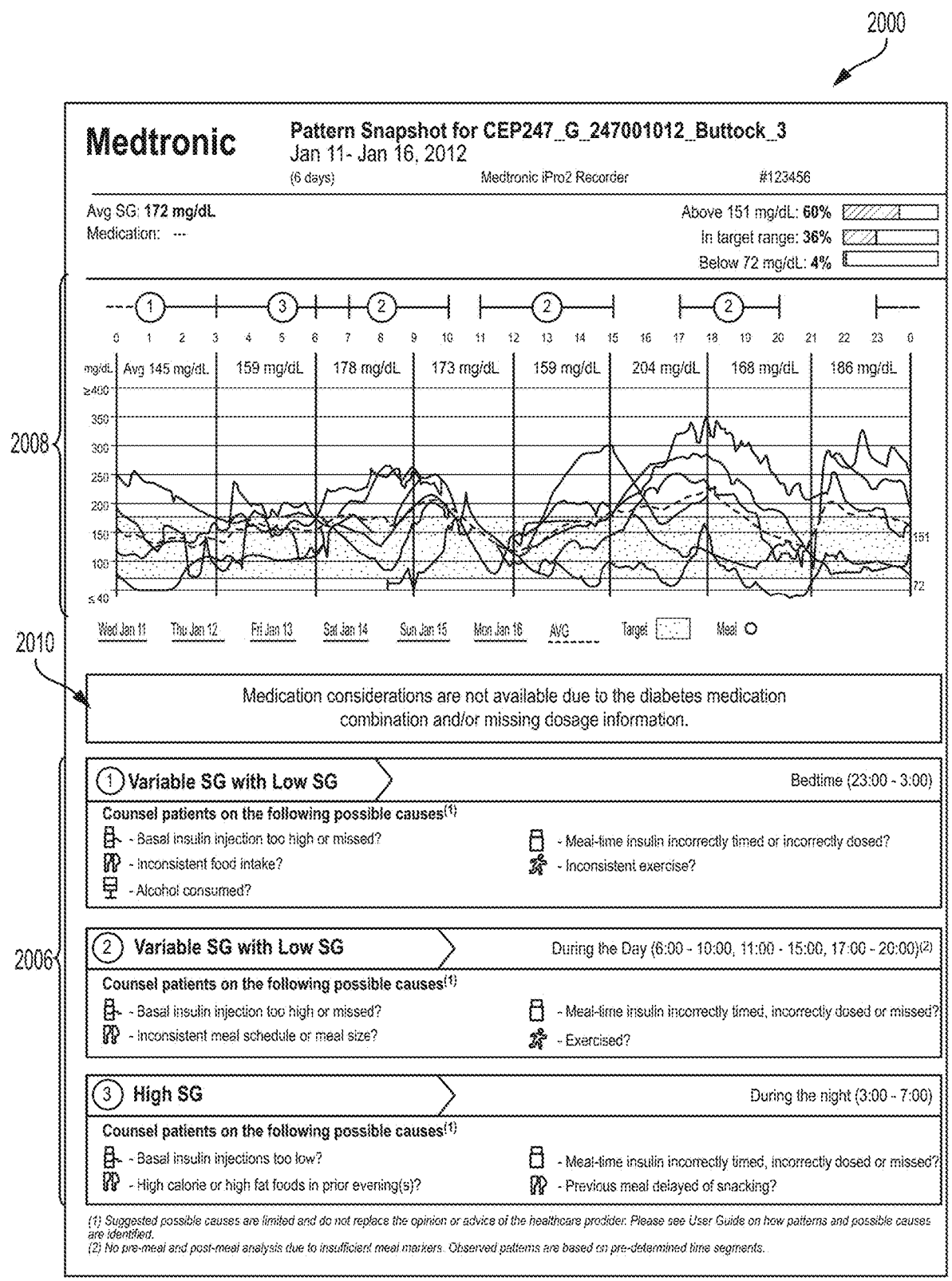

FIG. 20 depicts an embodiment of a streamlined snapshot GUI display 2000 that does not include recommended therapeutic remedial actions due to the absence of information regarding any medications or medicaments prescribed for the patient. In such scenarios, an informational region 2010 is provided vertically between the graph overlay region 2008 and the event pattern detection region 2006 to convey to the viewer or user of the snapshot GUI display 2000 that the following event pattern detection region 2006 does not include therapy analysis regions or recommended therapeutic remedial actions and the underlying rationale for why that information is not presented. The informational region 2010 mitigates potentially perceived inconsistencies in the streamlined snapshot GUI display 2000 across different patients by indicating, explaining, or otherwise conveying a potential inconsistency within the following region 2006 of the display 2000 prior to the eyes of a viewer reading the display 2000 in a top-down fashion reaching the following region 2006. In other words, the informational region 2010 effectively modifies a viewer's expectations regarding the content of the streamlined snapshot GUI display 2000 to align with what is subsequently presented beneath the region 2010, which improves the perceived consistency of the streamlined snapshot GUI display 2000.

In sum, the streamlined snapshot GUI displays provided in FIGS. 17-20 achieve improved conformance with user expectations and direct users towards information in a manner that may be perceived as logical and predictable. Color-coordination between the graph overlay regions and event pattern detection regions and top-down prioritization of event pattern guidance allow users to quickly and accurately distinguish important event patterns, and the amount of displayed event pattern information may be dynamically increased or decreased to improve conciseness and legibility. As a result, the interpretability and comprehensibility of the snapshot GUI display is improved, which, in turn results in increased confidence in the presented information. Thus, the streamlined snapshot GUI displays increase the likelihood of improved patient outcomes resulting from increased reliance on recommended therapeutic remedial actions and/or other guidance or analysis presented on the displays.

Event Pattern Prioritization Using Measurement Uncertainty

In practice, there are numerous sources of potential measurement uncertainty with respect to sensor output, such as, for example, noise, interference, lag, manufacturing variations, deterioration or degradation, or other factors that may influence the accuracy or reliability of the output measurements provided by a sensor. For example, in addition to potential effects of noise or other signal interference, the performance of continuous glucose monitoring (CGM) sensors measuring the glucose in the interstitial fluid (ISF) may vary depending on the location on the body where the sensing element is inserted, the position or orientation of the sensing element responsive to movement by the patient, and/or the duration of time that has elapsed since the sensing element was inserted.

As described in greater detail below, in one or more exemplary embodiments, event pattern detection and prioritization are performed on one or more sets of adjusted measurement data for a snapshot time period, where the measurement data of each of the different sets has been adjusted relative to the observed measurement data for the snapshot time period to account for potential measurement error or uncertainty. For example, the measurement data may be offset or biased up or down by a particular percentage or fixed amount to account for uncertainty or error in the measurement value, and in some instances, the manner or amount of adjustment may also vary with respect to time to reflect probable degradation or aging. Various measurement statistics (e.g., standard deviation, variance, or the like) may also be utilized to calculate or otherwise determine adjusted measurement data based on the observed measurement data.

For each adjusted measurement data set, event patterns during the snapshot time period are detected based on the adjusted measurement data associated therewith, and the detected event patterns are prioritized relative to others associated with that respective data set. Thereafter, the resulting prioritized event patterns for each data set are compared to one another to verify or otherwise confirm the accuracy of the pattern detection based on the degree of matching or mismatching across the different data sets. In this regard, when discrepancies exist between the detected event patterns based on the observed measurement data and one or more adjusted measurement data sets, the displayed event patterns are modified to account for potential uncertainty in the observed measurement data. For example, an event pattern detected based on the observed measurement data may be reprioritized based on the presence or absence of that event pattern in the adjusted measurement data, or an event pattern detected based on an adjusted measurement data set may be substituted for an event pattern detected based on the observed measurement data. Augmenting the displayed event patterns based on adjusted measurement data that accounts for measurement uncertainty may mitigate the impact of potential false positives or false negatives that could result from pattern detection confined to the observed measurement data.

Figure 21:
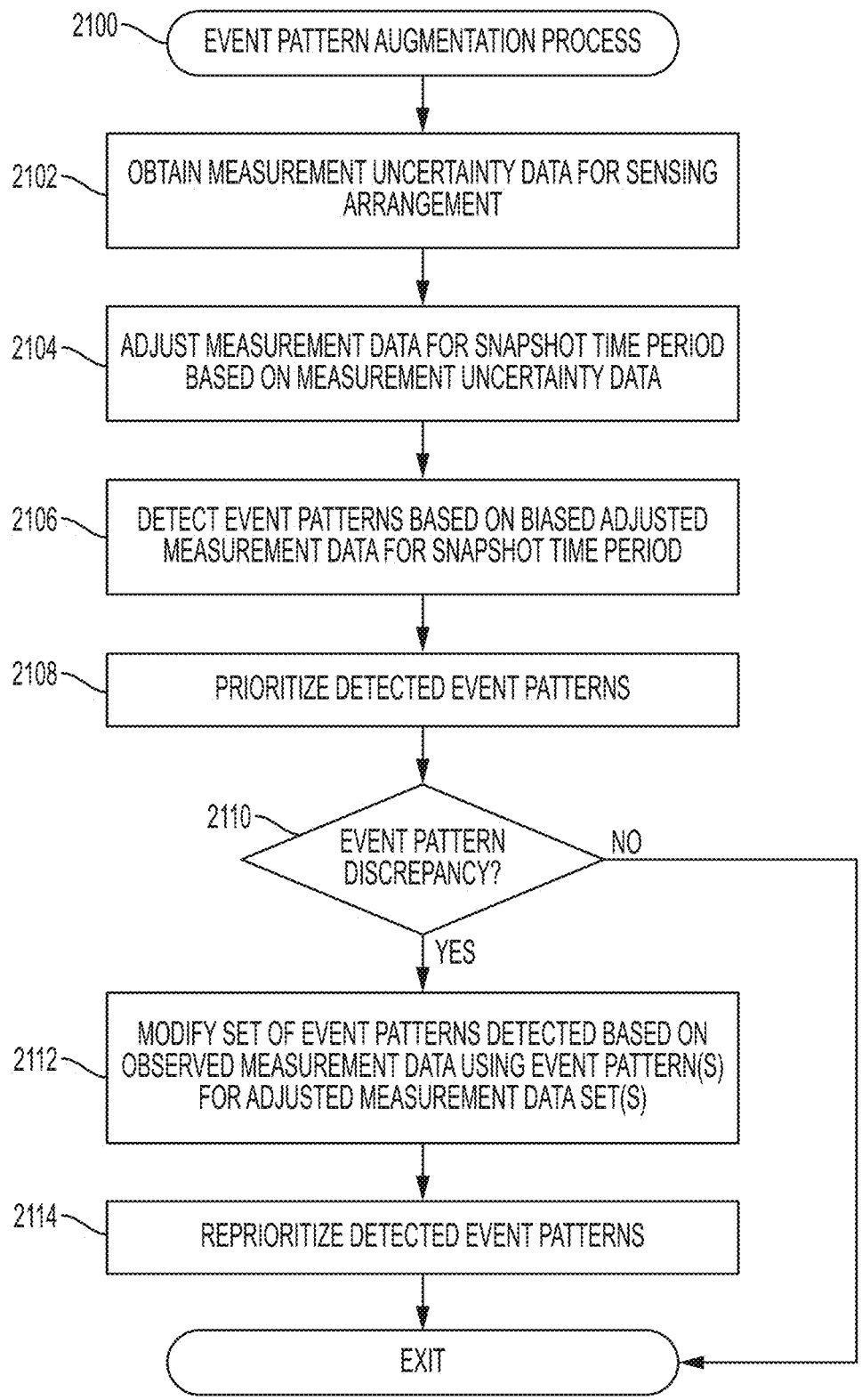
FIG. 21 is a flow diagram of an exemplary event pattern augmentation process suitable for use with the patient management system of FIG. 2 in conjunction with the snapshot presentation process of FIG. 3 to populate an event pattern detection region of a snapshot GUI display in one or more exemplary embodiments.

FIG. 21 depicts an exemplary pattern augmentation process 2100 suitable for implementation in conjunction with the snapshot presentation process 300 of FIG. 3 to modify pattern guidance displays in a manner that accounts for measurement uncertainty. The various tasks performed in connection with the pattern augmentation process 2100 may be performed by hardware, firmware, software executed by processing circuitry, or any combination thereof. For illustrative purposes, the following description refers to elements mentioned above in connection with FIG. 2. In practice, portions of the pattern augmentation process 2100 may be performed by different elements of the patient management system 200; however, for purposes of explanation, the subject matter may be described in the context of the pattern augmentation process 2100 being performed by the server 206. It should be appreciated that the pattern augmentation process 2100 may include any number of additional or alternative tasks, the tasks need not be performed in the illustrated order and/or the tasks may be performed concurrently, and/or the pattern augmentation process 2100 may be incorporated into a more comprehensive procedure or process having additional functionality not described in detail herein. Moreover, one or more of the tasks shown and described in the context of FIG. 21 could be omitted from a practical embodiment of the pattern augmentation process 2100 as long as the intended overall functionality remains intact.

In one or more exemplary embodiments, the pattern augmentation process 2100 is performed as part of the snapshot presentation process 300 of FIG. 3 after detecting and prioritizing event patterns using the observed measurement data for the snapshot time period (e.g., tasks 308, 310, 312) prior to generating the pattern guidance display. The pattern augmentation process 2100 is performed to account for the potential influence of measurement uncertainty on the observed measurement data, which, in turn, could influence the event patterns detected during the snapshot time period based on the observed measurement data.

In exemplary embodiments, the pattern augmentation process 2100 receives or otherwise obtains data that characterizes or otherwise indicates the degree of uncertainty in the measurements provided by the sensing arrangement of interest and calculating or otherwise generating one or more sets of adjusted measurement data for the snapshot time period using the observed measurement data and the measurement uncertainty data (tasks 2102, 2104). In one or more embodiments, the database 208 stores or otherwise maintains data characterizing the uncertainty in the performance of the sensing arrangement 204. In this regard, the uncertainty data may be associated with a particular device type and/or device configuration for the sensing arrangement, with the server 206 identifying the current device type and/or current device configuration for the current sensing arrangement 204 of interest and then querying, retrieving, or otherwise obtaining the measurement uncertainty data associated with the current device type and/or current device configuration.

The measurement uncertainty data may include the mean absolute difference or mean absolute relative difference associated with the sensing arrangement 204 or other statistics characterizing the dispersion in the measurements provided by the sensing arrangement 204. Depending on the embodiment, the measurement uncertainty data may be defined in relative terms (e.g., as a percentage of the measurement value) or absolute terms (e.g., as a fixed amount), and depending on the embodiment, the measurement uncertainty data may be static or vary with respect to time. In this regard, the measurement uncertainty associated with a given type or configuration of a sensing arrangement may increase and/or decrease with respect to the duration of time that the sensing arrangement (or a sensing element thereof) has been in use. For example, in one or more embodiments, the sensing arrangement 204 includes one or more interstitial glucose sensing elements generate or otherwise output electrical signals having a signal characteristic that is correlative to, influenced by, or otherwise indicative of the relative interstitial fluid glucose level in the body of a patient, where the measurement uncertainty of the interstitial glucose sensing element(s) increases with respect to time as the duration of operation of the interstitial glucose sensing element approaches the useful life of the sensing element.

In some embodiments, the measurement uncertainty data may be calculated or otherwise determined as part of the manufacturing process. For example, for a given type or configuration of sensing arrangement, a number of measurement samples may be obtained using instances of the sensing arrangement and compared to corresponding validated reference measurement values to calculate or otherwise determine one or more of the mean absolute difference, the mean absolute relative difference, the standard deviation, the variance, confidence intervals, percent agreement, and/or other statistics characterizing the dispersion or distribution of the measurement samples relative to the reference measurement values. In other embodiments, the measurement uncertainty data may be calculated or otherwise determined based on patient data maintained in the database 208. For example, for a given type or configuration of sensing arrangement 204, the server 206 may obtain historical sensed glucose measurement values obtained from various instances of the sensing arrangement 204 associated with different patients and corresponding blood glucose reference measurements and compare the historical sensed glucose measurement values to corresponding historical blood glucose reference measurement values to calculate or otherwise determine the mean absolute difference, the mean absolute relative difference, and/or the like. In this regard, some embodiments may also incorporate a temporal variable in the analysis (e.g., the time since instantiation of a sensing element associated with a respective historical sensed glucose measurement value) to support calculating or otherwise determining an equation for the mean absolute difference, the mean absolute relative difference, and/or other measurement uncertainty statistic as a function of the temporal variable.

After obtaining the measurement uncertainty data, the server 206 calculates, generates, or otherwise determines one or more sets of adjusted measurement data for the snapshot time period by adjusting the observed measurement data for the snapshot time period in accordance with a respective measurement uncertainty statistic. For example, the server 206 may determine a positively adjusted measurement data set by increasing the value of each measurement data sample during the snapshot time period by the mean absolute difference or mean absolute relative difference associated with the sensing arrangement 204. In this regard, the positively adjusted measurement data set represents the patient's potential glucose levels during the snapshot time period in the event the measurement values output by the sensing arrangement 204 were biased lower than the patient's actual glucose levels due to noise, interference, sensor site location, or some other factor. Similarly, the server 206 may determine a negatively adjusted measurement data set by decreasing the value of each measurement data sample during the snapshot time period by the mean absolute difference or mean absolute relative difference associated with the sensing arrangement 204. The negatively adjusted measurement data set represents the patient's potential glucose levels during the snapshot time period in the event the measurement values output by the sensing arrangement 204 were biased higher than the patient's actual glucose levels. In this regard, it should be noted that in practice, any number of different adjusted measurement data sets may be determined using any number of measurement uncertainty statistics, individually or in combination. Accordingly, the subject matter described herein is not intended to be limited to any particular manner or scheme for adjusting measurement data samples to account for potential uncertainty or error.

Still referring to FIG. 21, the pattern augmentation process 2100 continues by detecting and prioritizing event patterns associated with each of the adjusted measurement data sets (tasks 2106, 2108) in a similar manner as described above in the context of FIG. 3 with respect to the observed measurement data set. In this regard, the adjusted measurement data for each of the adjusted measurement data sets may be analyzed with respect to the various different event detection thresholds to identify potential event patterns occurring within the different respective monitoring periods. For example, the adjusted sensor glucose measurement values may be classified or categorized into different monitoring time periods, then the adjusted sensor glucose measurement values within a respective monitoring period may be compared to a glucose threshold value to identify a number of times that the adjusted sensor glucose measurement values would have violated the glucose threshold value within the respective monitoring period and detect an event pattern within the respective monitoring period for the adjusted measurement data set when the number is greater than one. After identifying event patterns associated with the different monitoring time periods, the detected event patterns are prioritized according to one or more prioritization criteria to obtain a prioritized list of detected event patterns for the respective adjusted measurement data set.

In exemplary embodiments, the pattern augmentation process 2100 analyzes or otherwise compares prioritized list of detected event patterns based on the observed measurement data to the prioritized list(s) of detected event patterns for the adjusted measurement data set(s) to identify when there is a discrepancy between the lists (task (2110). In some embodiments, the pattern augmentation process 2100 only analyzes a subset of the prioritized lists of detected event patterns, such as, for example, only the three highest (or top three) detected event patterns from each list. In this regard, in some embodiments, the display threshold number or other filtering criteria utilized to determine the number of event patterns for display may be obtained by the server 206 and utilized to determine the subset of detected event patterns to be compared across different data sets.

In the illustrated embodiment, when there is a discrepancy or inconsistency between the lists of detected event patterns, the pattern augmentation process 2100 modifies or otherwise alters the prioritized list of detected event patterns based on the observed measurement data using the detected event patterns for the adjusted measurement data set(s) (task 2112). For example, in some embodiments, when the highest priority event pattern detected based on adjusted measurement data set is not within the top three priority event patterns detected based on the observed measurement data set, that highest priority event pattern associated with the adjusted measurement data set may be substituted for the event pattern associated with the observed measurement data set having the third priority (e.g., the lowest prioritized event pattern associated with the top three priority event patterns). In this regard, when two different adjusted measurement data sets result in different highest priority event patterns, an augmented set of event patterns for the snapshot time period may be created that consists of the highest priority event pattern detected based on the observed measurement data and the two different highest priority event patterns detected based on the two different adjusted measurement data sets. In this regard, it should be noted that there are any number of different ways to modify or adjust the prioritized list of event patterns for presentation, and the subject matter described herein is not intended to be limited to any particular manner or scheme for augmenting the prioritized list of event patterns for display. For example, various different selection criteria or logic may be utilized to select different event patterns from different prioritized lists to obtain an augmented list of event patterns for the snapshot time period that accounts for measurement uncertainty. As described in greater detail below in the context of FIGS. 23-24, in some embodiments, one or more confidence metrics may be utilized to influence which detected event patterns are selected for presentation based on the relative confidence associated with detection of the respective event pattern.

Still referring to FIG. 21, in one or more embodiments, an equation or formula may be utilized to assign a particular value to each detected event pattern that represents its relative distribution or ranking across the prioritized lists associated with the different measurement data sets. The respective distribution metric value may then be utilized to reprioritize event patterns and obtain a prioritized list of detected event patterns across all the different measurement data sets (task 2114). Thus, the detected event patterns that are most consistently detected or otherwise have the highest distribution across different data sets may be selected for presentation due to the increased likelihood of validity regardless of measurement uncertainty, while detected event patterns that are not consistently detected or sparsely distributed may be excluded from presentation due to the likelihood of being false positives attributable to measurement uncertainty.

For example, in some embodiments, a cumulative or aggregate ranking for each respective event pattern may be determined by averaging its ranking associated with each respective measurement data set. In other embodiments, a cumulative or aggregate ranking of a particular event pattern may be calculated as a weighted sum of its ranking associated with each respective measurement data set. For example, an aggregate ranking value for an event pattern across n number different measurement data sets may be calculated using the equation $r_{net} = \Sigma r_n w_n$, where $r_n$ is the ranking of the event pattern within a respective list associated with a respective measurement data set and $w_n$ is the weighting factor assigned to the respective measurement data set, and the sum of the weighting factors is equal to one. In this regard, each measurement data set may be associated with a different weighting factor that may be utilized to preferentially rank certain measurement data sets above other measurement data sets (e.g., to preferentially weight the ranking of event patterns based on the observed measurement data set above the ranking of event patterns based on adjusted measurement data sets). As described in greater detail below in the context of FIGS. 23-24, in some embodiments, one or more confidence metrics may be utilized to further tune or adjust the relative weightings of the rankings to reflect the relative confidence associated with detection of the respective event pattern.

The cumulative or aggregate ranking may be utilized to reprioritize or rank each detected event pattern with respect to one another to obtain a prioritized augmented list of detected event patterns within the snapshot time period. For example, if a particular event pattern (e.g., a hypoglycemic event pattern associated with a pre-dinner time period) has second priority among the detected event patterns associated with the observed measurement data set but has highest priority associated with an adjusted measurement data set, while the highest priority event pattern among the detected event patterns associated with the observed measurement data set (e.g., a variability event within a lunch time monitoring period) is not among the top three highest priority event patterns associated with an adjusted measurement data set, the second priority event pattern from the observed measurement data set may be reprioritized over the previously highest priority event pattern (e.g., ranking Low SG—pre-dinner above Variable SG—lunch time) to account for potential measurement uncertainty.

After adjusting or otherwise modifying the prioritized list of detected event patterns for presentation to account for potential measurement uncertainty, the resulting augmented list of detected event patterns may be filtered (e.g., tasks 314, 316) and then the filtered augmented list of detected event patterns may be utilized to generate pattern guidance displays and related indicia on a snapshot GUI display (e.g., tasks 318, 320) in a similar manner as described above in the context of FIGS. 1-4. In this regard, FIG. 22 depicts an exemplary snapshot GUI display 2200 with a pattern detection region 2206 that reflects an augmented list of detected event patterns in accordance with the pattern augmentation process 2100 of FIG. 21.

Figure 22:
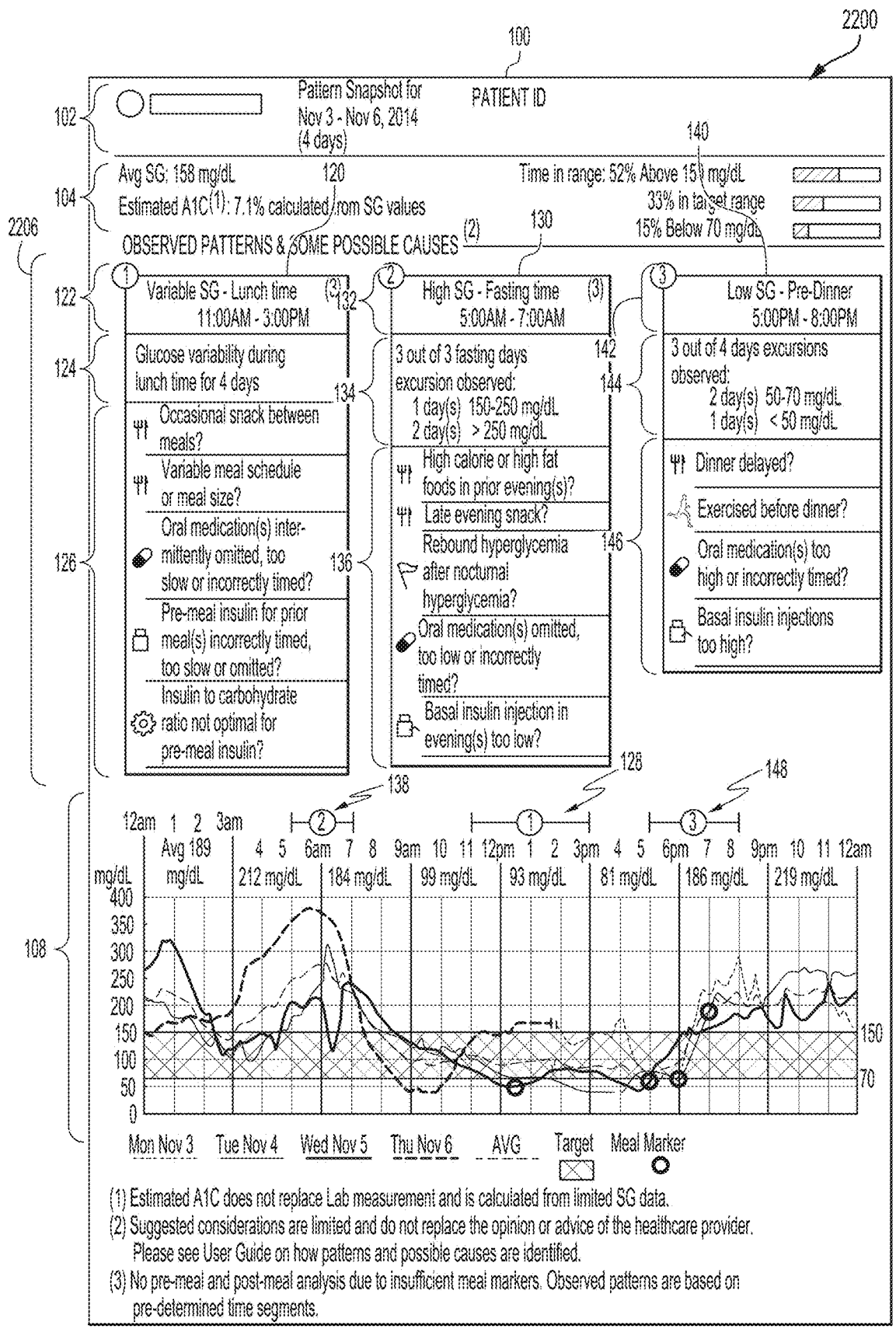
FIG. 22 depicts an exemplary embodiment of a snapshot GUI display that may be presented in conjunction with the event pattern augmentation process of FIG. 21.

In the snapshot GUI display 2200 of FIG. 22, the fasting monitoring hyperglycemic event pattern and its corresponding pattern guidance GUI display 140 are reprioritized above the pre-dinner hypoglycemic event pattern and its pattern guidance GUI display 130 based on the relative distribution and/or ranking of the fasting monitoring hyperglycemic event pattern across different measurement data sets. For example, when the observed measurement data from the snapshot period depicted in the graph overlay region 108 is adjusted upwards by the mean absolute relative difference associated with the sensing arrangement 204, pattern detection and prioritization performed on the resulting positively adjusted measurement data set may result in the lunch time variable sensor glucose event pattern being detected and prioritized first and the fasting period hyperglycemic event pattern being detected and prioritized second, with the upward adjustment in the measurement data resulting in the pre-dinner hypoglycemic event pattern no longer being detected. Thus, by virtue of the fasting period hyperglycemic event pattern being detected among both the observed and adjusted measurement data sets while the pre-dinner hypoglycemic event pattern is only detected in one of the data sets, the fasting period hyperglycemic event pattern may be reprioritized above and preferentially displayed relative to the pre-dinner hypoglycemic event pattern to reflect the greater consistency of detection of the fasting period hyperglycemic event pattern across different measurement data sets that account for measurement uncertainty. That is, the absence of adjusted measurement data sets confirming the pre-dinner hypoglycemic event pattern may be considered as indicative of a potential false positive attributable to measurement uncertainty or error, and thus, the pre-dinner hypoglycemic event pattern may be deemphasized.

Continuing the above example with another adjusted measurement data set, pattern detection and prioritization performed on the resulting negatively adjusted measurement data set (e.g., the observed measurement data adjusted downwards by the mean absolute relative difference) may result in the same prioritized list as the prioritized list based on the observed measurement data set (e.g., the lunch time variable sensor glucose event pattern followed by the pre-dinner hypoglycemic event pattern followed by the fasting period hyperglycemic event pattern). As described above, in some embodiments, the pattern augmentation process 2100 may elevate the fasting period hyperglycemic event pattern above the pre-dinner hypoglycemic event pattern by virtue of its more consistent detection and prioritization across measurement data sets. In other embodiments, the pattern augmentation process 2100 may calculate or otherwise determine an aggregate ranking of the detected event patterns across all measurement data sets, and then reprioritize or re-rank the detected event patterns according to the aggregate ranking. In this regard, since the lunch time variable sensor glucose event pattern is detected and prioritized first for each of the observed measurement data set, the positively adjusted measurement data set, and the negatively adjusted measurement data set, the aggregate ranking of the lunch time variable sensor glucose event pattern may be maintained as first (or one). However, because the fasting period hyperglycemic event pattern is ranked higher in the list for the positively adjusted measurement data set and the pre-dinner hypoglycemic event pattern is absent, the aggregate ranking of the pre-dinner hypoglycemic event pattern may be adjusted downward in the augmented list while the aggregate ranking of the fasting period hyperglycemic event pattern may be adjusted upward, such that the aggregate ranking of the fasting period hyperglycemic event pattern results in prioritization above the pre-dinner hypoglycemic event pattern.

Confidence-Based Event Pattern Prioritization

In one or more exemplary embodiments, the confidence or likelihood of occurrence of a detected event patterns is quantified probabilistically or statistically based on the measurement data in a manner that accounts for measurement uncertainty, with the confidence metric in turn being utilized to further augment or adjust the displayed patterns or perform other actions in a manner that is influenced by the value of the confidence metric. In this regard, the confidence metric value represents the degree to which pattern detection criteria for a detected event pattern have been satisfied, in terms of magnitude and/or duration, in relation to the likelihood that the satisfaction of the pattern detection criteria is due to measurement error or uncertainty. Thus, a higher confidence metric value represents a decreased probability that the detected event pattern is a false positive, whereas a lower confidence metric value represents an increased probability that the detected event pattern is a false positive. In various embodiments, confidence metric values may be determined for each detected event pattern, and then incorporated into the prioritization or ranking scheme applied to the detected event patterns (e.g., by more preferentially ranking high confidence event patterns over lower confidence event patterns) prior to filtering the detected event patterns and generating corresponding pattern guidance displays. In yet other embodiments, the confidence metric value associated with a particular event pattern may be employed substantially in real-time to adjust the manner in which user notifications or alerts are generated, to adjust the manner in which an infusion device is operated to administer fluid to a patient, or to perform other actions responsive to the event pattern.

Figure 23:
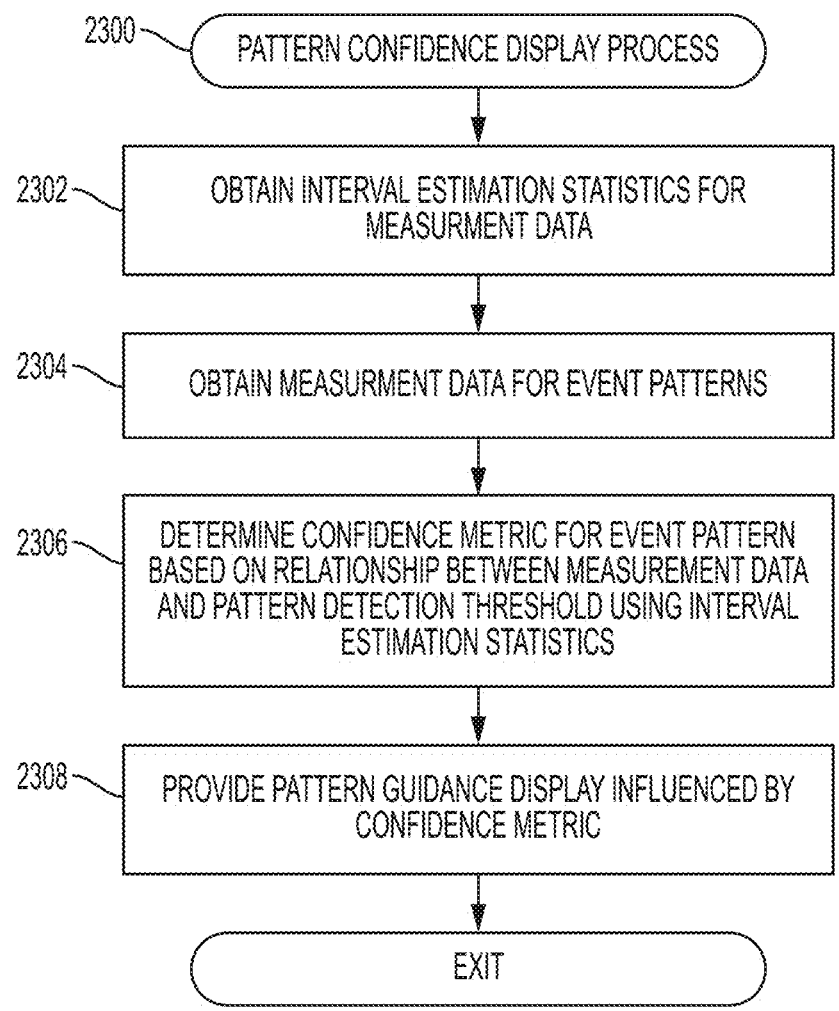
FIG. 23 is a flow diagram of an exemplary pattern confidence display process suitable for use with the patient management system of FIG. 2 in conjunction with the snapshot presentation process of FIG. 3 to populate an event pattern detection region of a snapshot GUI display in one or more exemplary embodiments.

FIG. 23 depicts an exemplary pattern confidence display process 2300 suitable for implementation in conjunction with the snapshot presentation process 300 of FIG. 3 and/or the pattern augmentation process 2100 to modify pattern guidance displays based on the relative confidence in the event pattern detection. The various tasks performed in connection with the pattern confidence display process 2300 may be performed by hardware, firmware, software executed by processing circuitry, or any combination thereof. For illustrative purposes, the following description refers to elements mentioned above in connection with FIG. 2. In practice, portions of the pattern confidence display process 2300 may be performed by different elements of the patient management system 200; however, for purposes of explanation, the subject matter may be described in the context of the pattern confidence display process 2300 being performed by the server 206. It should be appreciated that the pattern confidence display process 2300 may include any number of additional or alternative tasks, the tasks need not be performed in the illustrated order and/or the tasks may be performed concurrently, and/or the pattern confidence display process 2300 may be incorporated into a more comprehensive procedure or process having additional functionality not described in detail herein. Moreover, one or more of the tasks shown and described in the context of FIG. 23 could be omitted from a practical embodiment of the pattern confidence display process 2300 as long as the intended overall functionality remains intact.

The pattern confidence display process 2300 receives or otherwise obtains interval estimation statistics that characterize or otherwise indicate the degree of uncertainty in the measurements provided by the sensing arrangement of interest (task 2302). In this regard, the measurement interval estimation statistic characterizes the probability or confidence that the true value for the characteristic being measured is within a range about the measured value. In a similar manner as described above in the context of the pattern augmentation process 2100, the database 208 may store or otherwise maintain interval estimation statistics associated with particular device types and/or configurations for the sensing arrangement 204 for retrieval by the server 206 based on the current device type and/or current device configuration for the current sensing arrangement 204. In other embodiments, the server 206 may calculate or otherwise determine the interval estimation statistics for the sensing arrangement 204 dynamically and substantially in real-time based on historical measurement data maintained in the database 208 (e.g., based on historical sensed glucose measurement values and corresponding blood glucose reference measurements). Depending on the embodiment, the measurement uncertainty data may be defined in relative terms (e.g., as a percentage of the measurement value) or absolute terms (e.g., as a fixed amount), and depending on the embodiment, the measurement uncertainty data may be static or vary with respect to time.

In a similar manner as described above, in some embodiments, the interval estimation statistics may be calculated or otherwise determined as part of the manufacturing process. For example, for a given type or configuration of sensing arrangement, a number of measurement samples may be obtained using instances of the sensing arrangement and compared to corresponding validated reference measurement values to calculate or otherwise determine one or more of the standard deviation, the variance, percent agreement, confidence intervals, credible intervals and/or other statistics characterizing the dispersion or distribution of the measurement samples about the reference measurement values. In other embodiments, the measurement uncertainty data may be calculated or otherwise determined based on patient data maintained in the database 208 in a similar manner as described above in the context of the pattern augmentation process 2100 of FIG. 21. Additionally, some embodiments may also incorporate a temporal variable such that the interval estimation statistics vary with respect to time.

Still referring to FIG. 23, the pattern confidence display process 2300 continues by retrieving or otherwise obtaining a subset of measurement data pertaining to a detected event pattern and calculating or otherwise determining a confidence metric associated with the detected event pattern based on the relationship between the subset of measurement data and the pattern detection criteria using one or more interval estimation statistics (tasks 2304, 2306). For a detected event pattern, the server 206 obtains the values for the underlying measurement data samples that satisfied or violated a pattern detection threshold or other criterion that resulted in the detection of an event pattern. For example, for a hyperglycemic event pattern associated with a particular monitoring period, the server 206 obtains, from the database 208, the values for the measurement data samples associated with that monitoring period that are greater than the hyperglycemic event threshold.

In exemplary embodiments, for each measurement data sample of the event pattern subset of measurement data, the server 206 calculates or otherwise determines the difference between the measured value and the threshold value for detecting the respective event pattern. Based on the difference between the measured value and the threshold, the interval estimation statistic(s) for the sensing arrangement 204 are used to assign a value to the respective measurement data sample that corresponds to the probability or confidence that the true value for the measured characteristic violates or satisfies the pattern detection threshold. For example, if a first measured sensor glucose measurement value associated with a hyperglycemic event pattern is 5 mg/dL above the hyperglycemic event detection threshold and the confidence interval associated with the sensing arrangement 204 provides that there is a 75% probability that the true interstitial glucose measurement value is greater than 5 mg/dL less than the measured value, then the server 206 may assign a confidence value of 75% (or 0.75) to that measurement data sample. For a subsequent measured sensor glucose measurement value that is 10 mg/dL above the hyperglycemic event detection threshold, the server 206 may identify, based on the confidence interval associated with the sensing arrangement 204, that there is a 90% probability that the true interstitial glucose measurement value is greater than 10 mg/dL less than the measured value, then the server 206 may assign a confidence value of 90% (or 0.9) to that measurement data sample.

After assigning a confidence value to each measurement data sample associated with the event pattern, an aggregate confidence value associated with the event pattern may be calculated or otherwise determined based on the individual confidence values. For example, Bayes' theorem may be utilized to calculate an overall probability or confidence for occurrence of an event pattern as function of the confidence values associated with the individual measurement data samples indicative of the event pattern, such as, for example, the probability of a threshold being crossed given the previous measurement data sample's probability of crossing the threshold (e.g., $P(A|A-1)$). In this regard, it should be noted that as the duration for which the measurement samples satisfy or violate a detection criteria increases, the overall confidence metric value associated with the detected event pattern increases, even though the confidence value associated with the individual measurement data samples may be relatively low.

In one or more exemplary embodiments, the pattern confidence display process 2300 generates or otherwise provides a pattern guidance display that is influenced by the confidence metric value associated with a detected event pattern (task 2308). For example, in one or more embodiments, the pattern guidance display associated with the detected event pattern may include a graphical representation of the confidence value associated with the detected event pattern or other indicia of the relative confidence in the detection of the event pattern. In this regard, the server 206 may modify a color or other visually distinguishable characteristic associated with a pattern guidance display to emphasize or deemphasize the pattern guidance display, and thereby indicate or otherwise communicate relatively higher or lower confidence in a given event pattern.

In one or more embodiments, the prioritization of the detected event patterns associated with a snapshot time period is influenced by the confidence metric values associated with the respective event patterns. For example, in one embodiment of the snapshot presentation process 300, the detected event patterns may be prioritized primarily based on the confidence metric values associated therewith prior to secondarily prioritizing the detected event patterns based on event type (e.g., task 310) and thirdly based on monitoring period (e.g., task 312). In such embodiments, the highest confidence event patterns may be preferentially displayed above other detected event patterns. In yet other embodiments, a ranking or prioritization algorithm may be employed by the server 206 to calculate or otherwise determine a value for a ranking metric associated with a respective event pattern as a function of its associated confidence value and one or more other factors or characteristics associated with the event pattern, such as, for example, its associated event type, its associated monitoring period, and/or the like. In such embodiments, the server 206 may then sort, order, or otherwise prioritize detected event patterns according to their respective ranking metric values.

In yet other embodiments, the snapshot presentation process 300 may utilize the confidence metric values associated with the respective event patterns as filtering criteria. For example, rather than filtering event patterns within a respective monitoring period based on priority (e.g., task 314), instead, the snapshot presentation process 300 may filter the prioritized list of detected event patterns first by confidence level within the respective monitoring periods to remove or exclude lower confidence event patterns and thereby select or retain only the highest confidence event pattern detected for each respective monitoring period. For example, if a hypoglycemic event pattern, a hyperglycemic event pattern, and a variability event pattern are all detected within a particular monitoring period, the server 206 may remove the two event patterns having the lowest associated overall confidence value from the prioritized list of detected event patterns, so that the list retains only the event pattern associated with the monitoring period having the highest overall confidence value.

In one or more embodiments, the pattern confidence display process 2300 is performed in conjunction with the pattern augmentation process 2100 of FIG. 21 when augmenting the list of event patterns for presentation based on measurement uncertainty. In this regard, the overall confidence value associated with each detected event pattern for each measurement data set may be considered as a factor when selecting, combining, or otherwise reprioritizing event patterns based on their distribution across multiple data sets. For example, the confidence value may be utilized in conjunction with other weighting factors to increase the weight or relevance of the rankings assigned to higher confidence event patterns in the overall ranking or prioritization of event patterns while decreasing the weight or relevance of the rankings assigned to lower confidence event patterns. Thus, the event patterns that are more consistently detected across different data sets and with higher levels of confidence may be more preferentially selected or displayed within the augmented list relative to event patterns that are less consistently detected across different data sets or have lower levels of confidence associated therewith. In one embodiment, an augmented list of detected event patterns may be determined by selecting the highest confidence event pattern from among the detected event patterns associated with each respective measurement data set. For example, an augmented list of three detected event patterns may be created by selecting the highest confidence detected event pattern associated with the observed measurement data set, highest confidence detected event pattern associated with the positively adjusted measurement data set, and the highest confidence detected event pattern associated with the negatively adjusted measurement data set. In some embodiments, to eliminate redundancy and to increase the number of displayed event patterns, the next highest confidence detected event pattern associated with a particular measurement data set may be selected if its highest confidence detected event pattern has already been selected for inclusion in the augmented list.

It should be noted that there are any number of different ways the confidence values assigned to detected event patterns may be utilized in conjunction with the snapshot presentation process 300 of FIG. 3 or the pattern augmentation process 2100 of FIG. 21 to alter the manner in which detected event patterns are ordered or displayed, and the subject matter described herein is not intended to be limited to any particular algorithm, scheme, or manner for utilizing the confidence level associated with the detected event patterns. It should also be noted that the confidence value assigned to a detected event pattern is not limited to use with the snapshot presentation processes or GUI displays described herein, and could independently be utilized in real-time to adjust other alerts or notifications provided to a user, or to alter operation of another medical device based on the degree of confidence.

For example, the pattern confidence display process 2300 may be performed at any end user device 202, 204, 208 in the system 200 to detect an event pattern and dynamically adjust or alter alerts or user notifications provided to a user pertaining to that event pattern in real-time based on the confidence level. In this regard, the alerting may be escalated when the confidence level associated with an event pattern increases above a particular threshold, or deescalated when the confidence level is below the threshold. For example, a first hypoglycemic event alert may be generated or otherwise provided at a device 202, 204, 208 when a hypoglycemic event pattern is detected with a confidence level greater than an initial alerting threshold (e.g., 50%). Subsequently, as the difference between the measured sensor glucose values and the hypoglycemic event detection increases or the number of samples of measured sensor glucose values below the hypoglycemic event detection increases, the overall confidence level associated with the hypoglycemic event pattern may increase above a second alerting threshold (e.g., 90%), at which point the hypoglycemic event alerting is escalated (e.g., by generating haptic or auditory output, the server 206 pushing a text message or other notification to various devices 208 associated with the patient or the patient's healthcare provider, emergency contacts, etc.). It should be noted that any number of different levels of alerting may be implemented in practice, and the subject matter described herein is not intended to be limited to any particular type of alerting scheme.

As another example, the confidence level associated with a currently detected event pattern may be utilized to dynamically adjust operation of an infusion device 202, 602, 700, 1002 regulating the condition of a patient. For example, when a hyperglycemic event pattern is detected with a confidence level greater than a control adjustment threshold (e.g., 50%), one or more gain parameters 1220, 1222, 1224 associated with a closed-loop control system 1200 utilized by the infusion device 202, 602, 700, 1002 may be dynamically adjusted to increase the responsiveness of the control system 1200 and thereby increase insulin delivery to reduce the difference between the measured sensor glucose values 1204 and the target glucose value 1202. In this regard, when the measured sensor glucose values 1204 fall below the hyperglycemic event detection threshold, the gain parameters 1220, 1222, 1224 associated with a closed-loop control system 1200 may be restored to their original values to revert to normal operation of the closed-loop control system 1200. It should be noted that the confidence level associated with a detected event pattern may be utilized in conjunction with predicted glucose values or other control schemes to dynamically adjust operation of the infusion device 202, 602, 700, 1002 responsive to a patient's condition in real-time, and the subject matter described herein is not limited to any particular manner or scheme for dynamically adjusting infusion device operation.

Figure 24:
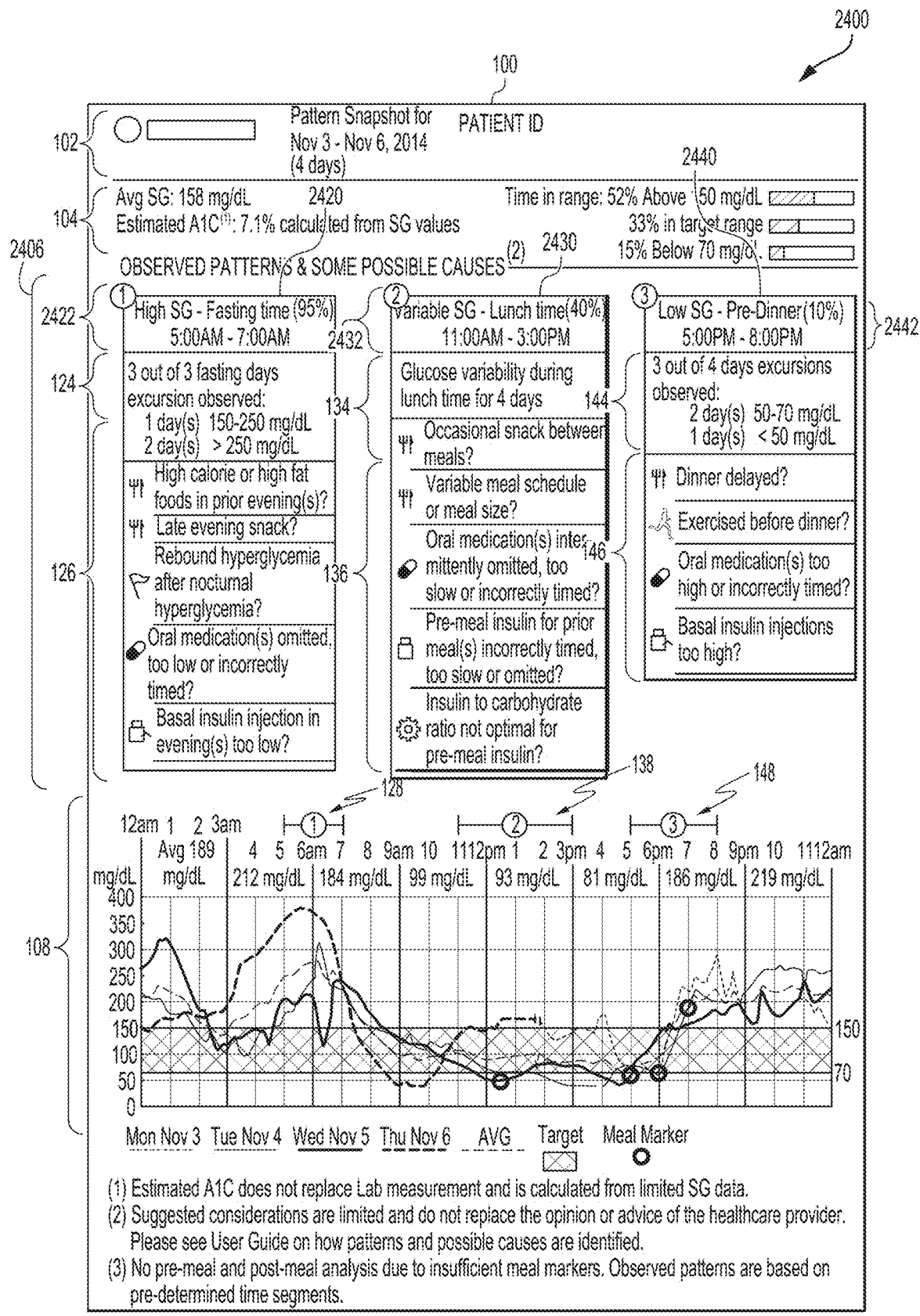
FIG. 24 depicts an exemplary embodiment of a snapshot GUI display that may be presented in conjunction with the pattern confidence display process of FIG. 23.

FIG. 24 depicts an exemplary snapshot GUI display 2400 with a confidence-influenced pattern detection region 2406 that reflects list of detected event patterns prioritized or otherwise selected for presentation based on confidence in accordance with the pattern confidence display process 2300 of FIG. 23. In FIG. 24, the header regions 2422, 2432, 2442 of the pattern guidance displays 2420, 2430, 2440 include graphical representations of the respective confidence metric values associated with the respective event patterns. In the illustrated GUI display 2400, the pattern guidance displays 2420, 2430, 2440 are ordered such that the pattern guidance display 2420 for the highest confidence detected event pattern is preferentially displayed relative to the other pattern guidance displays 2430, 2440. For example, based on the magnitude of the difference between the measured sensor glucose values and the hyperglycemic event detection threshold and duration of time during which the measured sensor glucose values exceed the hyperglycemic event detection threshold in the fasting time period, the pattern confidence display process 2300 may calculate or otherwise determine a confidence level of 95% in the detection of the fasting period hyperglycemic event pattern. Conversely, based on a relatively smaller difference between the measured sensor glucose values and the hypoglycemic event detection threshold in the pre-dinner time period and the relatively short duration of time during which the measured sensor glucose values were below the hypoglycemic event detection threshold, the pattern confidence display process 2300 may calculate or otherwise determine a confidence level of 10% in the detection of the pre-dinner hypoglycemic event pattern. Thus, the fasting period hyperglycemic event pattern may be prioritized above the lunch period variability event pattern, which, in turn, is prioritized above the pre-dinner hypoglycemic event pattern based on their respective confidence values.

In some embodiments, the header regions 2422, 2432, 2442 of the pattern guidance displays 2420, 2430, 2440 and/or the graph markers 128, 138, 148 may be rendered using different visually distinguishable characteristics that graphically convey the level of confidence associated therewith. For example, bolding, color, or other graphical effects may be utilized to emphasize higher confidence event patterns (e.g., event patterns with a confidence level above a threshold) relative to other event patterns having lower confidence (e.g., event patterns with a confidence level below the threshold).

Figure 25:
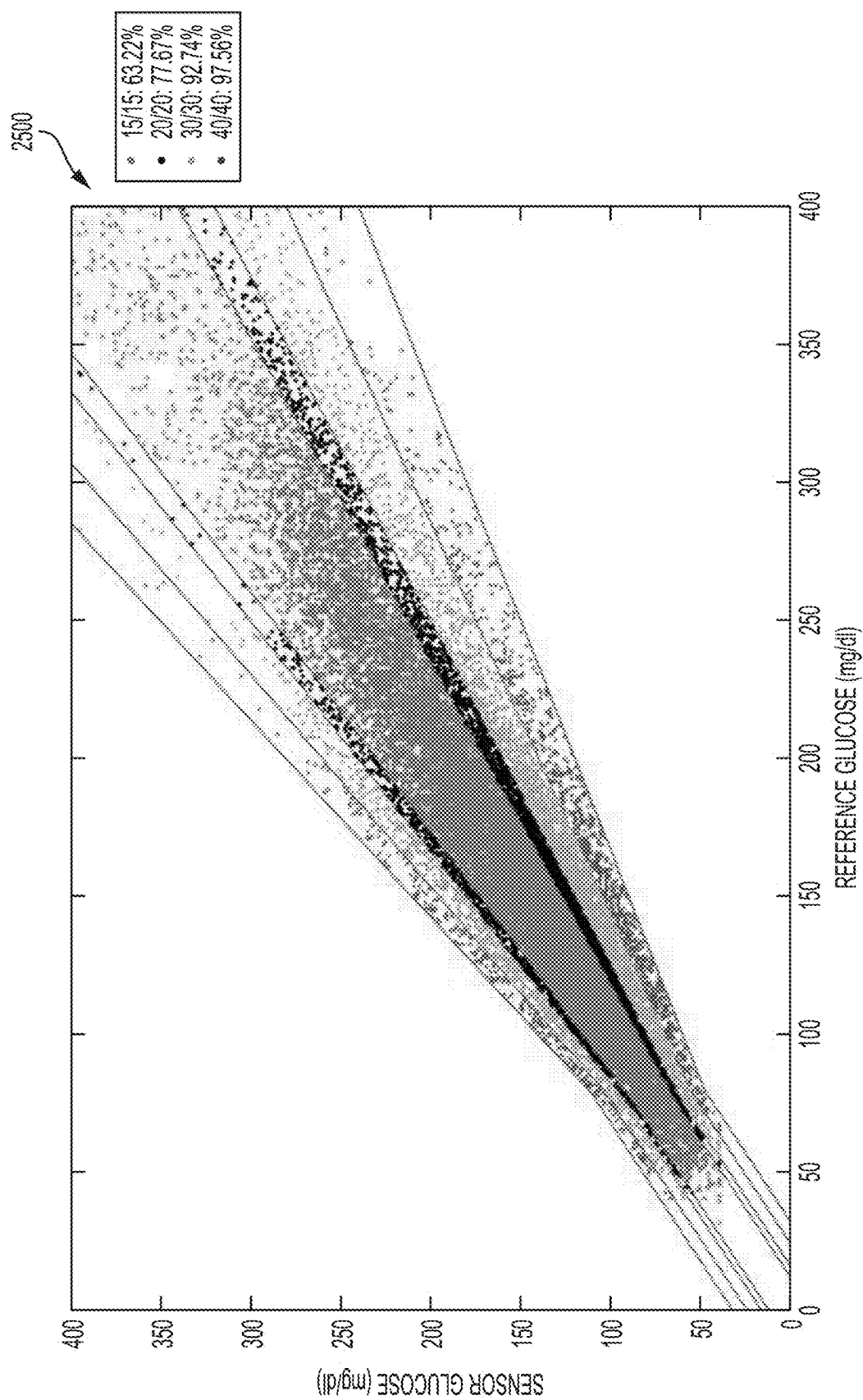
FIG. 25 is a graph depicting an exemplary relationship between sensed measurement values and reference measurement values suitable for use in determining an interval estimation statistic for use in the pattern confidence display process of FIG. 23 in one exemplary embodiment.

FIG. 25 depicts an example graph 2500 depicting the relationship between sensed glucose measurement values and corresponding blood glucose reference measurement values that may be utilized for calculating or otherwise determining the percent agreement for use as the interval estimation statistic in the pattern confidence display process 2300. In this regard, if a first measured sensor glucose measurement value associated with a hyperglycemic event pattern is 15 mg/dL above (or otherwise between 15 mg/dL and 20 mg/dL above) the hyperglycemic event detection threshold and the percent agreement associated with the sensing arrangement 204 provides that there is a 63.22% probability that the true interstitial glucose measurement value is within 15 mg/dL of the measured value, then the server 206 may assign a confidence value of 63.22% (or $P1=0.6322$) to that measurement data sample. For a subsequent measured sensor glucose measurement value that is 20 mg/dL above (or otherwise between 20 mg/dL and 30 mg/dL above) the hyperglycemic event detection threshold, the server 206 may identify, based on the percent agreement associated with the sensing arrangement 204, that there is a 77.67% probability that the true interstitial glucose measurement value is greater than 20 mg/dL less than the measured value, then the server 206 may assign a confidence value of 77.67% (or $P2=0.7767$) to that measurement data sample. Based on the confidence value of consecutive measurement samples, Bayes' theorem may be utilized to calculate an overall probability or confidence for the hyperglycemic event of 85.7% using the equation $$P(2 \mid 1) = \frac{P(2)P(1 \mid 2)}{P(1)} = \frac{0.7767 \times 0.6976}{0.6322} = 0.857.$$

Accordingly, a pattern guidance display for the hyperglycemic event may include a graphical representation of the confidence level of 85.7% or other graphical indicia of the relative confidence in the hyperglycemic event. Additionally, if an alerting scheme were employed with two different alerting thresholds (e.g., 50% and 80%), a first number or type of user notification(s) associated with the 50% threshold may be generated to notify the patient or other user of a potential hyperglycemic event in real-time in response to the first measurement value with a confidence value of 63.22% that exceeds the lower 50% alerting threshold, and then subsequently generate a second number or type of user notification(s) associated with the 80% threshold to escalate alerting of the potential hyperglycemic event in real-time in response to the second measurement value resulting in an overall confidence value of 85.7% that exceeds the higher 80% alerting threshold, even though neither measurement value independently provides an 80% confidence level.

It should be noted that numerous different percent agreement bands may be defined based on the graph 2500 depicted in FIG. 25 and the subject matter is not intended to be limited to any particular implementation. For example, narrower or higher resolution percent agreement bands may be defined (e.g., for each integer value, every +/−5 mg/dL, etc.), and/or percent agreement bands may be defined in relative terms on a percentage basis. Thus, any number or type of different percent agreement metrics may be utilized in a practical implementation to provide a desired level of resolution or granularity in assigning confidence values to individual measurement samples.

By virtue of the subject matter described herein, the impact of measurement uncertainty may be accounted for when detecting, prioritizing, and/or filtering event patterns for presentation. Preferentially displaying or emphasizing detected event patterns that are more likely to reflect a true occurrence (or are less likely to be a false positive) allows doctors, healthcare providers, patients, or other users of the GUI displays provided herein to rely on the presented event patterns and guide patient therapy accordingly with greater confidence. Additionally, incorporating confidence metrics also allows for more robust or complex alerting or control schemes that better account for measurement uncertainty when responding to detected events.

For the sake of brevity, conventional techniques related to glucose sensing and/or monitoring, bolusing, meal boluses or correction boluses, and other functional aspects of the subject matter may not be described in detail herein. In addition, certain terminology may also be used in the herein for the purpose of reference only, and thus is not intended to be limiting. For example, terms such as "first", "second", and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not necessarily limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. A method of presenting information pertaining to operation of a medical device, the method comprising:
    obtaining, by a computing device, historical glucose measurement data for a patient from a database;
    identifying, by the computing device based on the historical glucose measurement data, a first set of event patterns within respective ones of a plurality of monitoring periods, wherein each monitoring period of the plurality of monitoring periods corresponds to a different time of day corresponding to a different subset of the historical glucose measurement data, and wherein the first set of event patterns comprises a first list of event patterns;
    obtaining an adjusted set of glucose measurement data determined based on the historical glucose measurement data and an uncertainty metric associated with the historical glucose measurement data;
    identifying, by the computing device based on the adjusted set of glucose measurement data, one or more event patterns within respective ones of the plurality of monitoring periods, wherein the identified one or more event patterns comprise a second list of event patterns;
    determining, by the computing device, a discrepancy between the first list of event patterns and the second list of event patterns;
    based on the determination that there is the discrepancy between the first list of event patterns and the second list of event patterns, adjusting, by the computing device, the first list of event patterns based on the second list of event patterns to obtain an adjusted list of event patterns, wherein adjusting the first list of event patterns based on the second list of event patterns comprises at least one of adjusting an order in which event patterns are identified in the first list of event patterns based on an order in which event patterns are identified in the second list of event patterns or including an event pattern from the second list of event patterns in the first list of event patterns to obtain the adjusted list of event patterns; and
    generating, by the computing device, a graphical user interface display comprising an event detection region based at least in part on the first set of event patterns and the identified one or more event patterns, wherein the event detection region comprises a plurality of pattern guidance displays corresponding to the adjusted list of event patterns, and wherein at least one of the plurality of pattern guidance displays includes a graphical representation of a recommended therapeutic remedial action, the method further comprising, responsive to a user selection of the graphical representation of the recommended therapeutic remedial action, automating reprogramming of the medical device for implementing the recommended therapeutic remedial action.

2. The method of claim 1, further comprising:
prioritizing, by the computing device, the first set of event patterns based on one or more prioritization criteria, resulting in a first prioritized list of event patterns;
filtering, by the computing device, the first prioritized list based on one or more filtering criteria to obtain the first list of event patterns;
prioritizing, by the computing device, the identified one or more event patterns based on the one or more prioritization criteria, resulting in a second prioritized list of event patterns; and
filtering, by the computing device, the second prioritized list based on the one or more filtering criteria to obtain the second list of event patterns, wherein:
the respective pattern guidance displays of the plurality of pattern guidance displays are ordered in accordance with the adjusted list of event patterns.

3. The method of claim 1, wherein the respective pattern guidance displays of the plurality of pattern guidance displays are ordered in accordance with the adjusted list of event patterns.

4. The method of claim 1, further comprising generating, by the computing device, a snapshot graphical user interface display comprising a graph overlay region comprising a graphical representation of the historical glucose measurement data with respect to a time of day and the event detection region below the graph overlay region.

5. The method of claim 1, further comprising determining the adjusted set of glucose measurement data by adjusting each sample of the historical glucose measurement data using the uncertainty metric to obtain the adjusted set of glucose measurement data.

6. The method of claim 1, the historical glucose measurement data being obtained from a glucose sensing arrangement, wherein obtaining the adjusted set of glucose measurement data comprises adjusting the historical glucose measurement data based on the uncertainty metric associated with the glucose sensing arrangement.

7. A computer-readable medium having computer-executable instructions stored thereon that, when executed by a processing system of the computing device, cause the processing system to perform the method of claim 1.

8. A system comprising:
a database to maintain historical glucose measurement data for a patient; and
a computing device coupled to the database and configured to:
identify, based on the historical glucose measurement data, a first set of event patterns within respective ones of a plurality of monitoring periods, wherein each monitoring period of the plurality of monitoring periods corresponds to a different time of day corresponding to a different subset of the historical glucose measurement data, and wherein the first set of event patterns comprises a first list of event patterns;
obtain an adjusted set of glucose measurement data determined based on the historical glucose measurement data and an uncertainty metric associated with the historical glucose measurement data;
identify, based on the adjusted set of glucose measurement data, one or more event patterns within respective ones of the plurality of monitoring periods, wherein the identified one or more event patterns comprise a second list of event patterns;
determine a discrepancy between the first list of event patterns and the second list of event patterns;
based on the determination that there is the discrepancy between the first list of event patterns and the second list of event patterns, adjust the first list of event patterns based on the second list of event patterns to obtain an adjusted list of event patterns, wherein to adjust the first list of event patterns based on the second list of event patterns, the computing device is configured to at least one of adjust an order in which event patterns are identified in the first list of event patterns based on an order in which event patterns are identified in the second list of event patterns or include an event pattern from the second list of event patterns in the first list of event patterns to obtain the adjusted list of event patterns; and
generate a graphical user interface display comprising an event detection region based at least in part on the first set of event patterns and the identified one or more event patterns, wherein the event detection region comprises a plurality of pattern guidance displays corresponding to the adjusted list of event patterns, and wherein at least one of the plurality of pattern guidance displays includes a graphical representation of a recommended therapeutic remedial action, and
wherein the computing device is configured to, responsive to a user selection of the graphical representation of the recommended therapeutic remedial action, automate reprogramming of a medical device for implementing the recommended therapeutic remedial action.

9. The system of claim 8, wherein:
the computing device prioritizes the first set of event patterns based on one or more prioritization criteria for generating the first list of event patterns, prioritizes the identified one or more event patterns based on the one or more prioritization criteria for generating the second list of event patterns; and
the respective pattern guidance displays of the event detection region are ordered in accordance with the adjusted list of event patterns.

10. The system of claim 8, wherein the medical device comprises a sensing arrangement and the uncertainty metric comprises a statistic associated with the sensing arrangement.

11. The system of claim 10, wherein the statistic comprises a mean absolute difference, a mean absolute relative difference, a standard deviation, or a variance associated with measurements by the sensing arrangement.

12. The system of claim 11, wherein the computing device determines the adjusted set of the measurement values by increasing or decreasing the measurement values based on the statistic.

13. The system of claim 8, wherein:
the computing device determines an overall ranking for each respective event pattern of the adjusted list of event patterns and prioritizes each respective event pattern in the adjusted list of event patterns in accordance with the overall ranking; and
the respective pattern guidance displays of the event detection region are ordered in accordance with the prioritization of the adjusted list of event patterns.

14. The system of claim 8, wherein the computing device determines a confidence metric associated with each respective event pattern of the first and second lists of event patterns and prioritizes each respective event pattern in the first and second lists of event patterns in accordance with the confidence metric; and the respective pattern guidance displays of the event detection region are ordered in accordance with the prioritization of the adjusted list of event patterns.

15. The system of claim 8, wherein the medical device is an infusion device operable to deliver fluid to a body of the patient for implementing the recommended therapeutic remedial action, wherein the fluid influences the physiological condition.

16. The system of claim 8, wherein the database stores the uncertainty metric in association with the medical device.

17. The system of claim 8, wherein the computing device provides a snapshot graphical user interface display including the event detection region to a client computing device communicatively coupled to the computing device, the client computing device displaying the snapshot graphical user interface display on a display device associated therewith.

18. The system of claim 8, wherein the medical device comprises a continuous glucose monitoring (CGM) device.

\* \* \* \* \*